US008802420B2

(12) United States Patent
Handelsman et al.

(10) Patent No.: US 8,802,420 B2
(45) Date of Patent: Aug. 12, 2014

(54) **CONSTRUCTION OF A QUADRUPLE ENTEROTOXIN-DEFICIENT MUTANT OF *BACILLUS THURINGIENSIS***

(75) Inventors: Jo Emily Handelsman, North Branford, CT (US); Amy Klimowicz, Madison, WI (US); Changhui Guan, Cheshire, CT (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 13/154,857

(22) Filed: Jun. 7, 2011

(65) Prior Publication Data

US 2012/0164105 A1 Jun. 28, 2012

Related U.S. Application Data

(60) Provisional application No. 61/353,314, filed on Jun. 10, 2010.

(51) Int. Cl.
*C12N 1/20* (2006.01)

(52) U.S. Cl.
USPC .................................. 435/252.31; 435/252.5

(58) Field of Classification Search
CPC ..................................................... A01N 63/00
See application file for complete search history.

(56) References Cited

U.S. PATENT DOCUMENTS 6,602,712 B2 * 8/2003 Handelsman et al. ........ 435/440

OTHER PUBLICATIONS

Key-Poku et al (Can. J. Microbiol 53:1283-1290, 2007).*
Swiecicka et al (Microbial Ecology, 52:544-551, 2006).*
Fagerlund et al (Microbiology, 154:693-704, 2008).*
Rivera (FEMS Microbiology Letters 190:151-155, 2000).*
Fagerlund, A. et al., "*Bacillus cereus* Nhe is a pore-forming toxin with structural and functional properties similar to the ClyA (HlyE, SheA) family of haemolysins, able to induce osmotic lysis in epithelia" Microbiology, 2008, vol. 154, pp. 693-704.
Fagerlund, A. et al., "Genetic and functional analysis of the cytK family of genes in *Bacillus cereus*", 2004, Microbiology, vol. 150, pp. 2689-2697.
Kyei-Poku, G. et al., "Detection of *Bacillus cereus* virulence factors in commercial products of *Bacillus thuringiensis* and expression of diarrheal enterotoxins in a target insect", Can. J. Microbiol., 2007, vol. 53, pp. 1283-1290.
Rivera, A.M.G. et al., "Common occurrence of enterotoxin genes and enterotoxicity in *Bacillus thuringiensis*", FEMS Microbiol. Letters, 2000, vol. 190, pp. 151-155.
Swiecicka, I. et al., " Hemolytic and nonhemolytic enterotoxin genes are broadly distributed among *Bacillus thuringiensis* isolated from wild mammals", Microbial Ecology, 2006, vol. 52, pp. 544-551.
Klimowicz, A.K. et al., "A quadruple-enterotoxin-deficient mutant of *Bacillus thuringiensis* remains insecticidal", Microbiology, 2010, vol. 156, pp. 3575-3583.

* cited by examiner

*Primary Examiner* — Patricia A Duffy
(74) *Attorney, Agent, or Firm* — Quarles & Brady LLP

(57) ABSTRACT

Some HBL and NHE enterotoxins are known to cause food-borne diseases in humans. Enterotoxin-deficient mutants of member strains of the *Bacillus cereus* group that do not produce HBL, $HBL_{a1}$, $HBL_{a2}$, or NHE enterotoxins are disclosed. Enterotoxin-deficient mutants are suitable for use as biocontrol agents. Methods for making the mutants and for using the mutants are described.

4 Claims, 4 Drawing Sheets

SEQUENCE LISTING

```
<160> NUMBER OF SEQ ID NOS: 119

<210> SEQ ID NO 1
<211> LENGTH: 1261
<212> TYPE: DNA
<213> ORGANISM: Bacillus thuringiensis

<400> SEQUENCE: 1

tcctatcaat actctcgcaa caccaatcgt tcaagcagaa actcaacaag aaaacatgga      60

tatttcttca tcattacgaa aattaggtgc gcattctaaa ttagtccaaa cgtatattga     120

tcaatcttta atgagtccta atgtacagct agaggaagtc ccagctttaa ataccaatca     180

attcctaatc aaacaagata tgaaggaatg gtcatcggaa ctctatccac agttaattct     240

attaaattca aaaagtaaag gatttgtaac aaaatttaat agttattacc cgacattaaa     300

atcgtttgta gacaataaag aagatagaga agggttttcg gatagacttg aagtacttca     360

agaaatggct atgacgaatc aagaaaatgc gcaacgacaa atcaatgaat taacagatct     420

taaattacag cttgataaaa aattaaaaga ttttgatact aatgtggcaa ctgcgcaagg     480

catactaagt acagatggaa caggaaaaat agatcagtta aaaaatgaaa tattaaatac     540

caaaaaagca attcaaaatg atttacagca aattgcatta ataccaggag ctttaaatga     600

gcagggattt gctatattca aagaagttta tagtctttca aaagaaatta ttgaaccggc     660

tgctcaagca ggggtggcag cgtataacaa aggaaaagaa attaacaact ctattctaga     720

agcggagaaa aaagcggcgc aagaagcgac agaacaaggt aaaactgctc tagagattga     780
```

-continued

```
atcagcaaaa aaagcagctc gtgaagcaat tgagaaaagc aaacaaggtg aaatagcagc    840

cgcagccgca gcaaaaacac aagagtatga cctgatgaaa gccattgata ccgaaaagat    900

taagaaaaca tttggcgttt ttgctgaagt aaataaatta acagcagaac agcgagcata    960

tttagatgat ttagagaaac aaaatcaaaa aatatatgat ttaacaacga aattatcaat   1020

agctgattta caaaaatcaa tgcttcttct tacacaaaat gatttgcata cgtttgcaaa   1080

tcaagtagat gtagaacttg atctactaaa gcgctataaa gaagatttaa atctaataaa   1140

aaatagcatt acaaaattat ctactaatgt tgatacaact aacgagcagt ctcaaaaaga   1200

tacattaaga caattaaaaa atgtaataag ttaccttgaa gaacaagtat ataaatttta   1260

a                                                                   1261
```

<210> SEQ ID NO 2
<211> LENGTH: 1320
<212> TYPE: DNA
<213> ORGANISM: Bacillus cereus

<400> SEQUENCE: 2

```
atgaaaacta aaataatgac aggattttta ataacatcca ttgtaactgg agcaactatt     60

cctatcaata ctctcgcaac accaatcgtt caagcagaaa ctcaacaaga aaacatggat    120

atttcttcat cattacgaaa attaggtgcg caatctaaat taatccaaac gtatattgat    180

caatctttaa tgagtcctaa tgtacagcta gaggaagtcc cagctttaaa taccaatcaa    240

ttcctaatca aacaagatat gaaggaatgg tcatcggaac tctatccaca gttcattcta    300

ttaaattcaa aaagtaaagg atttgtaaca aaatttaata gttattaccc gacattaaaa    360

tcgtttgtag acaataaaga agatagagaa gggttttcgg atagacttga agtacttcaa    420

gaaatggcta tgacgaatca agaaaatgcg caacgacaaa tcaatgaatt aacagatctt    480

aaattacagc ttgataaaaa attaaaagat tttgatacta atgtggcaac tgcgcaaggc    540

atactaagta cagatggaac aggaaaaata gatcagttaa aaaatgaaat attaaatacc    600

aaaaaagcaa ttcaaaatga tttacagcaa attgcattaa taccaggggc tttaaatgaa    660

cagggatttg ctatattcaa agaagtttat agtctttcaa aagaaattat tgaaccagct    720

gctcaagcag gggtggcagc gtataacaaa ggaaaagaaa ttaacaactc tattctagaa    780

gcggagaaaa aagtggcgca agaagcgaca gaacaaggta aaactgctct agagattgaa    840

tcagcaaaaa aagcagctcg tgaagcaatt gagaaaagca aacaaggtga aatagcagcc    900

gcagccgcag caaaaacaca agagtatgac ctgatgaagg tcattgatac cgaaaagatt    960

aagaaaacat ttggcgtttt tgctgaagta aataaattaa cagcagaaca gcgagcatat   1020

ttagatgatt tagagaaaca aaatcaaaaa atatatgatt taacaacgaa actatcaata   1080

gctgatttac aaaaatcaat gcttcttctt acacaaaatg atttgcatac gtttgcaaat   1140

caagtagatg tagaactgga tctactaaag cgctataaag aagatttaaa tctaataaaa   1200

aatagcatta caaaattatc tactaatgtt gatacaacta acgagcagtc tcaaaaagat   1260

acattaagac aattaaaaaa tgtaataagt taccttgaag aacaagtata taaattttaa   1320
```

<210> SEQ ID NO 3
<211> LENGTH: 1344
<212> TYPE: DNA
<213> ORGANISM: Bacillus cereus

<400> SEQUENCE: 3

-continued

```
atgaaaacta aaataattac aggattatta gtcacatcca ttgtaactgg aggaaatatt     60
cctatcaata ctctcgcaac accaatcgtt caagcagaaa ctcaacagga aggcatggat    120
atttcctctt cattacgaaa attaggtgcg caatctaaat taatccaaac gtatattgat    180
caatctttaa tgagtcctaa tgtacagtta gaggaagtca cagctttaaa tacaaatcaa    240
ttcctaatca aacaagatat gaaggaatgg tcatcggaac tctatccaca gttaattcta    300
ttaaattcaa aaagcaaagg atttgtaaca aaatttaata gctattaccc gacattaaaa    360
tcgtttgtag acaataaaga agatagagaa gggttttcgg atagacttga agtacttcaa    420
gaaatggcta tgacgaatca agaaaatacg caacggcaaa tcaatgaatt aacagatctt    480
aaattacagc ttgataaaaa attaaaagat tttgatacca atgtggcaac tgcgcaaggc    540
atactaagta cagatggaac aggaaaaata gatcagttaa aaatgaaat attaaataca    600
aaaaaagcaa ttcaaaatga tttacagcaa attgcattaa taccaggggc tttaaatgaa    660
cagggatttg ctatattcaa agaagtttat agtctttcaa aagaaattat tgaaccagct    720
gcgcaagcag gggtggcagc atataacaaa ggaaaagaaa ttaacaactc tattctagaa    780
gctgagaaaa aagcagtgca agaagcaaca gagcaaggta aaacggctct agagattgaa    840
tcagcaaaaa aagcagctcg tgaagcaatt gagaaaagca aacaaggtga aatagcagcc    900
gcagccgcag caaaaacaca agagtatgac ctgatgaagg tcattgatac cgaaaagatt    960
aagaaaacat ttggcgtttt tgctgaagta aataaattaa cagcagaaca gcgagcatat   1020
ttagatgatt tagagaaaca aaatcaaaaa atatatgatt taacaacgaa attatcaata   1080
gctgatttac aaaaatcaat gcttcttctt acacaaaatg atttgcatac gtttgcaaat   1140
caaatagatg tagaacttga tctactaaag cgctataaag aagatttaaa tctaataaaa   1200
aatagcatta caaaattatc tactaatgtt gatacaacta gcgagcagtc tcaaaaagat   1260
acattaagac aattaaaaaa tgtaatagtt accttgaaga acaagtatat aaattttaat   1320
attgcgtttt ttaggaattc ataa                                          1344
```

<210> SEQ ID NO 4
<211> LENGTH: 1344
<212> TYPE: DNA
<213> ORGANISM: Bacillus cereus

<400> SEQUENCE: 4

```
atgaaaacta aaataatgac aggattttta ataacatcca ttgtaactgg agcaactatt     60
cctatcaata ctctcgcaac accaatcgtt caagcagaaa ctcaacaaga aaacatggat    120
atttcttcat cattacgaaa attaggtgcg caatctaaat taatccaaac gtatattgat    180
caatctttaa tgagtcctaa tgtacagcta gaggaagtcc cagctttaaa tacaaatcaa    240
ttcctaatca aacaagatat gaaggaatgg tcatcggaac tctatccaca gttaattcta    300
ttaaattcaa aaagtaaagg atttgtaaca aaatttaata gctattaccc gacattaaaa    360
tcgtttgtag acaataaaga agatagagaa gggttttcgg atagacttga agtacttcaa    420
gaaatggcta tgacgaatca agaaaatgcg caacgacaaa tcaatgaatt aacagaactt    480
aaattacagc ttgataaaaa attaaaagat tttgatacta atgtggcaac tgcgcaaggc    540
atattaggta cagatggaac aggaaaaata gatcagttaa aaatgaaat attaaatacc    600
aaaaaagcaa ttcaaaatga tttacaacaa attgcattaa tacctggagc tttaaatgag    660
cagggatttg ctatattcaa agaagtttat agtctttcaa aagaaattat tgaaccagct    720
gctcaagcag gggtggcagc gtataacaaa ggaaaagaaa ttaacaactc tattctagaa    780
```

-continued

```
gcggagaaaa aagcggcgca agaagcgaca gaacaaggta aaactgctct agagattgaa    840
tcagcaaaaa aagcagctcg tgaagcaatt gagaaaagca aacaaggtga aatagcagcc    900
gcagccgcag caaaaacaca agagtatgac ctgatgaaag ccattgatac cgaaaagatt    960
aagaaaacat ttggcgtttt tgctgaagta aataaattaa cagcagaaca gcgagcatat   1020
ttagatgatt tagagaaaca aaatcaaaaa atatatgatt taacaacgaa actatcaata   1080
gctgatttac aaaaatcaat gcttcttctt acacaaaatg atttgcatac gtttgcaaat   1140
caagtagatg tagaacttga tctactaaag cgctataaac aacatttaaa tctaataaaa   1200
aatagcatta caaaattatc tactaatgtt gatacaacta acgagcagtc tcaaaaagat   1260
acattaagac aattaaaaaa tgtaaaagtt accttgaaga acaagtgtat aaattttgat   1320
attgcgtttt ttggaaatct ataa                                          1344
```

<210> SEQ ID NO 5
<211> LENGTH: 1320
<212> TYPE: DNA
<213> ORGANISM: Bacillus cereus

<400> SEQUENCE: 5

```
atgaaaacta aaataatgac aggattatta gtcacatcca ttgtaactgg agcaactatt     60
cctatcaata ctctcgcaac accaatcgtt caagcggaaa ctcaacagga aggcatggat    120
atttcctctt cattacgaaa attaggtgcg caatctaaat taatccaaac gtatattgat    180
caatctttaa tgagtcctaa tgtacagcta gaggaagtcc cagctttaaa tacgaatcaa    240
ttcctaatca aacaagatat gaaggaatgg tcatcggaac tctatccaca gttaattcta    300
ttaaattcaa aaagtaaagg atttgtaaca aaatttaata gttattaccc gacattaaaa    360
tcgtttgtag acaataaaga agatagagaa gggttttcgg atagacttga agtacttcaa    420
gaaatggcta tgacgaatca agaaaatgcg caacgacaaa tcaatgaatt aacagatctt    480
aaattacagc ttgataaaaa attaaaagat tttgatacta atgtggcaac tgcgcaaggc    540
atactaagta cagatggaac aggaaaaata gatcagttaa aaaatgaaat attaaatacc    600
aaaaaagcaa ttcaaaatga tttacagcaa attgcattaa taccaggagc tttaaatgag    660
cagggatttg ctatattcaa agaagtttat agtctttcaa aagaaattat tgaaccagct    720
gctcaagcag gggtggcagc gtataacaaa ggaaaagaaa ttaacaactc tattctagaa    780
gcggagaaaa aagcggcgca agaagcgaca gaacaaggta aaactgctct agagattgaa    840
tcagcaaaaa aagcagctcg tgaagcaatt gagaaaagca aacaaggtga aatagcagcc    900
gcagccgcag caaaaacaca agagtatgac ctgatgaagg tcattgatac cgaaaagatt    960
aggaaaacat ttggcgtttt tgctgaagta aataaattaa cagcagaaca gcgagcatat   1020
ttagatgatt tagagaaaca aaatcaaaaa atatatgatt taacaacgaa attatcaata   1080
gctgatttac aaaaatcaat gcttcttctt acacaaaatg atttgcatac gtttgcaaat   1140
caagtagatg tagaacttga tctactaaag cgctataaag aagatttaaa tctaataaaa   1200
aatagcatta caaaattatc tactaatgtt gatacaacta acgagcagtc tcaaaaagat   1260
acattaagac aattaaaaaa tgtaataagt taccttgaag agcaagtata taaattttga   1320
```

<210> SEQ ID NO 6
<211> LENGTH: 1320
<212> TYPE: DNA
<213> ORGANISM: Bacillus thuringiensis

<400> SEQUENCE: 6
atgaaaacta aaataattac aggattatta gtcacatcca ttgtaactgg aggaaatatt 60
cctatcaata ctctcgcaac accaatcgtt caagcggaaa ctcaacagga aggcatggat 120
atttcctctt cattacgaaa attaggtgcg caatctaaat taattcaaac gtatattgat 180
caatctttaa tgagtcctaa tgtacagtta gaggaagtca cagctttaaa tacaaatcaa 240
ttcctaatca aacaagatat gaaggaatgg tcatcggaac tctatccaca gttaattcta 300
ttaaattcaa aaagtaaagg atttgtaaca aaatttaata gctattaccc gacattaaaa 360
tcgtttgtag acaataaaga agatagagaa gggttttcgg atagacttga agtacttcaa 420
gaaatggcta tgacgaatca agaaaatacg caacggcaaa tcaatgaatt aacagatctt 480
aaattacagc ttgataaaaa attaaaagat tttgatactg atgtggcaac tgcgcaaggc 540
atactaagta cagatggaac aggaaaaata gatcagttaa aaaatgaaat attaaatacc 600
aaaaaagcaa ttcaaaatga tttacagcaa attgcattaa taccaggggc tttaaatgaa 660
cagggatttg ctatattcaa agaagtttat agtctttcaa aagaaattat tgaaccagct 720
gctcaagcag gggtggcagc atataacaag ggaaaagaaa ttaacaactc tattctagaa 780
gcagagaaaa aagcagtgca agaagcaaca gagcaaggta aaactgctct agagattgaa 840
tcagcaaaaa aagcagctcg tgaagcaatt gagaaaagca agcaaggtga aatagcagcc 900
gcagccgcag ccaaaacaca agagtatgac ctgatgaagg tcattgatac cgaaaaaatt 960
aagaaaacat ttggcgtttt tgctgaagta aataaattaa cagcagaaca gcgagcatat 1020
ttagatgatt tagagaaaca aaatcaaaaa atatatgatt taacaacgaa attatcaata 1080
gctgatttac aaaaatcaat gcttcttctt acgcaaaatg atttgcatac gtttgcaaat 1140
caagtagatg tagaactgga tctactaaag cgctataaag aagatttaaa tctaataaaa 1200
aatagcatta caaaattatc tactaatgtt gatacaacta acgagcagtc tcaaaaagat 1260
acattaagac aattaaaaaa tgtaatgagt taccttgaag aacaagtaaa taaattttaa 1320

<210> SEQ ID NO 7
<211> LENGTH: 1221
<212> TYPE: DNA
<213> ORGANISM: Bacillus thuringiensis

<400> SEQUENCE: 7
atgaaaaaat ttccattcaa agtactaact ttagctacat tagcaactgt tataactgct 60
actaccggta acactattca tgcatttgca caagaaacga ccgctcaaga acaaaaagta 120
ggcaattatg cattaggccc cgaaggactg aagaaagcat tagctgaaac agggtctcat 180
attctagtaa tggatttata cgcaaaaaca atgattaagc aaccaaatgt aaatttatct 240
aatatcgatt taggctcaga ggggggagag ttgctcaaaa atattcacct taatcaagag 300
ctgtcacgaa tcaatgcgaa ttactggtta gatacagcga agccacagat tcaaaaaact 360
gctcgtaata ttgtaaatta cgatgaacaa tttcaaaatt attacgacac attagtagaa 420
actgtacaaa agaaagataa ggcaggtcta aaagagggta taaatgattt aattactaca 480
atcaatacaa attcaaaaga agttacagat gtgattaaga tgctacaaga cttcaaaggg 540
aaattatatc aaaattctac agattttaaa aataatgttg gtggtccaga tgggaaaggt 600
ggattaactg caatattagc aggtcaacag gcaacgattc cacaacttca agctgaaatt 660
gagcaacttc gttctactca gaaaaaacat tttgatgatg tattagcatg gtcaattggt 720
ggtggattgg gagcagctat tttagttatt gcagctattg gaggagcggt agttattgtt 780

-continued

```
gtaactggcg gtacagcaac accggctgtt gttggtggac tctcggctct tggcgcagct    840

ggtatcggtc taggaactgc ggctggtgtc acagcatcta agcatatgga ttcctataat    900

gaaatttcta acaaaatcgg agaattaagt atgaaagcag atcgtgctaa tcaagcagtt    960

ctttcgctta ctaacgcgaa agaaacattg gcatatttat accagactgt agatcaagcg   1020

atattgtctc taacaaatat tcaaaagcaa tggaatacaa tgggcgcaaa ttatacagat   1080

ttattggata atatcgattc tatgcaagac cacaaattct ctttaatacc agatgattta   1140

aaagcggcta aagaaagttg gaatgatatt cataaagatg cagaattcat ttcaaaagat   1200

attgctttta aacaggagta g                                             1221
```

```
<210> SEQ ID NO 8
<211> LENGTH: 1221
<212> TYPE: DNA
<213> ORGANISM: Bacillus cereus

<400> SEQUENCE: 8

atgaaaaaat ttccattcaa agtactaact ttagctacat tagcaactgt tataactgct     60

actaccggta acactattca tgcatttgca caagaaacga ccgctcaaga acaaaaagta    120

ggcaattatg cattaggacc cgaaggactg aagaaagcat tggctgaaac agggtctcat    180

attctagtaa tggatttata tgcaaaaaca atgattaagc aaccaaatgt aaatttatct    240

aatatcgatt tagggtcaga ggggggagag ttgctcaaaa atattcacct taatcaagag    300

ctgtcacgaa tcaatgcgaa ttactggtta gatacagcga agccacagat tcaaaaaact    360

gctcgtaata ttgtaaatta cgatgaacaa tttcaaaatt attacgacac attagtagaa    420

actgtacaaa agaaagataa ggcaggtcta aaagagggta taaatgattt aattactaca    480

atcaatacaa attcaaaaga agttacagat gtgattaaga tgctacaaga cttcaaagga    540

aaactatatc aaaattctac agattttaaa aataatgttg gtggtccaga tgggaaaggt    600

ggattaactg caatattagc aggtcaacag gcaacgattc cacaacttca agctgaaatt    660

gagcaacttc gttctactca gaaaaaacat tttgatgatg tattagcatg gtcaattggt    720

ggtggattgg gagcagctat tttagttatt gcagctattg gaggagcggt agttattgtt    780

gtaactggcg gtacagcaac accggctgtt gttggtggac tctcggctct tggtgcagct    840

ggtatcggtc taggaactgc ggctggtgtc acagcatcta agcatatgga ctcctataat    900

gaaatttcta acaaaatcgg agaattaagt atgaaagcag atcgtgctaa tcaagcagtt    960

ctttcactta ctaacgcgaa agaaacattg gcatatttat atcagactgt agatcaagcg   1020

atattgtctc taacaaatat tcaaaagcaa tggaatacaa tgggcgcaaa ttatacagat   1080

ttattggata atatcgattc tatgcaagac cacaaattct ctttaatacc agatgattta   1140

aaagccgcta aagaaagttg gaatgatatt cataaagatg cagaattcat ttcaaaagat   1200

attgctttta aacaggagta g                                             1221
```

```
<210> SEQ ID NO 9
<211> LENGTH: 1221
<212> TYPE: DNA
<213> ORGANISM: Bacillus cereus

<400> SEQUENCE: 9

atgaaaaaat ttccattcaa agtactaact ttagctacat tagcaactgt tataactgct     60

actaccggta acactattca tgcatttgca caagaaacga ccgctcaaga acaaaaagta    120
```

-continued

```
ggcaattatg cattaggccc cgaaggactg aagaaagcat tagctgaaac agggtctcat    180
attctagtaa tggatttata cgcaaaaaca atgattaagc aaccaaatgt aaatttatct    240
aatatcgatt taggctcaga gggggggagag ttgctcaaaa atattcacct taatcaagag    300
ctgtcacgaa tcaatgcgaa ttactggtta gatacagcga agccacagat tcaaaaaact    360
gctcgtaata ttgtaaatta cgatgaacaa tttcaaaatt attacgacac attagtagaa    420
actgtacaaa agaaagataa ggcaggtcta aaagagggta taaatgattt aattactaca    480
atcaatacaa attcaaaaga agttacagat gtgattaaga tgctacaaga cttcaaaggg    540
aaactatatc aaaattctac agattttaaa aataatgttg gtggtccaga tgggaaaggt    600
ggattaactg caatattagc aggtcaacag gcaacgattc cacaacttca agctgaaatt    660
gagcaacttc gttctactca gaaaaaacat tttgatgatg tattagcatg gtcaattggt    720
ggtggattgg gagcagctat tttagttatt gcagctattg gaggagcggt cgttattgtt    780
gtaactggcg gtacagcaac accggctgtt gttggtggac tctcggctct tggtgcagct    840
ggtattggtt taggaacagc ggctggtgtc acagcatcta agcatatgga ctcctataat    900
gaaatttcta acaaaatcgg agaattaagt atgaaagcag atcgtgctaa tcaagcagtt    960
ctttcgctta ctaacgcgaa agaaacattg gcatatttat atcagactgt agatcaagcg   1020
atattgtctc taacaaatat tcaaaagcaa tggaatacaa tgggcgcaaa ttatacagat   1080
ttactggata atatcgattc tatggaagac cacaaattct ctttaatacc agatgattta   1140
aaagccgcta aagaaagttg gaatgatatt cataaagatg cagaattcat ttcaaaagat   1200
attgctttta aacaggagta g                                             1221
```

<210> SEQ ID NO 10
<211> LENGTH: 1155
<212> TYPE: DNA
<213> ORGANISM: Bacillus cereus

<400> SEQUENCE: 10

```
atgaaaaaat ttccattcaa agtactaact ttagctacat tagcaactgt tataactgct     60
actaccggta acactattca tgcatttgca caagaaacga ccgctcaaga acaaaaagta    120
ggcaattatg cattaggccc cgaaggacta aagaaagcat tggctgaaac agggtctcat    180
attctagtaa tggatttata cgcaaaaaca atgattaagc aaccaaatgt aaatttatct    240
aatatcaatt taggctcaga gggggggagag ttgctcaaaa atattcacct taatcaagag    300
ctgtcacgaa tcaatgcgaa ttactggtta gatacagcga agccacagat tcaaaaaact    360
gctcgtaata ttgtaaatta cgatgaacaa tttcaaaatt attacgacac attagtagaa    420
actgtacaaa agaaagataa ggcaggtcta aaagagggca taaatgattt aattactaca    480
atcaatacaa attcaaaaga agttacagat gtgattaaga tgctacaaga cttcaaaggg    540
aaactatatc aaaattctac agattttaaa aataatgttg gtggtccaga tgggaaaggt    600
ggtttaactg caatattagc aggtcaacag gcaacgattc cacaacttca agctgaaatt    660
gagcaacttc gtgctactca gaaaaaacat tttgatgatg tattagcatg gtcaattggt    720
ggtggattgg gagcagctat tttagttatt gcagctattg gaggagcggt agttattgtt    780
gtaactggcg gtacagcaac accggctgtt gttggtggac tctcggctct tggtgcagct    840
ggtattggtt taggaacagc ggctggtgtc acagcatcta agcatatgga ctcctataat    900
gaaatatcta acaaaatcgg agaattaagt atgaaagcag atcgtgctaa tcaagcagtt    960
tcttttcgct ttactaacgc gaaagaaaca ttggcatatc tatatcagac tgtagatcaa   1020
```

-continued

```
gcgatattgt ctctaacaaa tattcaaaag caatggaata caatgggcgc aaattataca   1080

gatttactgg ataatatcga ttctatgcaa gaccacaaat tctctttaat accagatgaa   1140

tttaaaagcc gctaa                                                    1155
```

<210> SEQ ID NO 11
<211> LENGTH: 1062
<212> TYPE: DNA
<213> ORGANISM: Bacillus cereus

<400> SEQUENCE: 11

```
ttggctgaaa cagggtctca tattctagta atggatttat acgcaaaaac aatgattaag     60

caaccaaatg taaatttatc taatatcgat ttaggctcag aggggggaga gttgctcaaa    120

aatattcacc ttaatcaaga gctgtcacga atcaatgcga attactggtt agatacagcg    180

aagccacaga ttcaaaaaac tgctcgtaat attgtaaatt acgatgaaca atttcaaaat    240

tattacgaca cattagtaga aactgtacaa aagaaagata aggcaggtct aaaagagggc    300

ataaatgatt taattactac aatcaataca aattcaaaag aagttacaga tgtgattaag    360

atgctacaag acttcaaagg gaaactatat caaaattcta cagattttaa aaataatgtt    420

ggtggtccag atgggaaagg tggattaact gcaatattag caggtcaaca ggcaaccatt    480

ccacaacttc aagctgaaat tgagcaactt cgttctactc agaaaaaaca ttttgatgat    540

gtattagcat ggtcaattgg tggtggattg ggagcagcta ttttagttat tgcagctatt    600

ggaggagcgg tagttattgt tgtaactggc ggtacagcaa caccagctgt tgttggtgga    660

ctttcagctc ttggagcagc tggtatcggt ctaggaactg cggctggtgt tacagcatct    720

aagcatatgg actcctataa cgaaatttct aacaaaatcg gagaattaag tatgaaagca    780

gatcgtgcta atcaagcagt tctttcgctt actaacgcga aagaaacatt ggcatattta    840

tatcagactg tagatcaagc gatattgtct ctaacaaata ttcaaaagca atggaataca    900

atgggcgcaa attatacgga tttactggat aatatcgatt ctatgcaaga ccacaaattc    960

tctttaatac cagatgattt aaaagctgct aaacaaagtt ggaatgatat tcataaagat   1020

gcagaattca tttcaaaaga tattgctttt aaacaggagt ag                      1062
```

<210> SEQ ID NO 12
<211> LENGTH: 1221
<212> TYPE: DNA
<213> ORGANISM: Bacillus thuringiensis

<400> SEQUENCE: 12

```
atgaaaaaat ttccattcaa agtactaact ttagctacat tagcaactgt tataactgct     60

actaccggta acactattca tgcatttgca caagaaacaa ctgctcaaga acaaaaagta    120

ggcaattatg cattaggccc cgaaggactg aagaaagcat tggctgaaac agggtctcat    180

attctagtaa tggatttata cgcaaaaaca atgattaagc aaccaaatgt aaatttatct    240

aatatcgatt taggctcaga ggggggagag ttgctcaaaa atattcacct taatcaagag    300

ctgtcacgaa tcaatgcgaa ttactggtta gatacagcga agccacagat tcaaaaaact    360

gctcgtaata ttgtaaatta cgatgaacaa tttcaaaatt attacgacac attagtagaa    420

actgtacaaa agaaagataa ggcaggtcta aaagagggta taaatgattt aattactaca    480

atcaatacaa attcaaaaga agttacagat gtgattaaga tgctacaaga cttcaaaggg    540

aaactatatc aaaattctac agattttaaa aataatgttg gtggtccaga tgggaaaggt    600
```

```
ggattaactg caatattagc aggtcaacag gcaacgattc cacaacttca agctgaaatt    660

gagcaacttc gttctactca gaaaaaacat tttgatgatg tattagcatg gtcaattggt    720

ggtggattgg gagcagctat tttagttatt gcagctattg gaggagcggt agttattgtt    780

gtaactggcg gtacagcaac accggctgtt gttggtggac tctcggctct tggtgcagct    840

ggtatcggtc taggaactgc ggctggtgtc acagcatcta agcatatgga ctcctataat    900

gaaatttcta acaaaatcgg agaattaagt atgaaagcag atcgtgctaa tcaagcagtt    960

ctttcgctta ctaacgcgaa agaaacattg gcatatttat atcagactgt agatcaagcg   1020

atattgtctc taacaaatat tcaaaagcaa tggaatacaa tgggcgcaaa ttatacagat   1080

ttattggata atatcgattc tatgcaagac cacaaattct ctttaatacc agatgattta   1140

aaagccgcta aagaaagttg gaatgatatt cataaagatg cagaattcat ttcaaaagat   1200

attgctttta aacaggagta g                                             1221
```

<210> SEQ ID NO 13
<211> LENGTH: 972
<212> TYPE: DNA
<213> ORGANISM: Bacillus thuringiensis

<400> SEQUENCE: 13

```
atgataaaaa aaatccctta caaattactc gctgtatcga cactattaac tattacaact     60

gctaatgtag tttcaccagt aacaactttt gcaagtgaaa ttgaacaaac gaataatgga    120

gatacggctc tttctgcaaa tgaagcgaga atgaaagaga ccttgcaaaa ggctggatta    180

tttgcaaaat ctatgaatgc ctattcttat atgttaatta agaatcctga tgtgaatttt    240

gagggaatta ccattaatgg atatgtagat ttacctggta gaatcgtaca agatcaaaag    300

aatgcaaggg cacatgccgt tacttgggat acgaaagtaa aaaaacagct tttagataca    360

ttgaatggta ttgttgaata cgatacaaca tttgataatt attatgaaac aatgatagag    420

gcgattaata caggggatgg agaaacttta aaagaaggga ttacagattt acgaggtgaa    480

attcaacaaa atcaaaagta tgcacaacaa ctaatagaag aattaactaa attaagagac    540

tctattggac acgatgttag agcatttgga agtaataaag agctcttgca gtcaatttta    600

aaaaatcaag gtgcagatgt tgatgccgat caaaagcgtc tagaagaagt attaggatca    660

gtaaactatt ataaacaatt agaatctgat gggtttaatg taatgaaggg tgctattttg    720

ggtctaccaa taattggcgg tatcatagtg ggagtagcaa gggataattt aggtaagtta    780

gagcctttat tagcagaatt acgtcagacc gtggattata aagtaacctt aaatcgtgta    840

gttggagttg cttacagtaa tattaatgaa atgcacaagg cgcttgatga tgctattaac    900

gctcttactt atatgtccac gcagtggcat gatttagatt ctcaatattc gggcgttcta    960

gggcatattg ag                                                        972
```

<210> SEQ ID NO 14
<211> LENGTH: 1128
<212> TYPE: DNA
<213> ORGANISM: Bacillus cereus

<400> SEQUENCE: 14

```
atgataaaaa aaatccctta caaattactc gctgtatcga cgctattaac tattacaact     60

gctaatgtag tttcaccagt aacaactttt gcaagtgaaa ttgaacaaac gaacaatgga    120

gatacggctc tttctgcaaa tgaagcgaga atgaaagaga ccttgcaaaa ggctggatta    180

tttgcaaaat ctatgaatgc ctattcttat atgttaatta agaatcctga tgtgaatttt    240
```

-continued

```
gagggaatta ccattaatgg atatgtagat ttacctggta gaatcgtaca agatcaaaag    300

aatgcaaggg cacatgccgt tacttgggat acgaaagtaa aaaaacagct tttagataca    360

ttgaatggta ttgttgaata cgatacaaca tttgataatt attatgaaac aatgatagag    420

gcgattaata caggggatgg agaaacttta aaagaaggga ttacagattt acgaggtgaa    480

attcaacaaa atcaaaagta tgcacaacaa ctaatagaag aattaactaa attaagagac    540

tctattggac acgatgttag agcatttgga agtaataaag agctcttgca gtcaatttta    600

aaaaatcaag gtgcagatgt tgatgccgat caaaagcgtc tagaagaagt attaggatca    660

gtaaactatt ataaacaatt agaatctgat gggtttaatg taatgaaggg cgctattttg    720

ggtctaccaa taattggcgg tattatagtg ggagtagcaa gggataattt aggtaagtta    780

gagcctttat tagcagaatt acgtcagacc gtggattata aagtaacctt aaatcgtgtg    840

gttggagttg cttacagtaa tattaatgaa atgcacaagg cccttgatga tgctattaac    900

gctcttactt atatgtccac gcagtggcat gatttagatt ctcaatattc gggcgttcta    960

gggcatattg agaatgcagc tcaaaaagcc gatcaaaata aatttaaatt cttaaaacct   1020

aatttaaatg cagcgaaaga cagttggaaa acattacgaa cagatgctgt tacattaaaa   1080

gaaggaataa aggaattaaa agtggaaact gttactccac aaaaatag                1128
```

```
<210> SEQ ID NO 15
<211> LENGTH: 1128
<212> TYPE: DNA
<213> ORGANISM: Bacillus cereus

<400> SEQUENCE: 15

atgataaaaa aaatccctta taaattactc gctgtatcga cgctattaac tattacaact     60

gctaatgtag tttcaccagt aacaactttt gcaagtgaaa ttgaacaaac gaacaatgga    120

gatacggctc tttctgcaaa tgaagcgaga atgaaagaga ccttgcaaaa ggctggatta    180

tttgcaaaat ctatgaatgc ctattcttat atgttaatta agaatcctga tgtgaatttt    240

gagggaatta ccattaatgg atatgtagat ttacctggta gaatcgtaca agatcaaaag    300

aatgcaaggg cacatgctgt tacttgggat acgaaagtaa aaaaacagct tttagataca    360

ttgaatggta ttgttgaata cgatacaaca tttgacaatt attatgaaac aatggtagaa    420

gcgattaata caggggatgg agaaacttta aaagaaggga ttacagattt gcgaggtgaa    480

attcaacaaa atcaaaagta tgcacaacaa ctaatagaag aattaactaa attaagagac    540

tctattggac atgatgttag agcttttgga agtaataaag agctcttgca gtcaatttta    600

aaaaatcaag gtgcagatgt tgatgccgat caaaagcgtc tagaagaagt attaggatca    660

gtaaactatt ataaacaatt agaatctgat gggtttaatg taatgaaggg tgctattttg    720

ggtctaccaa taattggcgg tattatagtc ggagtagcaa gggataattt aggtaagtta    780

gagcctttat tagcagaatt acgtcagacc gtggattata aagtaacctt aaatcgtgta    840

gttggagttg cttacagtaa tattaatgaa atgcacaagg cgcttgatga tgctattaac    900

gctcttactt atatgtccac gcagtggcat gatttagatt ctcaatattc gggcgttcta    960

gggcatattg agaatgcagc tcaaaaagcc gatcaaaata aatttaaatt cttaaagcct   1020

aatttaaatg cagcgaaaga cagttggaaa acattacgaa cagatgctgt tacattaaaa   1080

gaaggaataa aggaattaaa agtggaaact gttactccac aaaaatag                1128

<210> SEQ ID NO 16
```

-continued

<211> LENGTH: 1128
<212> TYPE: DNA
<213> ORGANISM: Bacillus cereus

<400> SEQUENCE: 16

```
atgataaaaa aaatccctta caaattactc gctgtatcga cgttattaac tattacaacc      60
gctaatgtag tttcacctgt agcaactttt gcaagtgaaa ttgaacaaac gaacaatgga     120
gatacggctc tttctgcaaa tgaagcgaag atgaaagaaa ctttgcaaaa ggctggatta     180
tttgcaaaat ctatgaatgc ctattcttat atgttaatta aaaatcctga tgtgaatttt     240
gagggaatta ctattaatgg atatgtagat ttacctggta gaatcgtaca agatcaaaag     300
aatgcaagag cacatgctgt tacttgggat acgaaagtga aaaaacagct tttagataca     360
ttgactggta ttgttgaata tgatacgacg tttgacaatt attatgaaac aatggtagag     420
gcaattaata caggggatgg agaaacttta aaagaaggga ttacagattt gcgaggtgaa     480
attcaacaaa atcaaaagta tgcacaacaa ctaatagaag aattaactaa attaagagac     540
tctattggac acgatgttag agcatttgga agtaataaag agctcttgca gtcaatttta     600
aaaaatcaag gtgcagatgt tgatgccgat caaaagcgtc tagaagaagt attaggatca     660
gtaaactatt ataaacaatt agaatctgat gggtttaatg taatgaaggg tgctattttg     720
ggtctaccaa taattggcgg tattatagtg ggagtagcaa gggataattt aggtaagtta     780
gagcctttat tagcagaatt acgtcagacc gtggattata aagtaacctt aaatcgtgta     840
gttggagttg cttacagtaa tattaatgaa atcgacaagg cgcttgatga tgctattaac     900
gctcttactt atatgtccac gcagtggcat gatttagatt ctcaatattc gggcgttcta     960
gggcatattg agaatgcagc tcaaaaagcc gatcaaaata aatttaaatt cttaaaacct    1020
aatttaaatg cagcgaaaga tagttggaaa acattacgaa cagatgctgt tacattaaaa    1080
gaaggaataa aggagttaaa agtagaaact gttactccac aaaaatag                 1128
```

<210> SEQ ID NO 17
<211> LENGTH: 1128
<212> TYPE: DNA
<213> ORGANISM: Bacillus cereus

<400> SEQUENCE: 17

```
atgataaaaa aaatccctta caaattactc gctgtatcga cgttattaac tattacaact      60
gctaatgtag tttcaccagt aacaactttt gcaagtgaaa ttgaacaaac gaacaatgaa     120
gatacagctc tttctgcaaa tgaagcgaga atgaaagaga ccttgcaaaa ggctggatta     180
tttgcaaaat ctatgaatgc ctattcttat atgttaatta agaatcctga tgtgaatttt     240
gagggaatta cgattaatgg gtatgtagat ttacctggta gaatcgtaca agatcaaaag     300
aatgcaaggg cacatgctgt tacttgggat acgaaagtaa aaaaacagct tttagataca     360
ttgaatggta ttgttgaata cgatacaaca tttgacaatt attatgaaac aatggtagag     420
gcgattaata caggggatgg agaaacttta aaagaaggga ttacagattt gcgaggtgaa     480
attcaacaaa atcaaaagta tgcacaacaa ctaatagaag aattaactaa attaagagac     540
tctattggac acgatgtgag agcatttgga agtaataaag agctcttgca gtcaatttta     600
aaaaatcaag gtgcagatgt tgatgccgat caaaagcgtc tagaagaagt attaggatca     660
gtaaactatt ataaacaatt agaatctgat gggtttaatg taatgaaggg tgctattttg     720
ggtctaccaa taattggcgg tatcatagtg ggagtagcaa gggataattt aggtaagtta     780
gagcctttat tagcagaatt acgtcagacc gtggattata aagtaacctt aaatcgtgta     840
```

```
gttggagttg cttacagtaa tattaatgaa atgcacaagg cgcttgatga tgctattaac    900

gctcttactt atatgtccac gcagtggcat gatttagatt ctcaatattc gggcgttcta    960

gggcatattg agaatgcagc tcaaaaagcc gatcaaaata aatttaaatt cttaaaacct   1020

aatttaaatg cagcgaaaga cagttggaaa acattacgaa cagatgctgt tacattaaaa   1080

gaaggaataa aggaattaaa agtggaaact gttactccac aaaaatag                1128


<210> SEQ ID NO 18
<211> LENGTH: 1128
<212> TYPE: DNA
<213> ORGANISM: Bacillus thuringiensis

<400> SEQUENCE: 18

atgataaaaa aaatccctta caaattactc gctgtatcga cgctattaac tattacaact     60

gctaatgtag tttcaccagt aacaactttt gcaagtgaaa ttgaacaaac gaacaatgaa    120

gattcagctc tttctgcaaa tgaagcgaga atgaaagaga ccttgcaaaa ggctggatta    180

tttgcaaaat ctatgaatgc ctattcttat atgttaatta aaaatccgga tgtgaatttt    240

gagggaatta ccattaatgg atatgtagat ttacctggta gaatcgtaca agatcaaaag    300

aatgcaagag cacatgctgt tacttgggat acgaaagtaa aaaaacagct tttagataca    360

ttgaatggta ttgttgaata cgatacaaca tttgacaatt attatgaaac aatggtagag    420

gcgattaata caggggatgg agaaacttta aaagaaggga ttacagattt gcgaggtgaa    480

attcaacaaa atcaaaagta tgcacaacaa ctaatagaag aattaactaa attaagagac    540

tctattggac acgatgttag agcatttgga agtaataaag agctcttgca gtcaatttta    600

aaaaatcaag gtgcagatgt tgatgccgat caaaagcgtc tagaagaagt attaggatca    660

gtaaactatt ataaacaatt agaatctgat gggtttaatg taatgaaggg tgctattttg    720

ggtctaccaa taattggcgg tatcatagtg ggagtagcaa gagataattt aggtaagtta    780

gagcctttat tagcagaatt acgtcagacc gtggattata aagtaacctt aaatcgtgta    840

gttggagttg cttacagtaa tattaatgaa atgcacaagg cacttgatga tgctattaac    900

gctcttactt atatgtccac gcagtggcat gatttagatt ctcaatattc gggcgttcta    960

gggcatattg agaatgcagc tcaaaaagcc gatcaaaata aatttaaatt cttaaaacct   1020

aatttaaatg cagcgaaaga cagttggaaa acattacgaa cagatgctgt tacattaaaa   1080

gaaggaataa aggagttaaa agtagaaact gttactccac aaaaatag                1128


<210> SEQ ID NO 19
<211> LENGTH: 1084
<212> TYPE: DNA
<213> ORGANISM: Bacillus thuringiensis

<400> SEQUENCE: 19

actcatttct attaaacaag atatgaaaga gtggtcatcc gaactttatc ctaaattaat     60

tctattaaat tcaaaaagta aaggatttgt aactaaattt aatagttatt atccaacatt    120

aaaaggattt gtagataata aggaagataa agaagggttt acagatagac tggaagtcct    180

tcaagacatg accatcacaa accaagaaag tgtgcaacgt caaattaatg agttaacaga    240

tctaaaacta caggtagata agaagttgaa aaatcttgat actgatgtgg caaaaacaca    300

gagtgtcctt aattcagagg gaacaggaaa aatagataag ttaaaaaatg aaatgctaga    360

tacaaaaaaa tcaattcaaa atgatttaca gcaaatagcg ttattaccag gagctttaaa    420
```

-continued tgaacaagga ctaaaggtat tccaagaaat ttatagtcta tcaaaagata tcattgaacc 480
ggctgctcaa acagcagtag tagcgtataa caaaggaaaa gaaataaaca atgctattgt 540
agacgcagag aataaagcag agcaagaagc aaaagaaaaa ggaaaatcag ctatagaaat 600
tgaggctgcc aaaaaagaag cacgtgaagc gatagagaaa agtaaaaaag gtgaaatcgc 660
tgcagctgca gttacaaaaa cgaaagagta tgatcttatg aaagtaattg atcctgaaaa 720
aattaaaaaa acatataata cttttgctga aattaataaa ctaacagcag agcaacgtgc 780
atatttaaat gatttagaga aacaaaatca gaaattatat gacttaacga ctaaattaac 840
agtagcagat ttacaaaaat caatgattct tttcatgcaa aatgatttgc atacatttgc 900
taaccaagta gatggagaaa ttgagctaat gaaacgttac aaagaggatt tggatctaat 960
aaataatagt attacaaaat tatcgactga agttgatacc aataacaccc agtctcaaaa 1020
agatacatta agacgattaa aaagtgtaac aactcaactc gaagaacaag tttataaatt 1080
ttaa 1084

<210> SEQ ID NO 20
<211> LENGTH: 1078
<212> TYPE: DNA
<213> ORGANISM: Bacillus thuringiensis

<400> SEQUENCE: 20
tctaattaaa caagatatga aagagtggtc atccgaactt taccctaaat taattctatt 60
aaattcaaaa agtaaaggat ttataactaa atttaatagt tattatccaa cattaaaagg 120
atttgtagat aataaggaag ataaagaagg gtttacagat agactggaag ttcttcaaga 180
catgactata acaaatcaag aaagtgtgca acgtcaaatt aatgagttaa cagatttaaa 240
attactggta gataagaagt tgaaaaacct tgatactgat gtggtaaaag cacaaagtgt 300
ccttaattca gagggaacag gaaaaataga taagttaaaa aatgaaatgc tagatacaaa 360
aaaatctatt caaaatgatt tgcagcaaat agcattatta ccaggcgcgt taaatgaaca 420
agggctaaag gtattccaag aaatttatag tctatcgaaa gatatcattg aaccggctgc 480
tcaaacagca gtagtagcgt ataacaaagg aaaagaaata aacaatgcca ttgtagacgc 540
agagaagaaa gcagagcaag aagcaaaaga aaagggaaaa tcagctatag aaattgaagc 600
tgccaaaaaa gaagcacgtg aaacgataga gaaaagtaaa aaaggtgaaa tcgctgcagc 660
tgcagttaca aaaacgaaag agtatgatct tatgaaagtg attgatcctg aaaaaataaa 720
aaaaacatat aatacttttg ctgaaattaa taaactaaca gctgagcaaa gagcatattt 780
aaatgattta gagaaacaaa atcagaaatt atatgactta acaactaaat taacagtagc 840
agatttacaa aaatcaatga ttcttttcat gcaaaatgac ttgcatacat ttactaatca 900
agtagatgga gaaattgagt taatgaaacg ttacaaagag gatttggatc taataaataa 960
tagtattaca aaattatcga ctgaagttga taccaataat actcaggctc aaaaagatat 1020
attaagacga ttaaaaagtg taacaattca acttgaagaa caagtttata aattttga 1078

<210> SEQ ID NO 21
<211> LENGTH: 1320
<212> TYPE: DNA
<213> ORGANISM: Bacillus cereus

<400> SEQUENCE: 21
atgaagaata aaattatgac aggattttta ataacatcaa ttgctaccgg ggcgactatt 60
cctatcaata ctctcgcaac gccaatcgtc caagcagaaa caaaacaaga gaatatagat 120

-continued

```
atttcctcag cgttacgaaa aataggtgca cactccaaat taacacaaac ctttatcgat    180
ggagccttag caagtccgaa tgtacaactt gaagaagttc catctttaaa tacaactcaa    240
tttctaatta aacaagatat gaaagagtgg tcatccgaac tttatcctaa attaattcta    300
ttaaattcaa aaagtaaagg atttgtaact aaatttaata gttattatcc aatattaaaa    360
gggtttatag ataataggga agataaagaa ggatttacag atagactgga agtccttcaa    420
gacatgacca tcacaaacca agaaagtgtg caacgtcaaa ttaatgagtt aacagatcta    480
aaactacagg tagataagaa gttgaaaaat cttgatactg atgtgacaaa agcacagagt    540
gtccttaatt cagagggaac aggaaaaata gataagttaa aaatgaaat gctagataca    600 aaaaaatcaa ttcaaaatga tttacagcaa attgcattat taccaggggc tttaaatgaa    660
caagggctaa aggtattcca agaaatttat agtctatcga aagatatcat tgaaccggct    720
gctcaaacag cagtagtagc gtataacaaa ggaaaagaaa taaacaatgc tattgtagac    780
gcagagaata aagcagagca agaagcaaaa gaaaagggaa aatcagctat agaaattgag    840
gctgcaaaaa aagaagcacg tgaagcgata gagaaaagta aaaaaggtga aatcgctgca    900
gctgcagtta caaaaacgaa agagtatgat cttatgaaag tgattgatcc tgaaaaaatt    960
aaaaaaacat ataatacttt tgctgaaatt aataaactaa cagcagagca acgtgcatat   1020
ttaaatgatt tagaaaaaca aaatcagaaa ttatatgact taacaactaa attaacagta   1080
gcagatttac aaaaatcaat gattcttttc atgcaaaatg atttgcatac atttgctaac   1140
caagtagatg gagaaattga gctaatgaaa cgttacaaag aggatttgga tctaataaat   1200
aatagtatta caaaattatc gactgaagtt gataccaata acactcagtc tcaaaaagat   1260
acattaagac gattaaaaag tgtaacaact caactcgaag aacaagttta taaattctaa   1320
```

<210> SEQ ID NO 22
<211> LENGTH: 1319
<212> TYPE: DNA
<213> ORGANISM: Bacillus cereus

<400> SEQUENCE: 22

```
atgaagaata aaattatgac aggattttta ataacatcaa ttgctaccgg ggcgactatt     60
cctatcaata ctctcgcaac gccaatcgtc caagcagaaa caaaacaaga gaatatagat    120
atttcctcag cgttacgaaa aataggtgca cactccaaat taacacaaac ctttatcgat    180
ggagccttag caagtccgaa tgtacaactt gaagaagttc catctttaaa tacaactcaa    240
tttctattaa acaagatatg aaagagtggt catccgaact ttatcctaaa ttaattctat    300
taaattcaaa aagtaaagga tttgtaacta aatttaatag ttattatcca atattaaaag    360
ggtttataga taatagggaa gataaagaag gatttacaga tagactggaa gtccttcaag    420
acatgaccat cacaaaccaa gaaagtgtgc aacgtcaaat taatgagtta acagatctaa    480
aactacaggt agataagaag ttgaaaaatc ttgatactga tgtgacaaaa gcacagagtg    540
tccttaattc agagggaaca ggaaaaatag ataagttaaa aaatgaaatg ctagatacaa    600
aaaaatcaat tcaaaatgat ttacagcaaa ttgcattatt accaggggct ttaaatgaac    660
aagggctaaa ggtattccaa gaaatttata gtctatcgaa agatatcatt gaaccggctg    720
ctcaaacagc agtagtagcg tataacaaag gaaaagaaat aaacaatgct attgtagacg    780
cagagaataa agcagagcaa gaagcaaaag aaaagggaaa atcagctata gaaattgagg    840
ctgcaaaaaa agaagcacgt gaagcgatag agaaaagtaa aaaaggtgaa atcgctgcag    900
```

-continued ctgcagttac aaaaacgaaa gagtatgatc ttatgaaagt gattgatcct gaaaaaatta 960
aaaaaacata taatactttt gctgaaatta ataaactaac agcagagcaa cgtgcatatt 1020
taaatgattt agaaaaacaa aatcagaaat tatatgactt aacaactaaa ttaacagtag 1080
cagatttaca aaaatcaatg attcttttca tgcaaaatga tttgcataca tttgctaacc 1140
aagtagatgg agaaattgag ctaatgaaac gttacaaaga ggatttggat ctaataaata 1200
atagtattac aaaattatcg actgaagttg ataccaataa cactcagtct caaaaagata 1260
cattaagacg attaaaaagt gtaacaactc aactcgaaga acaagtttat aaattctaa 1319

<210> SEQ ID NO 23
<211> LENGTH: 1323
<212> TYPE: DNA
<213> ORGANISM: Bacillus cereus

<400> SEQUENCE: 23
atgaaaaatg atctcactaa aaaatttgta ataacatcag ttgtttttgg attagcaatt 60
tctaactatg tattttcacc tgctatagtc atacaagctg agacacaaca agaacgaata 120
gatatttctt catccttacg caagttaggt gcacaatcta aactaataca aacatatatc 180
gatcaaaatt taataacacc taatatacag ttgaaggaaa tgccatcttt aaatacgaat 240
caatttttaa ttaagcgaga tatgaaagag tggtcatcag aactacatcc aaatttaatc 300
ctactaaatt caaatagtaa aggatatgta actaaattta ataactatta tccaacatta 360
aagggatttg tagataataa ggaagataaa gaaggctttt tagatagact ggaagtactt 420
caagatatga ctataagaaa ccaagaaagt gtccagcatc aaattaatga attaacagat 480
tttaaattac aactagataa aaagcttaaa gatctcgaca ctgatgtggc aaaggcacaa 540
gggttactag tttctgagaa aacagcaaaa atagatcttg ttaaaaatga attgctgatt 600
acaaaaaaag caattcaaag taatttacag gaaatagcat tattaccagg agctttaaat 660
gaacaagggc taaaggtatt ccaagaaatt tatagtctat cgaaagatat cattgaacca 720
tctgctcaaa cagcagtagt agcgtataac aaaggaaaag aaataaacaa tgctattgtc 780
gaagcagaga agaaagcaga gcaagaggca agggagaaag gtaaatcaat tctagaaatt 840
gaagccgcaa aaaaagaagc acgtgaagaa atttcgaaaa gtaaaaaagg tgaaattgct 900
gcagctgcgg ttacaaaaac aaaagagtat gatcttatga aatagttaa ttctgaaaaa 960 attaaaaaaa catatagtac cttcgccgaa attaataaac taacggcaga acagcgagcg 1020
catttatatg atttagagaa acaaaaccaa aaattatatg atttaacaag aaaattaaca 1080
gtagcaggat tacaaaaatc aatgattatt cttatgcaaa atgatttgca tacatttgtt 1140
agccaagtag atagagaaat tgatcttcag aaacgttata aagaagattt aaacctatta 1200
aaaaagagta ttacaacatt attgacaaat gttgatagtg taaacaataa gtctcaaaaa 1260
gatactttaa gaatattgaa aacattaacc ggtcaacttg aggaacaggt taataaattt 1320
taa 1323

<210> SEQ ID NO 24
<211> LENGTH: 1320
<212> TYPE: DNA
<213> ORGANISM: Bacillus weihenstephanensis

<400> SEQUENCE: 24
atgaagaata aaattatgac aggattttta ataacatcaa tcgttactgg agcgactatt 60
cctatcaata ctctcgcaac gccaatcgtt caggcagaaa tgaaacaaga aaatatagat 120

```
atttcctcag cattacgaaa aataggtgca cactccaaat taacacaaac ctttatagat    180
ggagccttag caagtccgaa tgtgcaactt gaagaagttc catctttaaa tacaactcaa    240
tttctaatta aacaagatat gaaagagtgg tcatcagaac tatatccaaa attaattcta    300
ctaaattcaa aaagtaaagg atttgcaacc aaatttaata gctattatcc aacattaaaa    360
ggatttgtag ataataagga agataaagaa gggtttatag atagactgga agttctccaa    420
gatatgacta taacaaacca agaaaacgtg caacgtcaga ttaatgagtt aacagatctt    480
aaactacagg tagataagaa actgaaaaat cttgatacag atgtggtaaa agcacagagt    540
gtacttagtt cagagggaac aggaaaaata gacaagttaa aaaatgaaat gctaaataca    600
aaaaaatcaa ttcaaaatgc tttagagcaa atagcattat taccaggagc tttaaatgaa    660
caagggctaa aggtattcca agaaatttat agcctatcaa aagatatcat tgaaccggct    720
gctcaaacag cggtagtagc gtataacaaa ggaaaagaaa taaataatac tattgtagaa    780
gcagagaaga aagcagagca ggaagcaaca gaaaagggaa aatcagctat agaaattgaa    840
gctgcaaaaa aagaagcacg tgaagcgata gagaaaagta aaaaaggtga gattgctgca    900
gctgcagtta caaaaacgaa agagtatgat cttatgaaag tgattgatcc tgaaaaaatt    960
aaaaaaacat atagtacctt tgccgaaatt aataaactaa cagcagagca aagagtatat   1020
ttaaatgatt tagagaaaca aaatcagaaa ttatatgact taacaactaa attaacagta   1080
gcagatctac aaaaatcaat gattcttttc atgcaaaatg atttgcatac atttgctaat   1140
caagtagatg gagaaattga gctaatgaaa cgttataaag aggatttgaa tctaataaat   1200
aatagtatta aaaaattatt gactgaagtt gatactagta acactcagtc tcaaaaagat   1260
acattaagac gactaaaaaa tgtaacaaat caactcgaag aacaagtcca taaattttaa   1320
```

<210> SEQ ID NO 25
<211> LENGTH: 1230
<212> TYPE: DNA
<213> ORGANISM: Bacillus thuringiensis

<400> SEQUENCE: 25

```
atgatgaaat ttccatttaa ggttataact ttagccactt tagcaacggt tataactgct     60
acgaatggta gtactattca tgcacttgca caagaacaga cagctcaaga acataaaata    120
gaaaattatg cgttaggacc tgaagggtta aagaaagcgt tggctgcaac tggctctcat    180
attcttgtaa tggatttgta cgcaaaaact atgattaagc aaccgaatgt aaatttatcc    240
aacattgatt taggttcagg aggaggagaa ttaatcaaaa atatccacct gaatcaggaa    300
ctgtcacgaa tcaatgcaaa ttactggtta gatacagcga agccaaacat tcaaaaaaca    360
gctcgtaata ttgtaaatta tgatgagcaa ttccaaaatt attacgacac attagtagat    420
actgtaaaaa agaaagataa gatgagcctt aaagaaggaa taggggattt aatcgataca    480
attcatacaa attcaaatga agttactgac gtcattaaga tgttagaggc tttcaaaaca    540
aagttgtata caaatactgt agattttaaa aataatgttg gtggtccaga tggacaggga    600
ggattgacgg ctatattagc gggaaaacaa gcactagtcc cacaacttca ggccgaaatt    660
gagaatttac gttctacaca gaaatcacat tttgataatg tattagcctg gtcaattggc    720
ggtggactag gagcagctat tttagttatt ggaacgattg caggagcggt agtaattgtt    780
gtgactggtg gtacagctac accagctgtt gttggcggtc ttacagctct aggagcagct    840
ggtatcggtt taggaacagc agctggtgtc gaggcatcta atcatatgaa ttcttataat    900
```

-continued gaaatttcga ataaaatcgg agaattaagt atgaaagctg atctggctaa tcaagcggtt 960
atttcactta ctaatacgaa agacactcta acatatttgt atcagacagt ggatcaagca 1020
ataatgtctc taacaagtat tcagcaacaa tggaataaaa tgggggctaa ttataaagat 1080
ttatatgata atatcgatca aatgcaagaa cataaacttt cgttaatacc tgacgattta 1140
aaagctgcta aacaaagttg gaatgacatt cataaggacg cagaattcat ttcaaaagac 1200
attgctttta aacaagaaaa aacaaactaa 1230

<210> SEQ ID NO 26
<211> LENGTH: 1230
<212> TYPE: DNA
<213> ORGANISM: Bacillus thuringiensis

<400> SEQUENCE: 26
atgatgaaat ttccatttaa agttataacc ttagctactt tagcaacgat tataaccgct 60
acaaatggta gtactattca tgcacttgca caagaacaga cagctcaaga acagaaaata 120
gaaaattatg cgttaggacc tgaaggatta aagaaagcgt tggctgaaac aggctctcat 180
attcttgtaa tggatttgta cgcaaaaact atgattaagc aaccgaatgt aaatttatcc 240
aacattgatt taggttcggg tggagaagaa ttaatcaaaa atattcacct gaatcaagaa 300
ctgtcacgaa tcaatgcaaa ttactggtta gatacagcga agccaaacat tcaaaaaaca 360
gcacgtaata ttgtaaatta tgatgagcaa tttcaaaatt attacgacac attagtagat 420
actgtaaaaa agaaggataa ggtgagcctc aaagaaggaa taggggattt aatctataca 480
attcatacaa attcaaatga agttacggaa gtcattaaga tgttagaggc tttcaaaaca 540
aagttgtata caaatactgt agattttaaa aataatgttg gtggtccaga tggacaggga 600
ggattgacgg ctatattagc gggaaaacaa gcgctagtcc cacaacttca ggccgaaatt 660
gagaatttac gttctacaca gaaaacacat tttgataatg tattagcctg gtcaattggt 720
ggtggattag gagcagctat tttagttatt ggaacgattg caggagcggt agtaattgtt 780
gtgactggtg gtacagctac gccagctgtt gttggtggtc ttacagctct aggagccgct 840
ggtatcggtt taggaacagc agctggcgtc gaggcatcta atcatatgaa ttcttataat 900
gaaatttcga ataaaatcgg agaattaagt atgaaagctg atttggctaa tcaagcggtt 960
atttcactta ctaatacgaa agacactcta acatatttgt atcagacagt ggatcaagca 1020
ataatgtctc taacaagtat tcagcaacaa tggaataaaa tgggggctaa ttataaagat 1080
ttatatgata atatcgatca aatgcaagaa cataaacttt cgttaatacc tgacgattta 1140
aaagctgcta aacaaagttg gaatgatatt cataaggatg cagaattcat ttcaaaagac 1200
attgctttta aacaagaaaa aacaaactag 1230

<210> SEQ ID NO 27
<211> LENGTH: 1215
<212> TYPE: DNA
<213> ORGANISM: Bacillus cereus

<400> SEQUENCE: 27
atgatgaaat ttccatttaa ggtcataact ttagccactt tagcaacggt tataactgct 60
acgaatggta gtactattca tgcacttgca caagaacaga aaatagaaaa ttatgcgtta 120
ggacctgaag gattaaagaa agcgttggct gcaactggct ctcatattct tgtaatggat 180
ttgtacgcaa aaactatgat taagcaaccg aatgtaaatt tatccaacat tgatttaggt 240
tcaggaggag gagaattaat caaaaatatc cacctgaatc aggaactgtc acgaatcaat 300
gcaaattact ggttagatac agcgaagcca aacattcaaa aaacagctcg taatattgta 360
aattatgatg agcaatttca aaattattac gacacattag tagatactgt aaaaaagaaa 420
gataagatga gccttaaaga aggaataggg gatttaatcg atacaattca tacaaattca 480
aatgaagtta ctgacgtcat taagatgtta gaggctttca aaacaaagtt gtatacaaat 540
actgtagatt ttaaaaataa tgttggtggt ccagatggac agggaggatt gacagctata 600
ttagcgggaa aacaagcact agtcccacaa cttcaggccg aaattgagaa tttacgttct 660
acacagaaat cacattttga taatgtatta gcctggttaa ttggcggtgg actaggagca 720
gctattttag ttattggaac gattgcagga gcggtagtaa ttgttgtgac tggtggtaca 780
gctacaccag ctgttgttgg cggtcttaca gctctaggag cagctggtat cggtttagga 840
acagcagctg gtgtcgaggc atctaatcat atgaattctt ataatgaaat ttcgaataaa 900
atcggagaat taagtatgaa agctgatctg gctaatcaag cggttatttc acttactaat 960
acgaaagaca ctctaacata tttgtatcag acagtggatc aagcaataat gtctctaaca 1020
agtattcagc aacaatggaa taaaatgggg gctaattata aagatttata tgataatatc 1080
gatcaaatgc aagaacataa actttcgtta atacctgacg atttaaaagc tgctaaacaa 1140
agttggaatg atattcataa ggacgcagaa ttcatttcga aagacattgc ttttaaacaa 1200
gaaaaaacaa actaa 1215

<210> SEQ ID NO 28
<211> LENGTH: 1215
<212> TYPE: DNA
<213> ORGANISM: Bacillus cereus

<400> SEQUENCE: 28
atgatgaaat ttccatttaa ggtcataact ttagccactt tagcaacggt tataactgct 60
acgaatggta gtactattca tgcacttgca caagaacaga aaatagaaaa ttatgcgtta 120
ggacctgaag gattaaagaa agcgttggct gcaactggct ctcatattct tgtaatggat 180
ttgtacgcaa aaactatgat taagcaaccg aatgtaaatt tatccaacat tgatttaggt 240
tcaggaggag gagaattaat caaaaaatatc cacctgaatc aggaactgtc acgaatcaat 300
gcaaattact ggttagatac agcgaagcca aacattcaaa aaacagctcg taatattgta 360
aattatgatg agcaatttca aaattattac gacacattag tagatactgt aaaaaagaaa 420
gataagatga gccttaaaga aggaataggg gatttaatcg atacaattca tacaaattca 480
aatgaagtta ctgacgtcat taagatgtta gaggctttca aaacaaagtt gtatacaaat 540
actgtagatt ttaaaaataa tgttggtggt ccagatggac agggaggatt gacagctata 600
ttagcgggaa aacaagcact agtcccacaa cttcaggccg aaattgagaa tttacgttct 660
acacagaaat cacattttga taatgtatta gcctggttaa ttggcggtgg actaggagca 720
gctattttag ttattggaac gattgcagga gcggtagtaa ttgttgtgac tggtggtaca 780
gctacaccag ctgttgttgg cggtcttaca gctctaggag cagctggtat cggtttagga 840
acagcagctg gtgtcgaggc atctaatcat atgaattctt ataatgaaat ttcgaataaa 900
atcggagaat taagtatgaa agctgatctg gctaatcaag cggttatttc acttactaat 960
acgaaagaca ctctaacata tttgtatcag acagtggatc aagcaataat gtctctaaca 1020
agtattcagc aacaatggaa taaaatgggg gctaattata aagatttata tgataatatc 1080
gatcaaatgc aagaacataa actttcgtta atacctgacg atttaaaagc tgctaaacaa 1140

-continued agttggaatg atattcataa ggacgcagaa ttcatttcga aagacattgc ttttaaacaa 1200
gaaaaaacaa actaa 1215

<210> SEQ ID NO 29
<211> LENGTH: 1230
<212> TYPE: DNA
<213> ORGANISM: Bacillus cereus

<400> SEQUENCE: 29
atgaaaaaaa ctccatttaa ggtgttaact tttatcactt tggcatcaat tataactact 60
actaacggta gtgctattca tgtatttgca caagatcgga ctttacaaga acaaaaaata 120
gaaatttata cattaggacc tgaagggcta aagaaagaat tggctaaaac cggatctaat 180
attctcgtaa tggacttgta cgcaaaaaca atgattaaac agccaaacgt aaacttatcc 240
agtattgatt taggttcagg aggagaagaa ttaatcaaaa acattcaatt gaatcaggaa 300
ttatcacgaa tcaatgcaag ttactggtta gatacagcga agccaaagat tcaaaaaaca 360
gtacgtaaca ttgtaaatta tgatgagcaa tttcaaaatt attacgacac attagtagat 420
actgtaaaaa agaatgataa gatgaacctc aaagaaggaa taggggattt aatccataca 480
attcatacaa attcaaatga agttacggaa gtcattaaga tgttagaggc tttcaaaaca 540
aagttgtata caaatactgt agactttaaa aataatgttg ggggccctga tggtaagggt 600
ggattaacgg ctatactagc cggaaaacag gcattggttc cacaacttca ggctgaaatt 660
gagaatttac gttctacgca gaaattacat tttgataatg tattagcctg gtcaattggt 720
ggtggattag gagcagctat tttagttatt ggagcgattg caggagcggt agtaattgtt 780
gtgactggtg gtacagctac accagctgtt gttggcggtc ttacagctct aggagcagct 840
ggtatcggtt taggaacagc agctggtgtt gaggcatcta atcatatgaa ttcctataat 900
gaaatttcaa ataaaatcgg agaattaagt atgaaagctg atttagctaa ccaagcggtt 960
atatcactta ctaatacaaa agacacttta acatatttgt atcagacagt ggatcaagcg 1020
ataatgtctc taacaagtat tcagcaacaa tggaataaaa tgggagctaa ttataaagat 1080
ttatatgata atatcgatca aatgcaagaa cataaactat ctttaatacc tgatgattta 1140
aaggctgcta aacaaagttg ggatgaaatt cataaggacg cagaattcat ttcaaaagac 1200
attgctttta aacaagaaaa aacaaactga 1230

<210> SEQ ID NO 30
<211> LENGTH: 1227
<212> TYPE: DNA
<213> ORGANISM: Bacillus weihenstephanensis

<400> SEQUENCE: 30
atgaaatttc catttaaggt cataactttg gccactttag caacggttat aactgctacg 60
aatggtagta ctattcacgc acttgcacaa gaacagacag cacaagaaca gaaaatagaa 120
aattatgcgt taggacctga agggttaaag aaagtgttgg ctaaaacagg ctctcatatt 180
cttgtaatgg atttgtacgc aaaaacaatg attaagcaac cgaatgtaaa tttatccaac 240
attgatttag gttcaggagg gggagaatta atcaaaaaca ttcacctgaa tcaagaactg 300
tcacgaatca atgcaaatta ctggctagat acagcgaagc caaacattca aaagacagca 360
cgtaatattg taaattatga tgaacaattt caaaattatt acgacacact agtagatact 420
gtaaaaaaga aagataaggc gggcctcaaa gaaggaatag gggatttaat cggtacaatt 480
catacaaatt caaatgaagt tacggaaatt attaagatgt tagaagcttt caaaacaaag 540

```
ttgtatacaa atactgtaga ttttaaaaat aatgttggag gtccagatgg acaaggggga    600

ttaacggcta tattagcggg aaaacaagca ctagtcccac aacttcaggc cgaaattgag    660

aatttacgtt ctacgcagaa agcacatttt gataatgtat tagcctggtc aattggtggt    720

ggattaggag cagctatttt agttattgga acgattgcag gagcggtagt aattgttgtg    780

accggtggca cagcgacacc agctgttgtt ggtggtctaa cggctctagg ggcagctggt    840

atcggtttag gaacagcagc tggtgttgag gcatctaatc atatgaactc ctataatgaa    900

atttcgaata aaattggaga attaagtatg aaagctgatt tagctaacca agcagttatt    960

tcacttacta atacaaaaga cactttaaca tatttgtatc aaacagttga tcaagcaatt   1020

atgtctctaa caagtattca gcaacaatgg aatacgatgg gagcgaatta taaagatcta   1080

tatgataata tcgaccaaat gcaagaacat aaactttctt taatacctga tgatttaaag   1140

gctgcaaaac aaagttggaa tgatattcat aaggatgcag aattcatttc aaaagacatt   1200

gcttttaaac aagaaaaaac aaattaa                                       1227
```

<210> SEQ ID NO 31
<211> LENGTH: 1002
<212> TYPE: DNA
<213> ORGANISM: Bacillus thuringiensis

<400> SEQUENCE: 31

```
gtgaataata attttcctta taaactactt gctgtatcga cgtttttaac cctgacaaca     60

actactgtag tttcaccagt agctgctttt gcaagtgaaa gtaaaataga acaaaccagt    120

acggaagata tatctctttc tgtaaacagt gaaaagatga aaaaagcttt gcaagatgct    180

ggggtatttg caaaatccat gaatgattac tcttatttgt taattaataa tccagatgtt    240

aactttgaag gaattgatat taaaggatat acaaatctac ctagtcaaat tgcacaagat    300

caaaagaatg caagagagca tgctacaaaa tgggatgctc acataaaaaa acaactttta    360

gataccctta caggaattgt agagtatgat accacatttg acaattatta cgatacatta    420

gtagaagcaa ttaatgaagg agatgcagat acattaaaag aaggcattac agatttacaa    480

ggtgagatta aacaaaacca agcatataca cagaatttaa ttcaagaact agctaagtta    540

agagatagta ttggagaaga tgtccgagca tttggaggtc ataaagatat cttgcaatcg    600

attttaaaaa atcaagcatc tggaatagat gaagatgaaa aacgcctaaa tgatgtttta    660

gagcaaataa gacattttaa acaagtagaa tcggatggaa taataactgt atcatatcct    720

tcaatcccta catggattgc tggaggtgtg atgatagggg tagcaagaaa taatttaggt    780

acgttagagc cgttattagt gcaattacgc caaaccgtag actataaaat aacattaaat    840

cgtgtagttg gagttgcgta taataatatt actgaaatgc aaaatgcaat tggatcagct    900

attaatgctc ttacctatat gtcagcacaa tggcatgatt tagattctca atattcagga    960

gtgcttaatc atattgataa agcatcccaa aaagcagatc aa                      1002
```

<210> SEQ ID NO 32
<211> LENGTH: 1009
<212> TYPE: DNA
<213> ORGANISM: Bacillus thuringiensis

<400> SEQUENCE: 32

```
gtgaataata attttcctta taaactactt gctgtatcga cgtttttaac cctgacaaca     60

actactgtag tttcaccagt agctgctttt gcaagtgaaa gtaaaataga acaaaccagt    120
```

```
acggaagata tatctctttc tgtaaacagt gaaaagatga aaaaagcttt gcaagatgct    180
ggggtatttg caaaatccat gaatgattac tcttatttgt taattaataa tccagatgtt    240
aactttgaag gaattgatat taaaggatat acaaatctac ctagtcaaat tgcacaagat    300
caaaagaatg caagagagca tgctacaaag tgggatgcgc acataaaaaa acaactttta    360
gatactctta caggaattgt agagtatgat actacatttg acaattatta cgatacatta    420
gtagaagcaa ttaatgaagg agatgcagat acattaaaag aaggcattac agatttacaa    480
ggtgagatta aaaaaaacca agcatataca aagaatttaa tacaagaact agctaagtta    540
agagatagta ttggagaaga tgtccgagca tttggaggtc ataaagatat cttgcaatcg    600
attttaaaaa atcaagcatc tggaatagat gaagatgaaa aacgtctaaa tgatgtttta    660
gagcaagtaa gacattttaa acaagtagaa tcggatggaa taataactgt atcagttccc    720
tcaatcccta catggattgc tggaggtgta atgatagggg tagcaagaaa taatttaagt    780
acgctggaac cgctattagc gcaattgcgc caaacggtag actataaaat tacattgaat    840
cgtgtagttg gagttgcgta taataatatt gctgaaatgc aaaatgcaat tggatcagct    900
attaatgctc tcacctatat gtcagcacaa tggcatgatt tagattctca atattcagga    960
gtacttaatc atattgataa agcatcccaa aaagcagatc aaaataatt              1009
```

```
<210> SEQ ID NO 33
<211> LENGTH: 1134
<212> TYPE: DNA
<213> ORGANISM: Bacillus cereus

<400> SEQUENCE: 33
gtgaataata attttcctta taaactactt gctgtatcga cgtttttaac cctgacaaca     60
actactgtag tttctccagt agctgctttt gcaagtgaaa gtaaaataga acaaacgagt    120
actgaagata tatctctttc tgtaaacagc gaaaagatga aaaaagcttt gcaagatgct    180
ggggtatttg caaaatccat gaatgattac tcttatttgt taattaataa tccagatgtt    240
aactttgaag gaattgatat taaaggatat acaaatctac ctagtcaaat tgtacaagat    300
caaaagaatg caagagagca tgctacaaaa tgggatgcgc acataaaaaa acaactttta    360
gataccctga caggaattgt agagtatgat accacatttg acaattatta cgatacatta    420
gtagaagcaa ttaatgaagg agatgcagat acattaaaag agggcattac agatttacaa    480
ggtgagatta aacaaaacca agcatataca cagaatttaa tacaagaact agctaagtta    540
agagatagta ttggagaaga tgtccgagca tttggaggtc ataaagatat cttgcaatcg    600
attttaaaaa atcaagcatc tggaatagat gaagatgaaa aacgcctaaa tgatgtttta    660
gagcaaataa gacattttaa acaagtagaa tcggatggaa taataactgt atcatatcct    720
tcaatcccta catggattgc tggaggtgtg atgataggag tagcaagaaa taatttaggt    780
acgttagagc cgttattagc acaattacgc caaacggtag actataaaat aacattaaat    840
cgtgtagttg gagttgcgta taataatatt gctgaaatgc aaaatgcaat tggatcagct    900
attaatgctc ttacctatat gtcagcacaa tggcatgatt tagattctca atattcagga    960
gtgcttaatc atattgataa agcatcccaa aaagcagatc aaaataaatt taaattctta   1020
aaacctaacc tgaatgcagc gaaagacagc tggaaaacat taagagcaga tgcgtttaca   1080
ttgaaagaag gaataaaaac attaaaaatg gatcctgttt cttcaaaaaa atag         1134

<210> SEQ ID NO 34
<211> LENGTH: 1133
```

-continued

<212> TYPE: DNA
<213> ORGANISM: Bacillus cereus

<400> SEQUENCE: 34
gtgaataata attttcctta taaactactt gctgtatcga cgtttttaac cctgacaaca 60
actactgtag tttctccagt agctgctttt gcaagtgaaa gtaaaataga acaaacgagt 120
actgaagata tatctctttc tgtaaacagc gaaaagatga aaaaagcttt gcaagatgct 180
ggggtatttg caaaatccat gaatgattac tcttatttgt taattaataa tccagatgtt 240
aactttgaag gaattgatat taaaggatat acaaatctac ctagtcaaat tgtacaagat 300
caaaagaatg caagagagca tgctacaaaa tgggatgcgc acataaaaaa acaactttta 360
gataccctga caggaattgt agagtatgat accacatttg acaattatta cgatacatta 420
gtagaagcaa ttaatgaagg agatgcagat acattaaaag agggcattac agatttacaa 480
ggtgagatta aacaaaacca agcatataca cagaatttaa tacaagaact agctaagtta 540
agagatagta ttggagaaga tgtccgagca tttggaggtc ataaagatat cttgcaatcg 600
attttaaaaa atcaagcatc tggaatagat gaagatgaaa aacgcctaaa tgatgtttta 660
gagcaaataa gacattttaa acaagtagaa tcggatggaa taataactgt atcatatcct 720
tcaatcccta catggattgc tggaggtgtg atgataggag tagcaagaaa taatttaggt 780
acgttagagc cgttattagc acaattacgc caaacggtag actataaaat aacattaaat 840
cgtgtagttg gagttgcgta taataatatt gctgaaatgc aaaatgcaat tggatcagct 900
attaatgctc ttacctatat gtcagcacaa tggcatgatt tagattctca atattcagga 960
gtgcttaatc atattgataa agcatcccaa aaagcagatc aaaataaatt taaattctta 1020
aaacctaacc tgaatgcagc gaaagacagc tggaaaacat taagagcaga tgcgtttaca 1080
ttgaaagaag gaataaaaac attaaaaatg gatcctgttt cttcaaaaaa ata 1133

<210> SEQ ID NO 35
<211> LENGTH: 1125
<212> TYPE: DNA
<213> ORGANISM: Bacillus cereus

<400> SEQUENCE: 35
gtgaataata attttcctta taaattactt gctgtatcgg cgtttttaac tctgacaaca 60
gctactgtag tttctccagt agctgcattt gcaagtgaaa gtaaaattga acaaacgagt 120
acggaaaata tatctctttc tgtaaacagc gaaaagatga aaaaagcttt gcaagatgct 180
gggggatttg caaaatccat gaatgattac tcttatttgt taattaataa tccaggtgtt 240
aactttgaag gaattgatat taaaggatat acaaatctac ctagtcaaat tatacaagat 300
caaaagaagg caagagagca tgctacaaaa tgggatacgc acataaaaaa acaactttta 360 gatacccttta caggaattgt agagtatgat accacatttg acaattatta cgatacatta 420
gtaaaagcaa ttaatgaagg agatgcagat acattaaaag aaggcattac agatttacaa 480
ggtgatatta aacaaaacca agcatataca cagaatttaa tacaagaact agctaagtta 540
agagatagta ttggagaaga tgtccgagca tttggaggtc ataaagatat cttgcaatcg 600
attttaaaaa atcaagcatc tggaatagat gaagatgaaa aacgcctaaa tgatgtttta 660
gagcaaataa gacattttaa acaagtagaa tcggatggaa taataactac atatgtaccc 720
tcgattccta catggattgc tggtggtata atgatagggg tagcaagaaa taatttaagt 780
acgttagaac cgctattagc gcagttgcgc caaacggtag actataaaat tacattgaat 840

-continued cgtgtagttg gagttgcgta taataatatt gctgaaatgc agaatgcaat tggatcagct 900
attaatgctc ttacctatat gtcagcacaa tggcaggatt tagattctca atattcaggg 960
gtacttaatc atattgataa agcatcccaa aaagcagatc aagataaatt taaattctta 1020
aaacctaacc tgaatgcagc gaaagacagt tggaaaacat taagagaaga tgcgtctaca 1080
ttaaaggaag ggataagaat attaaaagct tcttcaaaat cataa 1125

<210> SEQ ID NO 36
<211> LENGTH: 1134
<212> TYPE: DNA
<213> ORGANISM: Bacillus weihenstephanensis

<400> SEQUENCE: 36
atgaataaaa actttcctta taaactactt gctgtatcga cgtttttaac tctgacaaca 60
actactgtag tttctccagt ggcagccttc gcaagtgaaa gtaaaatgga acaaactagt 120
accgaagata tatctctttc tgtaaacagc gaaaagatga aaaaagcttt gcaagatgct 180
ggggtatttg caaaatccat gaatgattac tcttatttgt taattaaaaa cccagatgtt 240
aactttgaag gcattgacat taaaggatat acaaatctac ctagtcaaat tctacaagat 300
caaaagaatg caagagagca tgctacgaaa tgggattcac acataaaaaa acaactttta 360
gatacactga cggggattgt agagtatgat actaaattcg acaattatta tgacacatta 420
gtagaagcga ttaatgaagg ggatgcagac acattaaaag aaggcatgac agatttacaa 480
ggtgagatta aacaaaatca agcatataca cagaatttaa tacaagaact agctaagtta 540
agagatagta ttggagaaga tgtccgggca tttggaggtc ataaagatat tttgcattcg 600
attctgaaaa accaagcatc tggaattgat gaagatgaaa agcgcctaaa tgaagtttta 660
gagcaagtaa gacattttaa acaagtagaa tcagatggaa taataactgt atcaattccc 720
tcaattccta cgtggattgc tggtggtgta atgatagggg tagcaagaaa taatttaggt 780
acgttagagc cgttgttagc acaattacgt cagactatag attataaagt aacattaaat 840
cgtgtagttg gtgttgcgta taataatatt aatgaaatgc acaatgcgat tggatcggct 900
attaatgcac ttacctatat gtctgcacaa tggcatgatt tagattctca atattcggga 960
gtgcttagtc atattgataa agcatcccaa aaagcggatc aaaataaatt caaattccta 1020
aaacctaatt tgaatgcagc gaaagatagt tggaaaacat tgagagcgga tgcgtttaca 1080
ttaaaagaag ggataaaaac attaaaaatg gatcctgttt cttcaaaaaa atag 1134

<210> SEQ ID NO 37
<211> LENGTH: 964
<212> TYPE: DNA
<213> ORGANISM: Bacillus thuringiensis

<400> SEQUENCE: 37
atattatttt gcacagccag acattaaggt aaatgcgatg agtagcttag cgaatcatca 60
aaagtttgca aaggcgaatg tacgagagtg gattgatgaa tataatccga agctaattga 120
cttaaatcaa gagatgatga gatacagcac tagattcaat agttattata gtaagctcta 180
tgaactagca ggaaatgtaa atgaagatca gcaagcaaaa acagatttta tgagtgcata 240
tggaaaatta caattgcaag tacagagcat ccaagagagt atggagcaag atttattaga 300
gttaaatcga tttaaaacag tattagacaa agatagtaac aacttatcaa ttaaagccga 360
tgaagcaata aaaacactgc aaggatcaag tggagatatt gtgaaattaa gagaagatat 420
taaaagaatt caaggggaaa ttcaagctga actaactact attttgaata gacctcaaga 480

```
aataattaaa ggttctatta atatcggtaa acaagtattt acaatcacaa atcaaactgc    540
acaaacgaaa acaatcgatt ttgtttctat cggtacttta agtaatgaaa ttgtaaatgc    600
tgcagatagt caaacgagag aagcagcttt tcgcattcag caaaagcaaa aagagttatt    660
gccacttatt caaaagttat cacaaactga agcagaggcg actcaaatta cattcgttga    720
agatcaagta aatagcttta cagaattaat tgatcgtcaa attacaactt tagaaacgtt    780
attaacggat tggaaagttt taaataataa tatgattcaa attcaaacaa atgttgaaga    840
aggcacgtat acagacagta gtttacttca aaaacatttt aatcaaatta aaaaagtaag    900
tgatgaaatg aataagcaaa caaatcaatt tgaagattac gttacaaacg ttgaagtaca    960
ttaa                                                                 964
```

<210> SEQ ID NO 38
<211> LENGTH: 1161
<212> TYPE: DNA
<213> ORGANISM: Bacillus cereus

<400> SEQUENCE: 38

```
gtgaaaaaga ctttaattac agggttattg gttacagcag tatctacgag ttgcttcatt     60
cctgtaagcg cttacgctaa ggaggggcaa acagaagtga aacagtata tgcgcaaaat    120
gtaattgctc caaatacatt atccaattca attagaatgt taggatcaca atcaccgctt    180
attcaagcat acggattaat tatcttgcaa cagccagaca ttaaggtaaa tgcgatgagt    240
agcttaacga atcatcaaaa gtttgcaaag gcgaatgtaa gagaatggat tgatgaatat    300
aatccgaagc taattgactt aaatcaagaa atgatgagat acagcactag atttaatagc    360
tattatagta agctctatga actagcagga aacgtaaatg aagatcagca agcaaaagca    420
gattttatga gtgcatatgg aaaattacaa ttgcaagtac aaagcatcca agagagtatg    480
gagcaagatt tattagagtt aaatagattt aaaacagtat tagacaaaga tagtaacaac    540
ttatcaatta aagccgatga agcaataaaa acactgcaag gatcaagtgg agatattgtg    600
aaattaagag aagatattaa aagaattcaa ggggaaattc aagctgaact aactactatt    660
ttgaatagac ctcaagaaat cattaaaggt tctattaata tcggtaaaca agtatttaca    720
atcacaaatc aaactgcaca aacgaaaaca atcgattttg tttctatcgg tactttaagt    780
aatgaaattg taaatgctgc agatagtcaa acgagagaag cagctcttcg cattcaacaa    840
aagcaaaaag agttattacc acttattcaa aagttatcac aaactgaagc agaggcgact    900
caaattacat tcgttgaaga tcaagtaaat agctttacag aattaattga tcgtcaaatt    960
acaactttag aaacgttatt aacggattgg aaagttttaa ataataatat gattcaaatt   1020
caaacaaatg ttgaagaagg cacgtataca gacagtagtt tacttcaaaa acatttcaat   1080
caaattaaaa aagtaagtga tgaaatgaat aagcaaacaa atcaatttga agattacgtt   1140
acaaacgttg aagtacatta a                                             1161
```

<210> SEQ ID NO 39
<211> LENGTH: 1161
<212> TYPE: DNA
<213> ORGANISM: Bacillus cereus

<400> SEQUENCE: 39

```
gtgaaaaaga ctttaattac agggttattg gttacagcag tatctacgag tcgcttcatt     60
cctgtaagcg cttacgctaa ggaggggcaa acagaagtga aacagtata tgcgcaaaat    120
```

-continued

```
gtaattgctc caaatacatt atccaattca attagaatgt taggatcaca atcaccgctt    180

attcaagcat acggattaat tattttgcaa cagccagaca ttaaggtaaa tgcgatgagt    240

agcttaacga atcatcaaaa gttcgcaaag gcgaatgtgc gagagtggat tgatgaatat    300

aatccgaagc taattgactt aaatcaagaa atgatgagat acagcactag atttaatagc    360

tattatagta agctctatga actagcagga aacgtaaatg aagatcagca agcaaaagca    420

gattttatga gtgcatatgg aaaattacaa ttgcaagtac agagcatcca agagagtatg    480

gagcaagatt tattagagtt aaatcgattt aaaacagtat tagacaaaga tagtaacaac    540

ttatcaatta aagccgatga agcaataaaa acactgcaag gatccagtgg agatattgtg    600

aaattaagag aagatattaa aagaattcaa ggggaaattc aagctgaact aactactatt    660

ttgaatagac ctcaagaaat tattaaaggt tctattaata tcggtaaaca agtatttaca    720

atcacaaatc aaactgcaca aacgaaaaca atcgattttg tttctatcgg tactttaagt    780

aatgaaattg taaatgctgc agatagtcaa acgagagaag cagctcttcg cattcaacaa    840

aagcaaaaag agttattgcc acttattcaa aagttatcac aaactgaagc agaggcgact    900

caaattacat tcgttgaaga tcaagtaaat agctttacag aattaattga tcgtcaaatt    960

acaactttag aaacgttatt aacggattgg aaagttttaa ataataatat gattcaaatt   1020

caaaagaatg ttgaagaagg cacgtataca gacagtagtt tacttcaaaa acatttcaat   1080

caaattaaaa aagtaagtga tgaaatgaat aagcaaacaa atcaatttga agattacgtt   1140

acaaacgttg aagtacatta a                                              1161
```

<210> SEQ ID NO 40
<211> LENGTH: 1161
<212> TYPE: DNA
<213> ORGANISM: Bacillus cereus

<400> SEQUENCE: 40

```
gtgaaaaaga ctttaattac agggttattg gttacagcag tatctacgag ttgcttcatt     60

cctgtaagcg cttacgctaa ggaggggcaa ccagaagtga aacagtata tgcacaaaat    120

gtaattgttc caaatacatt atccaattca attagaatgt taggatcaca gtcaccactt    180

atacaagcat atggactagt gattttacaa cagccagaca twaaggtgaa cgcgatgagt    240

agtttgacga atcatcaaaa gtttgcaaag gcaaatgtaa gagagtggat tgatgaatat    300

aatccgaagt taatcgactt aaatcaagag atgatgaggt atagtactag atttaatagc    360

tattatagta agctctatga actagcaggg aacgtaaatg aagatggaca agcaaaagca    420

gattttacag gtgcatatgg aaaattacaa ttgcaagtac aaagcatcca agagagtatg    480

gagcaagatt tattagagct aaatcgattt aaaacggtat tagataagga tagtaacaac    540

ttatcagtta aagctgatga agcaataaaa acactacaag gatcaagtgg agatattgtg    600

aaattaagag aagatattaa aagaattcaa ggggaaattc aagctgaatt aacgactatt    660

ttgaatagac ctcaagaaat tattaaaggt tctattaata tcggtaaaca agtatttaca    720

attacaaatc aaactgcaca aacgaaaaca attgatttcg tttctatcgg tactttaagt    780

aatgaaattg taaatgctgc agatagccaa acgagagaag cagctcttcg cattcagcaa    840

aagcaaaaag agctattgcc acttattcaa aagttatcac aaactgaagc agaggcaaca    900

caaattacat tcgttgaaga tcaagtaagt agtttcacag aactaatcga tcgtcaaatc    960

acaactttag aaacgttatt agcagattgg aaagttttaa acagtaatat gatccaaatt   1020

caaaagaatg ttgaagaagg cacatataca gacagtagtt tactacaaaa acatttcaac   1080
```

-continued

```
caaattaaaa aagtaagtga tgaaatgaat aaacaaacga atcaatttga agattacgtt   1140

acaaacgttg aagtacatta a                                              1161
```

<210> SEQ ID NO 41
<211> LENGTH: 1161
<212> TYPE: DNA
<213> ORGANISM: Bacillus cereus

<400> SEQUENCE: 41

```
gtgaaaaaga ctttaattac agggttattg gttacagcag tatctacgag ttgcttcatt     60

cctgtaagcg cttacgctaa ggaggggcaa acagaagtga aaacagtata tgcgcaaaat    120

gtaattgctc caaatacatt atccaattca attagaatgt taggatcaca atcaccgctt    180

attcaagcat acggattaat tatcttgcaa cagccagaca ttaaggtaaa tgcgatgagt    240

agcttaacga atcatcaaaa gtttgcaaag gcgaatgtac gagaatggat tgatgaatat    300

aatccgaagc taattgactt aaatcaagaa atgatgagat acagcactag atttaatagc    360

tattatagta agctctatga actagcagga aacgtaaatg aagatcagca agcaaaagca    420

gattttatga gtgcatatgg aaaattacaa ttgcaagtac aaagcatcca agagagtatg    480

gagcaagatt tattagagtt aaatcgattt aaaacagtat tagacaaaga tagtaacaac    540

ttatcaatta aagccgatga agcaataaaa acactgcaag gatcaagtgg agatattgtg    600

aaattaagag aagatattaa aagaattcaa ggggaaattc aagctgaact aactactatt    660

ttgaatagac ctcaagaaat cattaaaggt tctattaata tcggtaaaca agtatttaca    720

atcacaaatc aaactgcaca aacgaaaaca atcgattttg tttctatcgg tactttaagt    780

aatgaaattg taaatgctgc agatagtcaa acgagagaag cagctcttcg cattcaacaa    840

aagcaaaaag agttattacc acttattcaa aagttatcac aaactgaagc agaggcgact    900

caaattacat tcgttgaaga tcaagtaaat agctttacag aattaattga tcgtcaaatt    960

acaactttag aaacgttatt aacggattgg aaagttttaa ataataatat gattcaaatt   1020

caaacaaatg ttgaagaagg tacgtataca gacagtagtt tacttcaaaa acatttcaat   1080

caaattaaaa aagtaagtga tgaaatgaat aagcaaacaa atcaatttga agattacgtt   1140

acaaacgttg aagtacatta a                                              1161
```

<210> SEQ ID NO 42
<211> LENGTH: 1161
<212> TYPE: DNA
<213> ORGANISM: Bacillus cereus

<400> SEQUENCE: 42

```
gtgaaaaaga ctttaattac agggttattg gttacagcag tatctacgag ttgttttatt     60

cctgtaagcg cttacgctaa ggaggggcaa acagaagtga aaacagtata tgcacaaaat    120

gtaattgctc caaatacatt atcgaattca attagaatgt taggatcaca atcaccactt    180

atacaagcat atggattagt tattttacaa cagccagaca ttaaggtaaa cgcgatgagt    240

agtttgacga atcaccaaaa atttgcaaag gcaaatgtaa gagagtggat tgatgaatat    300

aatccgaagt taatcgactt aaatcaagag atgatgaggt atagtactag atttaatagc    360

tattatagta agctctatga actagcagga aaagtcaatg aagatgaaca agcaaaagca    420

gattttacaa atgcatatgg aaaattacaa ttgcaagtac aaagcatcca agagagtatg    480

gagcaagatt tattagagtt aaatcgattt aaatcggtat tagataaaga tagtaataac    540
```

-continued

```
ttatcaatta aagctgatga agcaataaaa acactgcaag gatcaagtgg agatattgtg    600

aaattaagag aagatattaa aagaattcaa ggggaaattc aagctgaatt aactactata    660

ttgaatagac ctcaagaaat tattaaaggt tctattaata tcggtaaaca agtatttaca    720

attacaaatc aaactgcaca aacgaaaacg attgatttcg tttctatcgg tactttaagt    780

aatgaaattg taaatgctgc agatagccaa acgagagaag cagctcttcg cattcagcaa    840

aagcaaaaag agctattacc acttattcaa aaattatcac aaactgaagc agaagcgact    900

caaattacat tcgttgaaga tcaggtaaat agttttacag aactaattga tcgtcaaatt    960

acaacattag aaacgttatt aacggattgg aaagttttaa acaataatat gatccaaatt   1020

caaaagaatg ttgaagaagg cacgtataca gatagtagtt tacttcaaaa acatttcaat   1080

caaattaaaa aagtaagtga tgaaatgaat aaacaaacaa atcaatttga agattatgtt   1140

acaaacgttg aagtacatta a                                             1161
```

```
<210> SEQ ID NO 43
<211> LENGTH: 1161
<212> TYPE: DNA
<213> ORGANISM: Bacillus thuringiensis

<400> SEQUENCE: 43
```

```
gtgaaaaaga ctttaattac agggttattg gttacagcgg tatctacgag ttgttttatt     60

cctgtaagcg cttacgctaa ggaggggcaa acagaagtga aacagtata tgcacaaaat    120

gtaattgctc caaatacatt atcgaattca attagaatgt taggatcaca atcaccactt    180

atacaagcat atggattagt tattttacaa cagccagaca ttaaggtaaa cgcgatgagt    240

agtttgacga atcatcaaaa atttgcaaag gcaaatgtaa gagagtggat tgatgaatat    300

aatccgaagt taatcgactt aaatcaagag atgatgaggt atagtactag atttaatagc    360

tattatagta agctctatga actagcaggg aacgtaaatg aggatgaaca agcaaaagca    420

gattttacaa atgcatatgg aaagttacaa ttgcaagtac aaagcatcca agaaagtatg    480

gagcaagatt tattagagtt aaatcgattt aaatcggtat tagataaaga tagtaataac    540

ttatcaatta aagctgatga agcaataaaa acactgcaag gatcaagtgg agatattgtg    600

aaattaagag aagatattaa aagaattcaa ggagaaattc aagcagaatt aacgactatt    660

ttgaatagac ctcaagaaat tattaaaggt tctattaata tcggtaaaca agtgtttaca    720

attacaaatc aaactgcgca gacgaaaaca attgattttg tttctatcgg tactttaagt    780

aatgaaattg taaatgctgc agatagtcaa acgagagaag cagctcttcg cattcagcaa    840

aagcaaaaag agttattacc acttattcaa aaattatcac aaactgaagc agaagcgact    900

caaattacat tcgttgaaga tcaagtaagt agctttacag aactaattga tcgtcaaatt    960

acaacattag aaacgttatt aacggattgg aaagttttaa acaataatat gctccaaatt   1020

caaaagaatg ttgaagaagg cacgtataca gatagtagtt tacttcaaaa acatttcaat   1080

caaattaaaa aagtaagtga tgaaatgaat aaacaaacaa atcaatttga agattatgtt   1140

acaaacgttg aagtacatta a                                             1161
```

```
<210> SEQ ID NO 44
<211> LENGTH: 1161
<212> TYPE: DNA
<213> ORGANISM: Bacillus thuringiensis

<400> SEQUENCE: 44
```

```
gtgaaaaaga ctttaattac agggttattg gttacagcag tatctacgag ttgcttcatt     60
```

```
cctgtaagcg cttacgctaa ggaggggcaa acggaagtga aaacagtata tgcacaaaat    120

gtaattgctc caaatacatt atccaattca attagaatgt taggatcaca atcaccgctt    180

attcaagcat acggattaat tattttacaa cagccagata ttaaggtaaa tgcgatgagt    240

agcttaacga atcatcaaaa gtttgcaaag gcgaatgtac gagaatggat tgatgaatat    300

aatccgaagc taattgactt aaatcaagag atgatgagat acagcactag atttaatagc    360

tattatagta agctctatga attagcagga aacgtaaatg aagatcagca agcaaaagca    420

gattttatga gtgcatatgg aaaattacaa ttgcaagtac aaagcataca agagagtatg    480

gagcaagatt tattagagtt aaatcgattt aaaacagtat tagacaaaga tagtaacaac    540

ttatcaatta aagccgatga agcaataaaa acactgcaag gatcaagtgg agatattgtg    600

aaatcaagag aagatattaa aagaattcaa ggtgaaattc aagctgaatt aactactatt    660

ttgaatagac ctcaagaaat cattaaaggt tctattaata ttggtaaaca agtatttaca    720

atcacaaatc aaactgcaca aacgaaaaca atcgattttg tttctatcgg tactttaagt    780

aatgaaattg taaatgctgc agatagtcaa acgagggaag cagctcttcg cattcaacaa    840

aagcaaaagg agttattgcc acttattcaa aagttatcac aaactgaagc agaggcgact    900

caaattacat tcgttgaaga tcaagtaagt agctttacag aattaattga tcgtcaaatt    960

acaactttag aaacgttatt aacggattgg aaagttttaa ataataatat gattcaaatt   1020

caaacaaatg tcgaagaagg cacgtataca gacagtagtt tacttcaaaa acatttcaat   1080

caaattaaaa aagtaagtga tgaaatgaat aagcaaacaa atcaatttga agattacgtt   1140

acaaacgttg aagtacatta a                                             1161
```

<210> SEQ ID NO 45
<211> LENGTH: 1209
<212> TYPE: DNA
<213> ORGANISM: Bacillus thuringiensis

<400> SEQUENCE: 45

```
atgacaaaaa aaccatataa agtaatggct ctatcagcac ttatggcagt atttgcagca     60

ggaaatatta tgccggctca tacgtatgca gctgaaagta cagtgaaaca agctccagtt    120

catgcggtag caaaagctta taataactat gaagaatatt cattaggacc agaaggtttg    180

aaagatgcaa tggaaagaac aggttcaaat gctttagtaa tggatctgta tgctttaaca    240

attattaaac aaggtaatgt taactttgga aatgtatcga ctgttgatgc agctttaaaa    300

ggaaaagtga ttcagcacca agatacagct agaggaaatg cgaagcaatg gttagatgta    360

ttaaagccac agcttatttc aacgaatcaa aacatcatta actacaatac aaaattccaa    420

aactattatg atactttagt tgctgcggta gatgcaaaag ataaagcgac tcttacgaaa    480

ggcctaacta gattatcaag tagtattaat gaaaataaag cgcaagtgga tcagttagta    540

gaagacttga aaaaattccg aaataaaatg acgtcggata cgcaaaactt caagggtgat    600

gcaaatcaaa ttacatctat attagctagt caagatgcag ggattccact tctgcaaaat    660

caaattacaa cgtacaatga agcaattagt aaatataatg caattattat cggttcatct    720

gttgcgacag ctctaggacc aattgcaatt attggtggtg cagtagttat tgctacgggc    780

gcaggaacac cgctaggagt cgcattaatt gcaggtggtg cagcagctgt aggcggtggt    840

acagctggta tcgtattagc gaagaaagaa cttgacaatg cacaagctga aattcaaaaa    900

ataactggac aaattacaac tgctcaatta gaagtagctg ggttaacgaa cattaaaaca    960
```

caaactgagt atttaacaaa tacgattgat actgcaatta cagcgttgca aaacatttca 1020
aaccaatggt atacaatggg atcaaaatac aattctttac ttcaaaatgt ggattcaatt 1080
agtccaaacg atcttgtttt cattaaagaa gatttaaaca ttgcgaaaga tagctggaaa 1140
aacattaaag actatgcaga aaagatttat gctgaagata ttaaagtagt agatacgaaa 1200
aaagcataa 1209

<210> SEQ ID NO 46
<211> LENGTH: 1209
<212> TYPE: DNA
<213> ORGANISM: Bacillus cereus

<400> SEQUENCE: 46
atgacaaaaa aaccttataa agtaatggct ctatcagcac ttatggcagt atttgcagca 60
ggaaatatta tgccggctca tacgtatgca gctgaaagta cagtgaaaca agctccagtt 120
catgcggtag caaaagctta taatgactat gaagaatact cattaggacc agaaggcttg 180
aaagatgcaa tggaaagaac aggttcaaat gctttagtaa tggatctgta cgctttaaca 240
attattaaac aaggtaatgt taactttgga aatgtatcgt ctgttgatgc ggctttaaaa 300
gggaaagtaa ttcagcacca agatacagct agaggaaatg cgaagcaatg gttagatgta 360
ttaaaaccac agcttatttc aacaaatcaa aatatcatta actacaatac gaaattccaa 420
aactattatg atactttagt tgctgcagtt gatgcaaaag ataaagcgac tcttacgaaa 480
ggcttaacta gattatcaag tagtattaat gaaaataaag cacaagtgga tcagttagta 540
gaagacttga agaaattccg aaataaaatg acttcggata cgcaaaactt caagggtgat 600
gcaaatcaaa ttacatctat attagctagt caagatgcag ggattccgct tctgcaaaat 660
caaattacaa cgtacaatga agcaattagt aaatataatg caattattat cggttcatct 720
gttgcgacag ctctaggacc aattgcaatt atcggtggtg cagtagttat tgctacgggc 780
gcaggaacac cgctaggagt agcattaatt gcaggtggtg cagcagctgt aggcggtggt 840
acagctggaa tcgtattagc gaagaaagag cttgataatg cacaagcaga aattcaaaag 900
ataacaggac aagttacaac tgcgcaatta gaagtagcag gattaacgaa cattaaaaca 960
caaacagagt atttaacaaa tacaattgat actgcaatta cagcgttaca aaatatttca 1020
aaccaatggt acacaatggg atcaaaatac aattctttac ttcaaaatgt agattctatt 1080
agtccaaatg acctagtttt cattaaagaa gatttaaaca ttgcgaaaga tagctggaaa 1140
aacattaaag actatgcaga aaagatttat gctgaagata ttaaagtagt agatacgaaa 1200
aaagcataa 1209

<210> SEQ ID NO 47
<211> LENGTH: 1209
<212> TYPE: DNA
<213> ORGANISM: Bacillus cereus

<400> SEQUENCE: 47
atgacaaaaa aaccttataa agtaatggct ctatcagcac ttatggcagt atttgcagca 60
ggaaatatta tgccggctca tacgtatgca gctgaaagta cagtgaaaca agcgccagtt 120
catgcggtag caaaagctta taatgactat gaagaatact cattaggacc agaaggcttg 180
aaagatgcaa tggaaagaac aggttcaaat gctttagtag tggatctgta cgctttaaca 240
attattaaac aaggtaatgt taactttgga aatgtatcgt ctgttgatgc ggctttaaaa 300
gggaaagtaa ttcagcacca agatacagct agaggaaatg cgaagcaatg gttagatgta 360

-continued

```
ttaaaaccac agcttatttc aacgagtcaa aatatcatta actacaatac gaaattccaa    420

aactattatg atactttagt tgctgcagtt gatgcaaagg ataaagcaac tcttacgaaa    480

ggcttaacta gattatcaag tagtattaat gaaaataaag cgcaagtgga tcagttagta    540

gaagacttga agaaattccg aaataaaatg acttcggata cgcaaaactt caagggtgat    600

gcaaatcaaa ttacatctat attagctagt caagatgcag gaattccgct tctgcaaaat    660

caaattacaa cgtacaatga agcaattagt aaatataatg caattattat cggttcatct    720

gttgcgacag ctctaggacc aattgcaatt atcggtggtg cagtagttat tgctacgggc    780

gcaggaacac cgctaggagt agcattaatt gcaggtggtg cagcagctgt aggcggtggt    840

acagctggaa tcgtattagc gaagaaagag cttgataatg cacaagcaga aattcaaaag    900

ataacaggac aagttacaac tgcgcaatta gaagtagcag gattaacgaa cattaaaaca    960

caaacagagt atttaacaaa tacaattgat actgcaatta cagcgttaca aaatatttca   1020

aaccaatggt acacaatggg atcaaaatac aattctttac ttcaaaatgt agattctatt   1080

agtccaaacg acctagtttt cattaaagaa gatttaaaca ttgcgaaaga tagctggaaa   1140

aacattaaag actatgcaga aaagatttat gctgaagata ttaaagtagt agatacgaaa   1200

aaagcataa                                                            1209
```

<210> SEQ ID NO 48
<211> LENGTH: 1208
<212> TYPE: DNA
<213> ORGANISM: Bacillus cereus

<400> SEQUENCE: 48

```
atgacaaaaa aaccttataa agtaatggct ctatcagcac ttatggcagt atttgcagca     60

ggaaatatca tgccggctca tacgtatgca gcggagagta cagtgaagca agctccagtt    120

catgcggccg caaaagctta taatgattat gaggaatatt cattaggacc agaaggccta    180

aaagatgcaa tggaaagaac gggttcaaac gctttagtaa tggatctgta cgctttaaca    240

attattaaac aaggtaatgt taactttgaa atgtatcgtc tgttgatgcg gctttaaaag    300

ggaaagtgat tcagcaccag gatacagcta gaggaaatgc gaagcaatgg ttagatgtac    360

taaagccaca gcttatttca acgaatcaaa atatcattaa ttacaatacg aaattccaaa    420

actattacga tactttagtt gctgcggtag atgcaaaaga taaagcgact cttacgaaag    480

gtttaactag attatcaagt agtattaatg aaaataaagc gcaagtagat cagttagtag    540

atgacttgaa gaaattccga aataaaatga cgtccgatac gcaaaacttt aagggagacg    600

caaatcaaat tacatctatt ttagctagtc aagatgcagg aatcccgctt ctgcaaaatc    660

aaattacaac gtacaatgaa gcaattagta aatataatgc aattattatc ggttcatcag    720

ttgcgacagc tctagggcca attgccatta ttggtggtgc agtagtgatt gctacaggtg    780

caggaacgcc gttaggagtc gcgttaattg caggtggtgc agcagctgta ggcggtggca    840

cagctggtat cgtattagcg aagaaagaac ttgataatgc acaagctgaa attcaaaaaa    900

taacaggaca agttacaact gctcaattag aagtagctgg gttaacgaac attaagacac    960

aaacggagta tttaacaaat acaattgata ctgcaattac agcgttgcaa aacatttcaa   1020

accaatggta cacaatggga tcaaaataca attctttact tcaaaatgta gattcaatta   1080

gtccgaatga ccttgttttc attaaagaag atttaaacat tgcgaaagat agctggaaaa   1140

acattaaaga ctatgcagaa aagatttatg ctgaagatat taaagtagta gatacgaaaa   1200
```

-continued aagcttaa 1208

<210> SEQ ID NO 49
<211> LENGTH: 1209
<212> TYPE: DNA
<213> ORGANISM: Bacillus cereus

<400> SEQUENCE: 49
atgacaaaaa aaccttataa agtaatggct ctatcagcac tgatggcagt atttgcagca 60
ggaaatatta tgccggctca tacgtatgca gctgaaagta cagtgaaaca agctccagtt 120
catgcggtag caaaagctta taatgactat gaagaatact cattaggacc agaaggcttg 180
aaagatgcaa tggaaagaac aggttcaaat gctttagtaa tggatctgta cgctttaaca 240
attattaaac aaggtaatgt taactttgga aatgtatcgt ctgttgatgc ggctttaaaa 300
gggaaagtaa ttcagcacca agatacagct agaggaaatg cgaagcaatg gttagatgta 360
ttaaaaccac agcttatttc aacgaatcaa aatatcatta actacaatac gaaattccaa 420
aactattatg atactttagt tgctgcagtt gatgcaaagg ataaagcgac tcttacgaaa 480
ggcttaacaa gattatcaag tagtattaat gaaaataaag cgcaagtgga tcagttagta 540
gaagacttga agaaattccg aaataaaatg acttcggata cgcaaaactt caagggtgat 600
gcaaatcaaa ttacatctat attagctagt caagatgcag gaattccgct tctgcaaaat 660
caaattacaa cgtacaatga agcgattagt aaatataatg caattattat cggttcatct 720
gttgcgacag ctctaggacc aattgcaatt atcggtggtg cagtagttat tgctacgggt 780
gcaggaacac cgctaggagt agcattaatt gcaggtggtg cagcagctgt aggcggtggt 840
acagctggaa tcgtattagc gaagaaagag cttgataatg cacaagcaga aattcaaaag 900
ataacaggac aagttacaac tgcgcaatta gaagtagcag gattaacgaa cattaaaaca 960
caaacagagt atttaacaaa tacaattgat actgcaatta cagcgttaca aaatatttca 1020
aaccaatggt acacaatggg atcaaaatac aattctttac ttcaaaatgt ggattcaatt 1080
agtccaaacg atcttgtttt cattaaagaa gatttaaaca ttgcgaaaga tagctggaaa 1140
aacattaaag actatgcaga aaagatttat gctgaagata ttaaagtagt agatacgaaa 1200
aaagcataa 1209

<210> SEQ ID NO 50
<211> LENGTH: 1209
<212> TYPE: DNA
<213> ORGANISM: Bacillus cereus

<400> SEQUENCE: 50
atgacaaaaa aaccttataa agtaatggct ctatcagcac ttatggcagt atttgcagca 60
gggaatatta tgccggccca tacgtatgca gctgaaagta cagtgaaaca agctcccgta 120
catgcggtcg caaaagctta taatgactat gaagaatact cattaggacc agaaggctta 180
aaagatgcaa tggaaagaac aggttcaaac gctttagtaa tggatctgta tgctttaaca 240
atcattaaac aaggtaatgt taactttgga aatgtatcga ctgttgatgc tgctttaaaa 300
ggaaaagtga ttcagcacca ggatacagct agaggaaatg cgaagcaatg gttagatgta 360
ttaaagccac agcttatttc aacgaatcaa aatatcatta actataatac gaaattccaa 420
aactattatg atactttagt tgctgcggtt gatgcaaaag ataaagcgac acttacgaaa 480
gggttaacta gattatcaag tagtattaat gaaaataaag cgcaagtaga tcagttagta 540
gaagacttga agaaattccg aaataaaatg acgtcggata cccaaaactt caagggtgat 600

-continued gcaaatcaaa ttacatctat tttagctagt caagatgctg gaatcccact tctgcaaaat 660
caaattacaa cgtacaatga agcgattagt aaatataatg caattattat cggttcatca 720
gttgcgacag ctctagggcc aattgcaatt atcggtggtg cagtagttat tgctacaggt 780
gcaggaacgc cactaggagt cgcattaatt gcaggaggcg cagcggctgt aggcggtggt 840
acagctggaa tcgtattagc gaagaaagag cttgataatg cacaagctga aattcaaaaa 900
ataactggac aaattacaac tgctcaatta gaggtagcag gattaacaaa cattaaaaca 960
caaactgagt atttaacaaa tacaattgat actgcaatta cagcgttgca aaatatttca 1020
aatcaatggt acacaatggg atcaaaatac aattctctac ttcaaaatgt agattcaatt 1080
agtccaaacg accttgtttt cattaaagaa gatttaaaca ttgcgaaaga tagctggaaa 1140
aacattaaag actatgcaga aaagatttat gctgaagata ttaaagtagt agatacgaaa 1200
aaagcataa 1209

<210> SEQ ID NO 51
<211> LENGTH: 1209
<212> TYPE: DNA
<213> ORGANISM: Bacillus thuringiensis

<400> SEQUENCE: 51
atgacaaaaa aaccttataa agtaatggct ctatcagcac ttatggcagt atttgcggca 60
gggaatatta tgccgaccca tacgtatgca gctgaaagta cagtgaaaca agctccagtt 120
catgcggtcg caaaagctta taatgactat gaagaatact cattaggacc agaaggccta 180
aaagatgcta tggaaagaac aggttcaaac gctttagtaa tggatctgta tgctttaaca 240
atcattaaac aaggtaatgt taactttgga aatgtatcga ctgttgatgc tgctttaaaa 300
ggaaaagtga ttcagcacca ggatacagct agaggaaatg cgaagcaatg gttagatgta 360
ttaaagccac agcttatttc aacgaatcaa aatatcatta actataatac gaaattccaa 420
aactattatg atactttagt tgctgcggtt gatgcaaaag ataaagcgac acttacgaaa 480
gggttaacta gattatcaag tagtattaat gaaaataaag cgcaagtaga tcagttagta 540
gaagacttga agaaattccg aaataaaatg acgtcggata cgcaaaactt taagggggat 600
gcaaatcaaa ttacatctat tttagctagt caagacgctg gaatcccgct tctgcaaaat 660
caaattacaa cgtacaatga agcaattagt aaatataatg caattattat cggttcatca 720
gttgcgacag ctctagggcc aattgcaatt atcggtggtg cagtagttat tgctacaggt 780
gcaggaacgc cactaggagt cgcattaatt gcagggggcg cagcggctgt aggtggtggt 840
acagctggaa tcgtattagc gaagaaagag cttgataatg cacaagctga gattcaaaaa 900
ataactggac aaattacaac tgctcaatta gaggtagcag gattaacaaa cattaaaaca 960
caaacggagt atttaacaaa tacaattgat actgcaatta cagcgttgca aaatatttca 1020
aatcaatggt acacaatggg atcaaaatac aattctttac ttcaaaatgt agattcaatt 1080
agtccaaacg accttgtttt cattaaagaa gatttaaaca ttgcgaaaga tagctggaaa 1140
aacattaaag actatgcaga aaagatttat gctgaagata ttaaagtagt agatacgaaa 1200
aaagcataa 1209

<210> SEQ ID NO 52
<211> LENGTH: 1209
<212> TYPE: DNA
<213> ORGANISM: Bacillus thuringiensis -continued

<400> SEQUENCE: 52
atgacaaaaa aaccttataa agtaatggct ctatcagcac ttatggcagt atttgcagca 60
ggaaatatta tgccggctca tacgtatgca gctgaaagta cagtgaagca agctccagtt 120
catgcggtag caaaagctta taatgactat gaagaatatt cattaggacc agaaggccta 180
aaagatgcaa tggaaagaac aggttcaaat gctttagtaa tggatctgta cgctttaaca 240
attattaaac aaggtaatgt taactttgga aatgtatcgt ctgttgatgc ggctttaaaa 300
gggaaagtaa ttcagcacca agatacagct agaggaaatg cgaagcaatg gttagatgta 360
ttaaaaccac agcttatttc aacgaatcaa aatatcatta actacaatac gaaattccaa 420
aactattatg atactttagt tgctgcagtt gatgcaaagg ataaagcgac tcttacgaaa 480
ggcttaacta gattatcaag tagtattaat gaaaataaag cacaagtgga tcagttagta 540
gaagacttga agaaattccg aaataaaatg acttcggata cgcaaaactt caagggtgat 600
gcaaatcaaa ttacatctat attagctagt caagatgcag gaattccgct attacaaaat 660
caaattacaa cgtacaatga agcaattagt aaatataatg caattattat cggttcatct 720
gttgcgacag ctctaggacc aattgcaatt atcggtggtg cagtagttat tgctacgggc 780
gcaggaacac cgctaggagt agcattaatt gcaggtggtg cagcagctgt aggcggtggt 840
acagctggaa tcgtattagc gaagaaagag cttgataatg cacaagcaga aattcaaaag 900
ataacaggac aagttacaac tgcgcaatat gaagtagctg gattaacgaa cattaaaaca 960
caaacagagt atttaacaaa tacaattgat actgcaatta cagcgttaca aaatatttca 1020
aaccaatggt acacaatggg atcaaaatat aattctttac ttcaaaatgt ggattcaatt 1080
agtccaaacg accttgtttt cattaaagaa gatttaaaca ttgcgaaaga tagctggaaa 1140
aatattaaag actatgcaga aaagatttat gctgaagata ttaaagtagt agatacgaaa 1200
aaagcataa 1209

<210> SEQ ID NO 53
<211> LENGTH: 1028
<212> TYPE: DNA
<213> ORGANISM: Bacillus thuringiensis

<400> SEQUENCE: 53
atgcagaaac gattttataa aaaatgtctt ttagcggtaa tgattgctgg ggtggcaacg 60
agtaacgcat ttcctttaca tccttttgca gcagaacaaa atgtaacggt gctacaagaa 120
aatgtgaaaa actattctct tggaccagca ggattccaag atgtaatggc acaaacgaca 180
tcaagcatat ttgcaatgga ttcatatgca aaattaattc aaaatcaaca agagacggat 240
ttaagtaaaa taagttcgat taatagtgaa tttaaaggga gtatgattca gcatcaaaga 300
gatgcaaaaa ttaatgcagc atattggtta aataatatga agcctcaaat tatgaaaaca 360
gatcaaaata ttataaatta caataatact tttcaatcgt attataatga catgttaata 420
gcgattgatc aaaaggatag tggaaaatta aaagcggatt tagaaaagtt gtatgcggat 480
attgtaaaga atcaaaatga ggtagatgga ttattaggaa atttgaaagc ttttcgcgat 540
agaatggcga aagatacaaa tagtttcaaa gaggatacaa atcagttaac agcgatattg 600
gcaagtacga atgctggtat tccagctcta gagcaacaaa taaatacata taacgattcg 660
attaaaaaga gtaatgatat ggtcattgct ggtggcgtac tttgcgtagc tctaataaca 720
tgtcttgctg gcgggccgat gattgcggtt gcgaaaaaag atatcgcaaa tgcagaaaga 780
gaaatcgcca atttaaaaga tagaatttca ggagcacaag cagaagtcgt aattttgact 840

-continued gatgtaaaaa ataaaacaac aaacatgaca gaaacaattg atgcagcaat tacagcacta 900
caaaacatat caaatcaatg gtatacagta ggtgcaaagt ataataattt attacaaaac 960
gtaaaaggaa ttagtccgga agagtttacg tttataaaag aagatttaca tacagcgaaa 1020
gatagctg 1028

<210> SEQ ID NO 54
<211> LENGTH: 1080
<212> TYPE: DNA
<213> ORGANISM: Bacillus cereus

<400> SEQUENCE: 54
atgcagaaac gattttataa aaaatgtctt ttagcggtaa tgattgctgg ggtggcaacg 60
agtaacgcat ttcctttaca tccttttgca gcagaacaaa atgtaaaggt gctacaagaa 120
aatgtgaaaa actattctct tggaccagct ggattccaag atgtaatggc acaaacgaca 180
tcaagtatat ttgcaatgga ttcatatgca aaattaattc aaaatcaaca agagacggat 240
ttaagtaaaa taagttcgat taatagtgaa tttaaaggga atatgattca gcatcaaaga 300
gatgcaaaaa ttaatgcagc atattggtta aataatatga agcctcaaat tatgaaaacg 360
gatcaaaata ttataaatta caataatact tttcaatcgt attataatga catgttaata 420
gcgattgatc aaaaggatag cggaaaatta aaagcggatt tagaaaagtt gtatgcggat 480
attgtaaaga atcaaaatga ggtagatgga ttgttaggaa atttgaaaag ttttcgcgat 540
agaatggcga aagatacaaa tagtttcaaa gaggatacaa atcagttaac agcgatattg 600
gcaagtacga atgctggtat tccagctcta gagcaacaaa taaatacata taacgattcg 660
attaaaaaga gtaatgatat ggtcattgct ggtggcgtac tttgcgtagc tctaataaca 720
tgtcttgctg gtgggccgat gattgcggtt gcgaaaaaag atatcgcaaa tgcagaaaga 780
gaaatcgcca atttaaaaga tagaatttca ggagcacaag cagaagtcgt aattttgact 840
gatgtaaaaa ataaaacaac aaacatgaca gaaacaattg atgcagcaat tacagcacta 900
caaaacatat caaatcaatg gtatacagta ggtgcaaaat ataataattt actacaaaac 960
gtaaaaggaa ttactccaga agagtttacg tttataaaag aagatttaca tacagcgaaa 1020
gatagctgga aagatgtaaa ggattataca gaaaaattac atgaaggtgt ggcgaagtaa 1080

<210> SEQ ID NO 55
<211> LENGTH: 1080
<212> TYPE: DNA
<213> ORGANISM: Bacillus cereus

<400> SEQUENCE: 55
atgcagaaac gattttataa aaaatgtctt ttagcggtag tgattgctgg ggtggcaaca 60
agtaacgcat ttcctttaca tccttttgca gcagaacaaa atgtaaaggt gctacaagaa 120
aatgtgaaaa actattctct tggaccagct ggattccaag atgtaacggc acaaacgaca 180
tcaagtatat ttgcaatgga ttcatatgca aaattaattc aaaatcaaca agagacggat 240
ttaagtaaaa taagttcgat taatagtgaa tttaaaggga atatgattca gcatcaaaga 300
gatgcaaaaa ttaatgcagc atattggtta aataatatga agcctcaaat tatgaaaacg 360
gatcaaaata ttataaatta caataatact tttcaatcgt attataatga catgttaata 420
gcgattgatc aaaaggatag cggaaaatta aaagcggatt tagaaaagtt gtatgcggat 480
attgtaaaga atcaaaatga ggtagatgga ttgttaggaa atttgaaaag ttttcgcgat 540

-continued

```
agaatggcga aagatacaaa tagtttcaaa gaggatacaa atcagttaac agcgatattg    600

gcaagtacga atgctggtat tccagctcta gagcaacaaa taaatacata taacgattcg    660

attaaaaaga gtaatgatat ggtcattgct ggtggcgtac tttgcgtagc tctaacaaca    720

tgtcttgctg gtgggccgat gattgcggtt gcgaaaaaag atatcgcaaa tgcagaagga    780

gaaatcgcca atttaaaaga tagaatttca ggagcacaag cagaagtcgt aattttgact    840

gatgtaaaaa ataaaacaac aaacatgaca gaaacaattg atgcagcaat tacagcacta    900

caaaacatat caaatcaatg gtatacagta ggtgcaaaat ataataattt actacaaaac    960

gtaaaaggaa ttactccaga agagtttacg tttataaaag aagatttaca tacagcgaaa   1020

gatagctgga aagatgtaaa ggattataca gaaaaattac atgaaggtgt ggcgaagtaa   1080
```

```
<210> SEQ ID NO 56
<211> LENGTH: 1080
<212> TYPE: DNA
<213> ORGANISM: Bacillus cereus

<400> SEQUENCE: 56

atgcagaaaa gattttataa aaagtgtctt ttaacgttaa tgattgctgg ggtggcaacg     60

agtaatgtat ttcctttaca tccttttgca gcagaacaaa acgtaaaaac attgcaagaa    120

agtgcgggaa attattcgtt agggccagct ggattccaag atgtaatggc gcaaacgaca    180

tcgagcatat tcgcaatgga ctcctatgca aaattaattc aaaatcagca agagactgat    240

ttgagtaaaa taagttcgat taatagtgag tttaaaggaa atatgattca gcaccaacga    300

gatgcaaaaa ttaacgcggc gtattggtta gatcatatga agccgcaaat tatgaaaacg    360

gatcaaaata ttattgatta caataatact tttcaagcgt attatagtag catgctaata    420

gcaattgatc aaaaagatag cgtaaagtta aaagcggatt tagaaacatt gtatgcggat    480

attgtaaaga atcaaaatga ggtagatgta ttattaggta atttgaaagc ctttcgcgat    540

agaatggcga aagatacaaa tagctttaaa gcggatacaa atcaactaac ctcgatttta    600

gcaagtacga atgctggtat tccagcttta gagcaacaaa tcaatacata taacgattca    660

attaaaaaga gtaatgatat ggttatcgct ggtggtgtac tttgtgtagc gttaataaca    720

tgccttgctg gcggaccgat gattgccgtt gcgaaaaaag atattgcaaa tgcagaaaga    780

gaaattgcca atttaaagga tagaatttct ggcgcacaag cagaggtcgc aattttgaca    840

gatgtaaaaa ataaaacaac aaacatgact gaaacgattg atgcagcaat tacagcattg    900

caaaatatat cgaatcaatg gtatacagta ggggcaaaat ataataattt actacaaaac    960

gtaaaaggaa ttagtccgga agaatttacc ttcataaaag aagatttaca tacagcgaaa   1020

gatagctgga aagatgtaaa agattataca gaaaaattac atgaaggtgt ggcgaagtaa   1080
```

```
<210> SEQ ID NO 57
<211> LENGTH: 1080
<212> TYPE: DNA
<213> ORGANISM: Bacillus cereus

<400> SEQUENCE: 57

atgcagaaac gattttataa aaaatgtctt ttagcggtaa tgattgctgg ggtggcaacg     60

agtaacgcat ttcctttaca tccttttgca gcagaacaaa atgtaacggt gctacaagaa    120

aatgtgaaaa actattctct tggaccagca ggattccaag atgtaatggc acaaacgaca    180

tcaagcatat ttgcaatgga ttcatatgca aaattaattc aaaatcaaca agagacggat    240

ttaagtaaaa taagttcgat taatagtgaa tttaaaggaa atatgattca gcatcaaaga    300
```

-continued gatgcaaaaa ttaatgcagc atattggtta aataatatga agcctcaaat tatgaaaaca 360
gatcaaaata ttataaatta caataatact tttcaatcgt attataatga catgttaata 420
gcgattgatc aaaaggatag cggaaaatta aaagcggatt tagaaaagtt gtatgcagat 480
attgtaaaga atcaaaatga ggtagatgga ttattaggaa atttgaaagc ttttcgcaat 540
agaatggcga aagatacaaa tagtttcaaa gaagatacaa atcagttaac agcgatattg 600
gcaagtacga atgctggtat tccagctcta gagcaacaaa taaatacata taacgattcg 660
attaaaaaga gtaatgatat ggtcattgct ggtggcgtac tttgtgtagc attaataaca 720
tgtcttgctg gcgggccaat gatcgcggtt gcgaaaaaag atatcgcaaa tgcagaaaga 780
gaaatcgcta atttaaaaga tagaatttca ggagcgcaag cagaagtctt aattttgact 840
gatgtaaaaa ataaaacaac aaacatgaca gaaacaattg atgcagcaat tacagcacta 900
caaaacatat caaatcaatg gtatacagta ggtgcaaaat ataataattt actacaaaac 960
gtaaaaggaa ttagtccgga agagtttacg tttataaaag aagatttaca tacagcgaaa 1020
gatagctgga aagatgtaaa ggattataca gaaaaattac atgaaggcgt ggcgaagtaa 1080

<210> SEQ ID NO 58
<211> LENGTH: 1080
<212> TYPE: DNA
<213> ORGANISM: Bacillus cereus

<400> SEQUENCE: 58
atgcagaaac gattttataa gaaatgtctt ttaacattaa tgattgctgg ggtggcaacg 60
agtaacgcat ttcctttaca tacttttgca gcagaacaaa acgtaaaagt actacaagaa 120
aatgcgaaag attattctct tggtccagca ggattccaag atgtaatggc acaaacaaca 180
tcgagcatat tcgcaatgga ttcatatgca aagttaatcc aaaatcagca agaaacggat 240
ttaagcaaaa taagttcgat taatagtgag tttaaaggaa atatgatgca gcaccaacga 300
gatgcaaaaa ttaacgcggc gtattggtta gatcatatga agccgcaaat tatgaaaacg 360
gatcaaaata ttattaatta caataatact tttcaagcgt attataatag catgttaata 420
gcaattgatc aaaaagatag cgtaaagtta aaagcggatt tagaaaaatt gtatgcggat 480
attgtaaaga atcaaaatga ggtagatgta ttattaggag atttgaaagc ctttcgtgat 540
agaatggcga aagatacaaa tagctttaaa gaggatacaa atcaactaac ctcgattttg 600
gcaagtacga atgctggaat ccccgctcta gagcaacaaa tcaatacata taatgattca 660
atcaaaaaga gtaatgatat ggttattgct ggtggtgtac tttgcgtagc gttaataaca 720
tgtcttgctg gcggacctat gattgccgtt gcgaaaaaag atattgcaaa tgcagaacga 780
gaaatcgcta atttaaaaga tagaatttct ggagcgcaag cagaagtcgc aattttgaca 840
gatgtaaaaa ataaaacaac aaatatgact gaaacgattg atgcagcaat tacagcacta 900
caaaacatat caaatcaatg gtatacagta ggtgcaaaat ataataattt actacaaaac 960
gtaaaaggaa ttagtccgga agagtttacg tttataaaag aagatttgaa tacagcgaaa 1020
gatagttgga aagacgtaaa agattataca gaaaaattac atgaaggcgt agcgaagtaa 1080

<210> SEQ ID NO 59
<211> LENGTH: 1080
<212> TYPE: DNA
<213> ORGANISM: Bacillus thuringiensis

<400> SEQUENCE: 59

```
atgcagaaac gattttataa aaaatgtctt ttaacattaa tgattgctgg agtggcaacg     60
agtaacgcat ttcctttaca tacttttgca gcagaacaaa acgtaaaagt actacaagaa    120
aatgcgaaag attattctct tggtccagca ggattccaag atgtaatggc acaaacaaca    180
tcgagcatat tcgcaatgga ttcatatgca aatttaatcc aaaatcagca agaaacggat    240
ttaagcaaaa taagttcgat taatagtgag tttaaaggga atatgatgca gcaccaacga    300
gatgcaaaaa ttaacgcggc gtattggtta gatcgtatga agccgcaaat tatgaaaacg    360
gatcaaaata ttattaatta caataatact tttcaaacgt attataatag tatgttaata    420
gcgattgatc aaaaggatag tgtaaagtta aaagctgatt tagaaaagtt gtatgccgat    480
attgtaaaga accaaaatga ggtagatgta ttattaaggg atttgaaagc ttttcgtgat    540
agaatggcga aagacacaaa tagttttaag gaagatacaa atcaattaac agcgatttta    600
gcaagtacga atgctggtat tccagcttta gagcaacaaa tcaatacata taatgattca    660
atcaaaaaga gtaatgatat ggtcattgct ggtggtgtac tttgcgtagc gttaataaca    720
tgtcttgctg gcggaccaat gattgccgtc gcgaaaaaag atattgcaaa tgcagaaaga    780
gaaatcgcta atttaaagga tagaatttct ggagcacaag cagaagttgc aattttaact    840
gatgtaaaaa ataaaacaac aaatatgact gaaacgattg atgcagcaat tacagcactg    900
caaaacatat caaatcaatg gtatacggta ggggcaaaat ataataattt actacaaaat    960
gtaaaaggaa tcagctctga agaatttacg tttataaaag aagacttaca tacagcgaaa   1020
gatagctgga aagacgtaaa agattataca gaaaaattac atgaaggtgt ggaaaaataa   1080
```

<210> SEQ ID NO 60
<211> LENGTH: 1080
<212> TYPE: DNA
<213> ORGANISM: Bacillus thuringiensis

<400> SEQUENCE: 60

```
atgcagaaaa gattttataa aaaatgtctt ttagcggtaa tgattgctgg ggtggcaacg     60
agtaacgtat ctcctttaca tccttttgca gcagaacaaa atgtaaaggt actacaagaa    120
agtgtgaaaa actattctct tggaccagct ggattccaag atgtaatggc acaaacgaca    180
tcgagtatat ttgcaatgga ttcatatgca aaattaattc aaaatcaaca agagacggat    240
ttaagtaaaa taagttcgat taatagtgaa tttaaaggga atatgattca gcatcaaaga    300
gatgcaaaaa ttaatgcagc atattggtta aataatatga agcctcaaat tatgaaaacg    360
gatcaaaata ttataaatta caataatact tttcaatcgt attataacga catgttaata    420
gcgattgacc aaaaggatag cggaaaatta aaagcggatt tagaaaagtt gtatgcggat    480
attgtaaaga atcaaaatga ggtagatgga ttattaggaa atttgaaagc ttttcgcgat    540
agaatggcga aagatacaaa tagtttcaaa gaggatacaa atcagttaac agcgatattg    600
gcaagtacga atgctggtat tccagctcta gagcaacaaa taaatacata taacgattcg    660
attaaaaaga gtaatgatat ggtcattgct ggtggcgtac tttgcgtagc gctaataaca    720
tgtcttgctg gcgggccgat gattgcggtt gcaaaaaaag atatcgcaaa tgcagaaaga    780
gagatagcta atttaaaaga tagaatttca ggagcacaag caaaaatcgt aattttgact    840
gatgtaaaaa ataaaacaac aaacatgacg gaaacaattg atgcagcaat tacagcacta    900
caaaacatat caaaccaatg gtatacagta ggtgcaaaat ataataattt actacaaaac    960
gtaaaaggaa ttagtccgga agagtttacg tttataaaag aagatttaca tacagcgaaa   1020
gatagctgga aagatgtaaa ggattataca gaaaaattgc atgaaggtgt ggcgaagtaa   1080
```

<210> SEQ ID NO 61
<211> LENGTH: 1012
<212> TYPE: DNA
<213> ORGANISM: Bacillus cereus

<400> SEQUENCE: 61
atgaaacgtt ctaaaacata tgtaaaatgt ctcgcattat ctgctgtgtt ggcaagtagt 60
gccctagcaa tgcacacacc ggttgtcgct gcacaaacaa cttctcaagt tgtaacagat 120
atcggtcaaa atgcaaaaac acatacaagc tacaatacat ttaataatga acaagcagat 180
aatatgacaa tgtcattaaa agtaactttc attgatgatc caagtgctga taagcaaatt 240
gcggttatta atacaacagg tagctttatg aaagcaaacc caactcttag tgacgcacct 300
gttgatggat atccaattcc aggggcaagt gtcacattgc gctatccatc acaatatgat 360
attgcaatga atttacaaga taatacgtcg cgattctttc atgtagcacc gacaaatgca 420
gtggaagaaa cgactgtcac atcaagcgtt tcttatcaac ttggcggctc tatcaaagcc 480
tctgtaacac caagcggtcc tagtggcgaa tctggagcaa caggtcaagt aacttggtct 540
gattccgtca gttataaaca aacaagctat aaaacaaact taattgatca aacaaataaa 600
catgtaaaat ggaacgtatt ctttaatgga tataataatc aaaactgggg catttacact 660
cgcgattctt accatgcttt atatggaaac caattattta tgtattctcg tacgtatcct 720
catgaaacag atgcacgagg caatctagtc ccaatgaatg accttccagc tctcacaaat 780
agcggtttct ctccaggcat gattgctgtt gtcatttcag aaaaagatac agaacagtct 840
tctatccaag ttgcttatac aaagcatgct gacgattata cacttcgccc tggctttaca 900
ttcggaactg gtaactgggt tggaaataat ataaaagatg tagatcaaaa aacatttaat 960
aaatcatttg tattagattg gaaaaataaa aaactagtag agaagaagta ac 1012

<210> SEQ ID NO 62
<211> LENGTH: 1011
<212> TYPE: DNA
<213> ORGANISM: Bacillus cereus

<400> SEQUENCE: 62
atgaaacgtt ctaaaaccta cttaaaatgt ttagcattat ccgctgtttt tgctagtagt 60
gctgtaactc tttcaacacc tgctacttac gctcaaacga cgtcacaagt tgtaacagat 120
atcgggaaaa atgcaaaaac acatacgagc tataatacat ttaataatga tcaagctgat 180
aatatgacaa tgtctttaaa ggtaactttt atcgatgatc caagcgctga taaacagatt 240
gccgttatta atacaactgg tagttttcta aaagcaaatc ctactataag tgatgcacct 300
attgataact acccaatccc tggcgctagt gcaacattac gttatccttc acaatatgat 360
gttgcattta accttcaaga taacagcgct cgtttcttta acgtagcgcc tacaaatgct 420
gtagaagaaa cgactgtaac atctagcgta tcttatcaac ttggtggctc tgttaaagct 480
tctgtaacgc ctaatggccc tagcggtgaa gctggtgcaa ctggtcaagt cacttggtct 540
gactctgtaa gctataaact aactagttat aaaacaaatt taattgacca aacaaacaaa 600
aacgtaaagt ggaacgtatt ctttaacgga tataacaatc aaaactgggg tatttacaca 660
cgtgactcct atcattcttt atatggaaac caacttttca tgtactctcg cacatacccta 720 tatgaatctg atgcaaaagg taatttaata ccgatggatc aacttccagc attaacaaat 780
agcggtttct ctcctggtat gattgctgtt gttatctctg aaaaaaatac agatcaatct 840
aacttacaag tcgcttatac aaaacacgcc gacgattacc aacttcgtcc aggctacaca 900
ttcggaactg caaactgggt tggaaacaac gtaaaagacg ttgatcaaaa aacatttaac 960
aaattattca cactagattg gaagaataaa aaattggtag agaaaaaata a 1011

<210> SEQ ID NO 63
<211> LENGTH: 1014
<212> TYPE: DNA
<213> ORGANISM: Bacillus cereus

<400> SEQUENCE: 63
atgaaacgct ctaaaacgta tttaaaatgt ttagcattat ccgctgtttt tgctagtagc 60
gctttagcac tttcaacacc tgctgcttac gctcaaacga cgtcacaagt tgtaacagat 120
atcgggcaaa atgcaaaaac acatacgagc tataatacat ttaataatga tcaaactgat 180
aatatgacaa tgtctttaaa ggtaactttt atcgatgatc cgagcgctga taaacagatt 240
gccgttatta atacaactgg tagttttcta aaagcaaatc ctactataag tagtgcgcct 300
attgataact acccaatccc tggcgctagt gcaacattac gctacccttc acaatatgat 360
attgccttta atcttcaaga taacagcgcc cgtttcttta acgtagcacc tacaaatgct 420
gtagaagaaa cgactgtaac ctctagtgta tcttatcaac ttggcggttc tgttaaagct 480
tctgcaacgc caaatggact tagcgctgaa gcgggtgcaa ctggccaagt aacttggtct 540
gactctgtaa gctataaaca aactagttat aaaacaaact taattgacca aacaaataaa 600
aacgtaaaat ggaacgtatt ctttaacgga tataacaatc aaaactgggg tatttacaca 660
cgtgattcct accattcttt atatggaaac caactgttca tgtactctcg cacatactta 720
tatgaatctg atgcaaaagg taatttaata ccgatggatc aacttccagc attaacaaat 780
agtggtttct ctcctggtat gatcgctgtt gttatctctg aaaaaaatac agaccaatct 840
aacctacaag tcgcttatac aaaacacgcc gacgactacc aacttcgtcc aggcttcaca 900
ttcggaactg caaactgggt tggaaacaac gtaaaagatg ttgatcaaaa aacatttaat 960
aaatcgttta cattagattg gaagaataag aaattagtag agaaaaatag ataa 1014

<210> SEQ ID NO 64
<211> LENGTH: 1011
<212> TYPE: DNA
<213> ORGANISM: Bacillus cereus

<400> SEQUENCE: 64
atgaaacgct ctaaaacgta tttaaaatgt ttagcattat ccgctgttgt tgctagtagc 60
gctttagcac tttcaacacc tgctgcttac gctcaaacga cgtcacaagt tgtaacagat 120
atcgggcaaa atgcaaaaac acatacgagc tataatacat ttaataatga tcaaactgat 180
aatatgacaa tgtctttaaa ggtaactttt atcgatgatc cgagcgctga taaacagatt 240
gccgttatta atacaactgg tagttttcta aaagcaaatc ctactataag tagtgcgcct 300
attgataact acccaatccc tggcgctagt gcaacattac gctacccttc acaatatgat 360
attgccttta atcttcaaga taacagcgcc cgtttcttta acgtagcacc tacaaatgct 420
gtagaagaaa cgactgtaac ctctagtgta tcttatcaac ttggcggttc tgttaaagct 480
tctgcaacgc caaatggacc tagcgctgaa gcgggtgcaa ctggccaagt aacttggtct 540
gactctgtaa gctataaaca aacaagttat aaaacaaact taattgacca aacaaataaa 600
aacgtaaaat ggaatgtatt ctttaacgga tataacaatc aaaactgggg tatttacaca 660
cgtgattcct accattcttt atacggaaac caactgttca tgtactctcg cacatactta 720

-continued

```
tatgaatctg atgcaaaagg taatttaata ccgatggatc aacttccagc attaacaaat    780

agcggtttct ctcctggtat gatcgctgtt gttatctctg aaaaaaatac agaccaatct    840

aacctacaag tcgcttatac aaagcacgcc gacgactacc aacttcgtcc aggctacaca    900

ttcggaactg caaactgggt tggaaacaac gtaaaagatg ttgatcaaaa aacatttaat    960

aaatcgttta cattagattg gaagaataag aaattagtag agaaaaaata g            1011
```

<210> SEQ ID NO 65
<211> LENGTH: 1011
<212> TYPE: DNA
<213> ORGANISM: Bacillus cereus

<400> SEQUENCE: 65

```
atgaaacgtt ctaaaaccta cttaaaatgt ttagcattat ccgctgtttt tgctagtagt     60

gctgtaactc tttcaacacc tgctacttac gctcaaacga cgtcacaagt tgtaacagat    120

atcgggcaaa atgcaaaaac acatacgagc tataatacat ttaataatga tcaagctgat    180

aatatgacaa tgtctttaaa ggtaactttt atcgatgatc caagcgctga taaacagatt    240

gccgttatta atacaactgg tagttttcta aaagcaaatc ctactataag tgatgcacct    300

attgataact acccaatccc tggcgctagt gcaacattac gttatccttc acaatatgat    360

gttgcattta accttcaaga taacagcgct cgtttcttta acgtagcgcc tacaaatgct    420

gtagaagaaa cgactgtaac atctagcgta tcttatcaac ttggtggctc tgttaaagct    480

tctgtaacgc ctaatggccc tagcggtgaa gctggtgcaa ctggtcaagt cacttggtct    540

gactctgtaa gctataaaca aactagttat aaaacaaatt taattgacca aacgaacaaa    600

aacgtaaaat ggaacgtatt ctttaacgga tataacaatc aaaactgggg tatttacaca    660

cgtgactcct atcattcttt atatggaaac caacttttca tgtactctcg cacataccta    720

tatgaatctg atgcaaaagg taatttaata ccaatggatc aacttccagc attaacaaat    780

agcggtttct ctcctggtat gattgctgtt gttatctctg aaaaaaatac agatcaatct    840

aacttacaag tcgcttatac aaaacacgcc gatgactacc aacttcgtcc aggcttcaca    900

ttcggaactg caaactgggt tggaaacaac gtaaaagacg ttgatcaaaa aacatttaat    960

aaattgttca cactagattg gaagaataag aaattggtag agaaaaaata a            1011
```

<210> SEQ ID NO 66
<211> LENGTH: 1011
<212> TYPE: DNA
<213> ORGANISM: Bacillus thuringiensis

<400> SEQUENCE: 66

```
atgaaacgct ctaaaacgta tttaaaatgt ttagcattat ccgctgtttt tgctagtagc     60

gctttagcac tttcaacacc tgctgcttac gctcaaacga cgtcacaagt tgtaacagat    120

atcgggcaaa atgcaaaaac acatacgagc tataatacat ttaataatga tcaaactgat    180

aatatgacaa tgtctttaaa ggtaactttt atcgatgatc caagcgctga taaacagatt    240

gccgttatta atacaactgg tagttttcta aaagcaaatc ctactataag tagtgcgcct    300

attgataact acccaatccc tggcgctagt gcaacattac gctatccttc acaatatgat    360

attgccttta atcttcaaga taacagcgct cgtttcttta acgtagcacc tacaaatgct    420

gtagaagaaa cgactgtaac ctctagtgta tcgtatcaac ttggcggttc tgttaaagct    480

tctgcaacgc caaatggacc tagcgctgaa gcgggtgcaa ctggtcaagt aacttggtct    540
```

-continued

```
gactctgtaa gctataaaca aactagttat aaaacaaact taattgacca aacaaataaa    600

aacgtaaaat ggaacgtatt ctttaacgga tataacaatc aaaactgggg tatttacaca    660

cgtaattcct accattcttt atatggaaac caactgttca tgtactctcg cacatactta    720

tatgaatctg atgcaaaagg taatttaata ccgatggatc aacttccagc gctaacaaat    780

agtggtttct ctcctggtat gatcgctgtt gttatctctg aaaaaaatac agaccaatct    840

aacctacaag tcgcttatac aaaacacgcc gacgactacc aacttcgtcc aggcttcaca    900

ttcggaactg caaactgggt tggaaacaac gtaaaagatg ttgatcaaaa aacatttaat    960

aagttgttca cactggattg gaagaataag aaattagttg agaaaaaata a            1011
```

<210> SEQ ID NO 67
<211> LENGTH: 18
<212> TYPE: DNA
<213> ORGANISM: Artificial Sequence
<220> FEATURE:
<223> OTHER INFORMATION: Synthetic Primer

<400> SEQUENCE: 67
caagagctgt cacgaatc 18

<210> SEQ ID NO 68
<211> LENGTH: 19
<212> TYPE: DNA
<213> ORGANISM: Artificial Sequence
<220> FEATURE:
<223> OTHER INFORMATION: Synthetic Primer

<400> SEQUENCE: 68
ctgcttgatt agcacgatc 19

<210> SEQ ID NO 69
<211> LENGTH: 20
<212> TYPE: DNA
<213> ORGANISM: Artificial Sequence
<220> FEATURE:
<223> OTHER INFORMATION: Synthetic Primer

<400> SEQUENCE: 69
cctatcaata ctctcgcaac 20

<210> SEQ ID NO 70
<211> LENGTH: 20
<212> TYPE: DNA
<213> ORGANISM: Artificial Sequence
<220> FEATURE:
<223> OTHER INFORMATION: Synthetic Primer

<400> SEQUENCE: 70
catcaggtca tactcttgtg 20

<210> SEQ ID NO 71
<211> LENGTH: 19
<212> TYPE: DNA
<213> ORGANISM: Artificial Sequence
<220> FEATURE:
<223> OTHER INFORMATION: Synthetic Primer

<400> SEQUENCE: 71
cctggtagaa tcgtacaag 19

<210> SEQ ID NO 72
<211> LENGTH: 20

<212> TYPE: DNA
<213> ORGANISM: Artificial Sequence
<220> FEATURE:
<223> OTHER INFORMATION: Synthetic Primer

<400> SEQUENCE: 72
gagctgcatt ctcaatatgc 20

<210> SEQ ID NO 73
<211> LENGTH: 19
<212> TYPE: DNA
<213> ORGANISM: Artificial Sequence
<220> FEATURE:
<223> OTHER INFORMATION: Synthetic Primer

<400> SEQUENCE: 73
gcaagtccga atgtacaac 19

<210> SEQ ID NO 74
<211> LENGTH: 21
<212> TYPE: DNA
<213> ORGANISM: Artificial Sequence
<220> FEATURE:
<223> OTHER INFORMATION: Synthetic Primer

<400> SEQUENCE: 74
cttcgagttg agttgttaca c 21

<210> SEQ ID NO 75
<211> LENGTH: 19
<212> TYPE: DNA
<213> ORGANISM: Artificial Sequence
<220> FEATURE:
<223> OTHER INFORMATION: Synthetic Primer

<400> SEQUENCE: 75
ctgctacgaa tggtagtac 19

<210> SEQ ID NO 76
<211> LENGTH: 20
<212> TYPE: DNA
<213> ORGANISM: Artificial Sequence
<220> FEATURE:
<223> OTHER INFORMATION: Synthetic Primer

<400> SEQUENCE: 76
cttgatccac tgtctgatac 20

<210> SEQ ID NO 77
<211> LENGTH: 20
<212> TYPE: DNA
<213> ORGANISM: Artificial Sequence
<220> FEATURE:
<223> OTHER INFORMATION: Synthetic Primer

<400> SEQUENCE: 77
cctgacaaca actactgtag 20

<210> SEQ ID NO 78
<211> LENGTH: 18
<212> TYPE: DNA
<213> ORGANISM: Artificial Sequence
<220> FEATURE:
<223> OTHER INFORMATION: Synthetic Primer

<400> SEQUENCE: 78
gtctttcgct gcattcag 18

<210> SEQ ID NO 79
<211> LENGTH: 18
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (13)..(13)
<223> OTHER INFORMATION: R = A or G

<400> SEQUENCE: 79
gttaggatca cartcacc 18

<210> SEQ ID NO 80
<211> LENGTH: 18
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (8)..(8)
<223> OTHER INFORMATION: R = A or G

<400> SEQUENCE: 80
tcgtttgrct atctgcag 18

<210> SEQ ID NO 81
<211> LENGTH: 20
<212> TYPE: DNA
<213> ORGANISM: Artificial Sequence
<220> FEATURE:
<223> OTHER INFORMATION: Synthetic Primer

<400> SEQUENCE: 81
gatacagcta gaggaaatgc 20

<210> SEQ ID NO 82
<211> LENGTH: 20
<212> TYPE: DNA
<213> ORGANISM: Artificial Sequence
<220> FEATURE:
<223> OTHER INFORMATION: Synthetic Primer

<400> SEQUENCE: 82
gatcccattg tgtaccattg 20

<210> SEQ ID NO 83
<211> LENGTH: 19
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (5)..(5)
<223> OTHER INFORMATION: W = T or A

<400> SEQUENCE: 83
cagcwggatt ccaagatgt 19

<210> SEQ ID NO 84
<211> LENGTH: 18
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (4)..(4)
<223> OTHER INFORMATION: R = A or G

<400> SEQUENCE: 84
ccarctatct ttcgctgt 18

<210> SEQ ID NO 85
<211> LENGTH: 19
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (3)..(6)
<223> OTHER INFORMATION: W = T or A; R = A or G

<400> SEQUENCE: 85
gcwgtrgaag aaacgactg 19

<210> SEQ ID NO 86
<211> LENGTH: 20
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (12)..(13)
<223> OTHER INFORMATION: W = T or A; S = C or G

<400> SEQUENCE: 86
ccaacccagt twscagttcc 20

<210> SEQ ID NO 87
<211> LENGTH: 3551
<212> TYPE: DNA
<213> ORGANISM: Bacillus thuringiensis

<400> SEQUENCE: 87
tcctatcaat actctcgcaa caccaatcgt tcaagcagaa actcaacaag aaaacatgga 60
tatttcttca tcattacgaa aattaggtgc gcattctaaa ttagtccaaa cgtatattga 120
tcaatcttta atgagtccta atgtacagct agaggaagtc ccagctttaa ataccaatca 180
attcctaatc aaacaagata tgaaggaatg gtcatcggaa ctctatccac agttaattct 240
attaaattca aaaagtaaag gatttgtaac aaaatttaat agttattacc cgacattaaa 300
atcgtttgta gacaataaag aagatagaga agggttttcg gatagacttg aagtacttca 360
agaaatggct atgacgaatc aagaaaatgc gcaacgacaa atcaatgaat taacagatct 420
taaattacag cttgataaaa aattaaaaga ttttgatact aatgtggcaa ctgcgcaagg 480
catactaagt acagatggaa caggaaaaat agatcagtta aaaaatgaaa tattaaatac 540
caaaaaagca attcaaaatg atttacagca aattgcatta ataccaggag ctttaaatga 600
gcagggattt gctatattca aagaagttta tagtctttca aaagaaatta ttgaaccggc 660
tgctcaagca ggggtggcag cgtataacaa aggaaaagaa attaacaact ctattctaga 720
agcggagaaa aaagcggcgc aagaagcgac agaacaaggt aaaactgctc tagagattga 780
atcagcaaaa aaagcagctc gtgaagcaat tgagaaaagc aaacaaggtg aaatagcagc 840

-continued

```
cgcagccgca gcaaaaacac aagagtatga cctgatgaaa gccattgata ccgaaaagat    900
taagaaaaca tttggcgttt ttgctgaagt aaataaatta acagcagaac agcgagcata    960
tttagatgat ttagagaaac aaaatcaaaa aatatatgat ttaacaacga aattatcaat   1020
agctgattta caaaaatcaa tgcttcttct tacacaaaat gatttgcata cgtttgcaaa   1080
tcaagtagat gtagaacttg atctactaaa gcgctataaa gaagatttaa atctaataaa   1140
aaatagcatt acaaaattat ctactaatgt tgatacaact aacgagcagt ctcaaaaaga   1200
tacattaaga caattaaaaa atgtaataag ttaccttgaa gaacaagtat ataaatttta   1260
atattgcgtt ttttgggaat ccataaagat tataagcatt tagcgaaaga aggagaatag   1320
tcatgaaaaa atttccattc aaagtactaa ctttagctac attagcaact gttataactg   1380
ctactaccgg taacactatt catgcatttg cacaagaaac gaccgctcaa gaacaaaaag   1440
taggcaatta tgcattaggc cccgaaggac tgaagaaagc attagctgaa acagggtctc   1500
atattctagt aatggattta tacgcaaaaa caatgattaa gcaaccaaat gtaaatttat   1560
ctaatatcga tttaggctca gagggggggag agttgctcaa aaatattcac cttaatcaag   1620
agctgtcacg aatcaatgcg aattactggt tagatacagc gaagccacag attcaaaaaa   1680
ctgctcgtaa tattgtaaat tacgatgaac aatttcaaaa ttattacgac acattagtag   1740
aaactgtaca aaagaaagat aaggcaggtc taaaagaggg tataaatgat ttaattacta   1800
caatcaatac aaattcaaaa gaagttacag atgtgattaa gatgctacaa gacttcaaag   1860
ggaaattata tcaaaattct acagatttta aaaataatgt tggtggtcca gatgggaaag   1920
gtggattaac tgcaatatta gcaggtcaac aggcaacgat tccacaactt caagctgaaa   1980
ttgagcaact tcgttctact cagaaaaaac attttgatga tgtattagca tggtcaattg   2040
gtggtggatt gggagcagct attttagtta ttgcagctat tggaggagcg gtagttattg   2100
ttgtaactgg cggtacagca acaccggctg ttgttggtgg actctcggct cttggcgcag   2160
ctggtatcgg tctaggaact gcggctggtg tcacagcatc taagcatatg gattcctata   2220
atgaaatttc taacaaaatc ggagaattaa gtatgaaagc agatcgtgct aatcaagcag   2280
ttctttcgct tactaacgcg aaagaaacat tggcatattt ataccagact gtagatcaag   2340
cgatattgtc tctaacaaat attcaaaagc aatggaatac aatgggcgca aattatacag   2400
atttattgga taatatcgat tctatgcaag accacaaatt ctctttaata ccagatgatt   2460
taaaagcggc taaagaaagt tggaatgata ttcataaaga tgcagaattc atttcaaaag   2520
atattgcttt taaacaggag tagaactgaa atttaaaacc taaattggag gaaaatgaaa   2580
tgataaaaaa aatcccttac aaattactcg ctgtatcgac actattaact attacaactg   2640
ctaatgtagt ttcaccagta acaacttttg caagtgaaat tgaacaaacg aataatggag   2700
atacggctct ttctgcaaat gaagcgagaa tgaaagagac cttgcaaaag gctggattat   2760
ttgcaaaatc tatgaatgcc tattcttata tgttaattaa gaatcctgat gtgaattttg   2820
agggaattac cattaatgga tatgtagatt tacctggtag aatcgtacaa gatcaaaaga   2880
atgcaagggc acatgccgtt acttgggata cgaaagtaaa aaaacagctt ttagatacat   2940
tgaatggtat tgttgaatac gatacaacat ttgataatta ttatgaaaca atgatagagg   3000
cgattaatac aggggatgga gaaactttaa aagaagggat tacagattta cgaggtgaaa   3060
ttcaacaaaa tcaaaagtat gcacaacaac taatagaaga attaactaaa ttaagagact   3120
ctattggaca cgatgttaga gcatttggaa gtaataaaga gctcttgcag tcaattttaa   3180
aaaatcaagg tgcagatgtt gatgccgatc aaaagcgtct agaagaagta ttaggatcag   3240
```

taaactatta taaacaatta gaatctgatg ggtttaatgt aatgaagggt gctattttgg 3300
gtctaccaat aattggcggt atcatagtgg gagtagcaag ggataattta ggtaagttag 3360
agcctttatt agcagaatta cgtcagaccg tggattataa agtaacctta aatcgtgtag 3420
ttggagttgc ttacagtaat attaatgaaa tgcacaaggc gcttgatgat gctattaacg 3480
ctcttactta tatgtccacg cagtggcatg atttagattc tcaatattcg ggcgttctag 3540
ggcatattga g 3551

<210> SEQ ID NO 88
<211> LENGTH: 3409
<212> TYPE: DNA
<213> ORGANISM: Bacillus thuringiensis

<400> SEQUENCE: 88
actcatttct attaaacaag atatgaaaga gtggtcatcc gaactttatc ctaaattaat 60
tctattaaat tcaaaaagta aaggatttgt aactaaattt aatagttatt atccaacatt 120
aaaaggattt gtagataata aggaagataa agaagggttt acagatagac tggaagtcct 180
tcaagacatg accatcacaa accaagaaag tgtgcaacgt caaattaatg agttaacaga 240
tctaaaacta caggtagata agaagttgaa aaatcttgat actgatgtgg caaaaacaca 300
gagtgtcctt aattcagagg gaacaggaaa aatagataag ttaaaaaatg aaatgctaga 360
tacaaaaaaa tcaattcaaa atgatttaca gcaaatagcg ttattaccag gagctttaaa 420
tgaacaagga ctaaaggtat tccaagaaat ttatagtcta tcaaaagata tcattgaacc 480
ggctgctcaa acagcagtag tagcgtataa caaaggaaaa gaaataaaca atgctattgt 540
agacgcagag aataaagcag agcaagaagc aaaagaaaaa ggaaaatcag ctatagaaat 600
tgaggctgcc aaaaaagaag cacgtgaagc gatagagaaa agtaaaaaag gtgaaatcgc 660
tgcagctgca gttacaaaaa cgaaagagta tgatcttatg aaagtaattg atcctgaaaa 720
aattaaaaaa acatataata cttttgctga aattaataaa ctaacagcag agcaacgtgc 780
atatttaaat gatttagaga aacaaaatca gaaattatat gacttaacga ctaaattaac 840
agtagcagat ttacaaaaat caatgattct tttcatgcaa aatgatttgc atacatttgc 900
taaccaagta gatggagaaa ttgagctaat gaaacgttac aaagaggatt tggatctaat 960
aaataatagt attacaaaat tatcgactga agttgatacc aataacaccc agtctcaaaa 1020
agatacatta agacgattaa aaagtgtaac aactcaactc gaagaacaag tttataaatt 1080
ttaatattaa gaaattaggt ttaataaaaa tattataacg caactgaaaa taaggaggag 1140
aatcaaatga tgaaatttcc atttaaggtt ataactttag ccactttagc aacggttata 1200
actgctacga atggtagtac tattcatgca cttgcacaag aacagacagc tcaagaacat 1260
aaaatagaaa attatgcgtt aggacctgaa gggttaaaga aagcgttggc tgcaactggc 1320
tctcatattc ttgtaatgga tttgtacgca aaaactatga ttaagcaacc gaatgtaaat 1380
ttatccaaca ttgatttagg ttcaggagga ggagaattaa tcaaaaatat ccacctgaat 1440
caggaactgt cacgaatcaa tgcaaattac tggttagata cagcgaagcc aaacattcaa 1500
aaaacagctc gtaatattgt aaattatgat gagcaattcc aaaattatta cgacacatta 1560
gtagatactg taaaaaagaa agataagatg agccttaaag aaggaatagg ggatttaatc 1620
gatacaattc atacaaattc aaatgaagtt actgacgtca ttaagatgtt agaggctttc 1680
aaaacaaagt tgtatacaaa tactgtagat tttaaaaata atgttggtgg tccagatgga 1740

-continued

```
cagggaggat tgacggctat attagcggga aaacaagcac tagtcccaca acttcaggcc   1800
gaaattgaga atttacgttc tacacagaaa tcacattttg ataatgtatt agcctggtca   1860
attggcggtg gactaggagc agctatttta gttattggaa cgattgcagg agcggtagta   1920
attgttgtga ctggtggtac agctacacca gctgttgttg gcggtcttac agctctagga   1980
gcagctggta tcggtttagg aacagcagct ggtgtcgagg catctaatca tatgaattct   2040
tataatgaaa tttcgaataa aatcggagaa ttaagtatga aagctgatct ggctaatcaa   2100
gcggttattt cacttactaa tacgaaagac actctaacat atttgtatca gacagtggat   2160
caagcaataa tgtctctaac aagtattcag caacaatgga ataaaatggg ggctaattat   2220
aaagatttat atgataatat cgatcaaatg caagaacata aactttcgtt aatacctgac   2280
gatttaaaag ctgctaaaca aagttggaat gacattcata aggacgcaga attcatttca   2340
aaagacattg cttttaaaca agaaaaaaca aactaaaaat taatatatat tcataggagg   2400
aattaaagtg aataataatt ttccttataa actacttgct gtatcgacgt ttttaaccct   2460
gacaacaact actgtagttt caccagtagc tgcttttgca agtgaaagta aaatagaaca   2520
aaccagtacg gaagatatat ctctttctgt aaacagtgaa aagatgaaaa aagctttgca   2580
agatgctggg gtatttgcaa aatccatgaa tgattactct tatttgttaa ttaataatcc   2640
agatgttaac tttgaaggaa ttgatattaa aggatataca aatctaccta gtcaaattgc   2700
acaagatcaa aagaatgcaa gagagcatgc tacaaaatgg gatgctcaca taaaaaaaca   2760
acttttagat acccttacag gaattgtaga gtatgatacc acatttgaca attattacga   2820
tacattagta gaagcaatta atgaaggaga tgcagataca ttaaaagaag gcattacaga   2880
tttacaaggt gagattaaac aaaaccaagc atatacacag aatttaattc aagaactagc   2940
taagttaaga gatagtattg gagaagatgt ccgagcattt ggaggtcata aagatatctt   3000
gcaatcgatt ttaaaaaatc aagcatctgg aatagatgaa gatgaaaaac gcctaaatga   3060
tgttttagag caaataagac attttaaaca agtagaatcg gatggaataa taactgtatc   3120
atatccttca atccctacat ggattgctgg aggtgtgatg atagggggtag caagaaataa   3180
tttaggtacg ttagagccgt tattagtgca attacgccaa accgtagact ataaaataac   3240
attaaatcgt gtagttggag ttgcgtataa taatattact gaaatgcaaa atgcaattgg   3300
atcagctatt aatgctctta cctatatgtc agcacaatgg catgatttag attctcaata   3360
ttcaggagtg cttaatcata ttgataaagc atcccaaaaa gcagatcaa               3409
```

<210> SEQ ID NO 89
<211> LENGTH: 3409
<212> TYPE: DNA
<213> ORGANISM: Bacillus thuringiensis

<400> SEQUENCE: 89

```
tctaattaaa caagatatga aagagtggtc atccgaactt taccctaaat taattctatt     60
aaattcaaaa agtaaaggat ttataactaa atttaatagt tattatccaa cattaaaagg    120
atttgtagat aataaggaag ataaagaagg gtttacagat agactggaag ttcttcaaga    180
catgactata acaaatcaag aaagtgtgca acgtcaaatt aatgagttaa cagatttaaa    240
attactggta gataagaagt tgaaaaacct tgatactgat gtggtaaaag cacaaagtgt    300
ccttaattca gagggaacag gaaaaataga taagttaaaa aatgaaatgc tagatacaaa    360
aaaatctatt caaaatgatt tgcagcaaat agcattatta ccaggcgcgt taaatgaaca    420
agggctaaag gtattccaag aaatttatag tctatcgaaa gatatcattg aaccggctgc    480
```

-continued

```
tcaaacagca gtagtagcgt ataacaaagg aaaagaaata aacaatgcca ttgtagacgc    540
agagaagaaa gcagagcaag aagcaaaaga aaagggaaaa tcagctatag aaattgaagc    600
tgccaaaaaa gaagcacgtg aaacgataga gaaaagtaaa aaaggtgaaa tcgctgcagc    660
tgcagttaca aaaacgaaag agtatgatct tatgaaagtg attgatcctg aaaaaataaa    720
aaaaacatat aatacttttg ctgaaattaa taaactaaca gctgagcaaa gagcatattt    780
aaatgattta gagaaacaaa atcagaaatt atatgactta acaactaaat taacagtagc    840
agatttacaa aaatcaatga ttcttttcat gcaaaatgac ttgcatacat ttactaatca    900
agtagatgga gaaattgagt taatgaaacg ttacaaagag gatttggatc taataaataa    960
tagtattaca aaattatcga ctgaagttga taccaataat actcaggctc aaaaagatat   1020
attaagacga ttaaaaagtg taacaattca acttgaagaa caagtttata aattttgata   1080
ttaagaaatt aggtttatta aaaaattata acgaaacgga aaataaggag gagaatcaaa   1140
tgatgaaatt tccatttaaa gttataacct tagctacttt agcaacgatt ataaccgcta   1200
caaatggtag tactattcat gcacttgcac aagaacagac agctcaagaa cagaaaatag   1260
aaaattatgc gttaggacct gaaggattaa agaaagcgtt ggctgaaaca ggctctcata   1320
ttcttgtaat ggatttgtac gcaaaaacta tgattaagca accgaatgta aatttatcca   1380
acattgattt aggttcgggt ggagaagaat taatcaaaaa tattcacctg aatcaagaac   1440
tgtcacgaat caatgcaaat tactggttag atacagcgaa gccaaacatt caaaaaacag   1500
cacgtaatat tgtaaattat gatgagcaat ttcaaaatta ttacgacaca ttagtagata   1560
ctgtaaaaaa gaaggataag gtgagcctca aagaaggaat aggggattta atctatacaa   1620
ttcatacaaa ttcaaatgaa gttacggaag tcattaagat gttagaggct ttcaaaacaa   1680
agttgtatac aaatactgta gattttaaaa ataatgttgg tggtccagat ggacagggag   1740
gattgacggc tatattagcg ggaaaacaag cgctagtccc acaacttcag gccgaaattg   1800
agaatttacg ttctacacag aaaacacatt ttgataatgt attagcctgg tcaattggtg   1860
gtggattagg agcagctatt ttagttattg gaacgattgc aggagcggta gtaattgttg   1920
tgactggtgg tacagctacg ccagctgttg ttggtggtct tacagctcta ggagccgctg   1980
gtatcggttt aggaacagca gctggcgtcg aggcatctaa tcatatgaat tcttataatg   2040
aaatttcgaa taaaatcgga gaattaagta tgaaagctga tttggctaat caagcggtta   2100
tttcacttac taatacgaaa gacactctaa catatttgta tcagacagtg gatcaagcaa   2160
taatgtctct aacaagtatt cagcaacaat ggaataaaat ggggggctaat tataaagatt   2220
tatatgataa tatcgatcaa atgcaagaac ataaactttc gttaatacct gacgatttaa   2280
aagctgctaa acaaagttgg aatgatattc ataaggatgc agaattcatt tcaaaagaca   2340
ttgcttttaa acaagaaaaa acaaactaga aattaatata tattcatagg aggaattaaa   2400
gtgaataata attttcctta taaactactt gctgtatcga cgtttttaac cctgacaaca   2460
actactgtag tttcaccagt agctgctttt gcaagtgaaa gtaaaataga acaaaccagt   2520
acggaagata tatctctttc tgtaaacagt gaaaagatga aaaaagcttt gcaagatgct   2580
ggggtatttg caaaatccat gaatgattac tcttatttgt taattaataa tccagatgtt   2640
aactttgaag gaattgatat taaaggatat acaaatctac ctagtcaaat tgcacaagat   2700
caaaagaatg caagagagca tgctacaaag tgggatgcgc acataaaaaa acaactttta   2760
gatactctta caggaattgt agagtatgat actacatttg acaattatta cgatacatta   2820
```

-continued gtagaagcaa ttaatgaagg agatgcagat acattaaaag aaggcattac agatttacaa 2880
ggtgagatta aaaaaaacca agcatataca aagaatttaa tacaagaact agctaagtta 2940
agagatagta ttggagaaga tgtccgagca tttggaggtc ataaagatat cttgcaatcg 3000
attttaaaaa atcaagcatc tggaatagat gaagatgaaa aacgtctaaa tgatgtttta 3060
gagcaagtaa gacattttaa acaagtagaa tcggatggaa taataactgt atcagttccc 3120
tcaatcccta catggattgc tggaggtgta atgatagggg tagcaagaaa taatttaagt 3180
acgctggaac cgctattagc gcaattgcgc caaacggtag actataaaat tacattgaat 3240
cgtgtagttg gagttgcgta taataatatt gctgaaatgc aaaatgcaat tggatcagct 3300
attaatgctc tcacctatat gtcagcacaa tggcatgatt tagattctca atattcagga 3360
gtacttaatc atattgataa agcatcccaa aaagcagatc aaaataatt 3409

<210> SEQ ID NO 90
<211> LENGTH: 3345
<212> TYPE: DNA
<213> ORGANISM: Bacillus thuringiensis

<400> SEQUENCE: 90
atattatttt gcacagccag acattaaggt aaatgcgatg agtagcttag cgaatcatca 60
aaagtttgca aaggcgaatg tacgagagtg gattgatgaa tataatccga agctaattga 120
cttaaatcaa gagatgatga gatacagcac tagattcaat agttattata gtaagctcta 180
tgaactagca ggaaatgtaa atgaagatca gcaagcaaaa acagatttta tgagtgcata 240
tggaaaatta caattgcaag tacagagcat ccaagagagt atggagcaag atttattaga 300
gttaaatcga tttaaaacag tattagacaa agatagtaac aacttatcaa ttaaagccga 360
tgaagcaata aaaacactgc aaggatcaag tggagatatt gtgaaattaa gagaagatat 420
taaaagaatt caaggggaaa ttcaagctga actaactact attttgaata gacctcaaga 480
aataattaaa ggttctatta atatcggtaa acaagtattt acaatcacaa atcaaactgc 540
acaaacgaaa acaatcgatt ttgtttctat cggtacttta agtaatgaaa ttgtaaatgc 600
tgcagatagt caaacgagag aagcagcttt tcgcattcag caaaagcaaa aagagttatt 660
gccacttatt caaaagttat cacaaactga agcagaggcg actcaaatta cattcgttga 720
agatcaagta aatagcttta cagaattaat tgatcgtcaa attacaactt tagaaacgtt 780
attaacggat tggaaagttt taaataataa tatgattcaa attcaaacaa atgttgaaga 840
aggcacgtat acagacagta gtttacttca aaaacatttt aatcaaatta aaaaagtaag 900
tgatgaaatg aataagcaaa caaatcaatt tgaagattac gttacaaacg ttgaagtaca 960
ttaaatagaa aaataattag cgatataggg agagaagaaa aatgacaaaa aaaccatata 1020
aagtaatggc tctatcagca cttatggcag tatttgcagc aggaaatatt atgccggctc 1080
atacgtatgc agctgaaagt acagtgaaac aagctccagt tcatgcggta gcaaaagctt 1140
ataataacta tgaagaatat tcattaggac cagaaggttt gaaagatgca atggaaagaa 1200
caggttcaaa tgctttagta atggatctgt atgctttaac aattattaaa caaggtaatg 1260
ttaactttgg aaatgtatcg actgttgatg cagctttaaa aggaaaagtg attcagcacc 1320
aagatacagc tagaggaaat gcgaagcaat ggttagatgt attaaagcca cagcttattt 1380
caacgaatca aaacatcatt aactacaata caaaattcca aaactattat gatactttag 1440
ttgctgcggt agatgcaaaa gataaagcga ctcttacgaa aggcctaact agattatcaa 1500
gtagtattaa tgaaaataaa gcgcaagtgg atcagttagt agaagacttg aaaaaattcc 1560
gaaataaaat gacgtcggat acgcaaaact tcaagggtga tgcaaatcaa attacatcta 1620
tattagctag tcaagatgca gggattccac ttctgcaaaa tcaaattaca acgtacaatg 1680
aagcaattag taaatataat gcaattatta tcggttcatc tgttgcgaca gctctaggac 1740
caattgcaat tattggtggt gcagtagtta ttgctacggg cgcaggaaca ccgctaggag 1800
tcgcattaat tgcaggtggt gcagcagctg taggcggtgg tacagctggt atcgtattag 1860
cgaagaaaga acttgacaat gcacaagctg aaattcaaaa aataactgga caaattacaa 1920
ctgctcaatt agaagtagct gggttaacga acattaaaac acaaactgag tatttaacaa 1980
atacgattga tactgcaatt acagcgttgc aaaacatttc aaaccaatgg tatacaatgg 2040
gatcaaaata caattcttta cttcaaaatg tggattcaat tagtccaaac gatcttgttt 2100
tcattaaaga agatttaaac attgcgaaag atagctggaa aaacattaaa gactatgcag 2160
aaaagattta tgctgaagat attaaagtag tagatacgaa aaaagcataa tcgaatacga 2220
atcgttaggg cgttaagtgt tgatgaatga tttgaagctc ctgttcagtt gtgagcagga 2280
gcttttgata tccttataaa gagaataggt gaaaaatatg cagaaacgat tttataaaaa 2340
atgtctttta gcggtaatga ttgctggggt ggcaacgagt aacgcatttc ctttacatcc 2400
ttttgcagca gaacaaaatg taacggtgct acaagaaaat gtgaaaaact attctcttgg 2460
accagcagga ttccaagatg taatggcaca aacgacatca agcatatttg caatggattc 2520
atatgcaaaa ttaattcaaa atcaacaaga gacggattta agtaaaataa gttcgattaa 2580
tagtgaattt aaagggagta tgattcagca tcaaagagat gcaaaaatta atgcagcata 2640
ttggttaaat aatatgaagc ctcaaattat gaaaacagat caaaatatta taaattacaa 2700
taatactttt caatcgtatt ataatgacat gttaatagcg attgatcaaa aggatagtgg 2760
aaaattaaaa gcggatttag aaaagttgta tgcggatatt gtaaagaatc aaaatgaggt 2820
agatggatta ttaggaaatt tgaaagcttt tcgcgataga atggcgaaag atacaaatag 2880
tttcaaagag gatacaaatc agttaacagc gatattggca agtacgaatg ctggtattcc 2940
agctctagag caacaaataa atacatataa cgattcgatt aaaaagagta atgatatggt 3000
cattgctggt ggcgtacttt gcgtagctct aataacatgt cttgctggcg ggccgatgat 3060
tgcggttgcg aaaaaagata tcgcaaatgc agaaagagaa atcgccaatt taaaagatag 3120
aatttcagga gcacaagcag aagtcgtaat tttgactgat gtaaaaaata aaacaacaaa 3180
catgacagaa acaattgatg cagcaattac agcactacaa aacatatcaa atcaatggta 3240
tacagtaggt gcaaagtata ataatttatt acaaaacgta aaaggaatta gtccggaaga 3300
gtttacgttt ataaaagaag atttacatac agcgaaagat agctg 3345

<210> SEQ ID NO 91
<211> LENGTH: 1107
<212> TYPE: DNA
<213> ORGANISM: Bacillus thuringiensis

<400> SEQUENCE: 91
atgcaattat gcataaccat ccattccgtt ttattttcat gttacgatat aaatgtaata 60
cgacatatat cgacaaagat aaaaggaagt gattgtatga aacgttctaa aacatactta 120
aaatatttag cattatccgc tgtttttgct agtagtgcta taactctttc aacacctgct 180
gcttacgctc aaacaacatc acaagttgta acagatatcg ggcaaaatgc aaaaacacat 240
acgagctata atacatttaa taatgatcaa gctgataata tgacaatgtc tttaaaggta 300

-continued

```
acttttatcg atgaccctag cgctgataaa cagattgccg ttattaatac aactggtagt    360

tttctaaaag caaatcctac tataagtgat gcacctattg ataactaccc aatccctggc    420

gctagtgcaa cattacgtta tccttcacaa tatgatgttg catttaacct tcaagataac    480

agcgctcgtt tctttaacgt agcgcctaca aatgctgtag aagaaacgac tgtaacatct    540

agcgtatctt atcaacttgg tggctctgtt aaagcttctg taacgcctaa tggccctagc    600

ggtgaagctg gtgcaactgg tcaagtcact tggtctgact ctgtaagcta taaacaaact    660

agttataaaa caaatttaat tgaccaaaca aacaaaaacg taaagtggaa cgtattcttt    720

aacggatata acaatcaaaa ctggggtatt tatacacgtg actcctatca ttctttatat    780

ggaaaccaac ttttcatgta ctctcgcaca tacctatatg aatctgatgc aaaaggtaat    840

ttaataccga tggatcaact tccagcgcta acaaatagtg gtttctctcc tggtatgatt    900

gctgttgtta tctctgaaaa aaatacagat caatctaact tacaggtcgc ttatacaaaa    960

cacgccgacg actaccaact tcgtccaggc tacacattcg gaactgcaaa ctgggttgga   1020

aacaacgtaa aagacgttga tcaaaaaaca tttaataaat tgttcacact agattggaag   1080

aataagaaat tagtagagaa aaaataa                                        1107


<210> SEQ ID NO 92
<211> LENGTH: 28
<212> TYPE: DNA
<213> ORGANISM: Artificial Sequence
<220> FEATURE:
<223> OTHER INFORMATION: Synthetic Primer

<400> SEQUENCE: 92

gataggatcc gtacagctag aggaagtc                                         28


<210> SEQ ID NO 93
<211> LENGTH: 38
<212> TYPE: DNA
<213> ORGANISM: Artificial Sequence
<220> FEATURE:
<223> OTHER INFORMATION: Synthetic Primer

<400> SEQUENCE: 93

cttcatttgc atggctttca tcaggtcata ctcttgtg                              38


<210> SEQ ID NO 94
<211> LENGTH: 39
<212> TYPE: DNA
<213> ORGANISM: Artificial Sequence
<220> FEATURE:
<223> OTHER INFORMATION: Synthetic Primer

<400> SEQUENCE: 94

aaagccatgc aaatgaagcg agaatgaaag agaccttgc                             39


<210> SEQ ID NO 95
<211> LENGTH: 30
<212> TYPE: DNA
<213> ORGANISM: Artificial Sequence
<220> FEATURE:
<223> OTHER INFORMATION: Synthetic Primer

<400> SEQUENCE: 95

caatggatcc ctgtaagcaa ctccaactac                                       30


<210> SEQ ID NO 96
<211> LENGTH: 29
```

-continued

<212> TYPE: DNA
<213> ORGANISM: Artificial Sequence
<220> FEATURE:
<223> OTHER INFORMATION: Synthetic Primer

<400> SEQUENCE: 96
ctgtggatcc cagggttatt ggttacagc 29

<210> SEQ ID NO 97
<211> LENGTH: 35
<212> TYPE: DNA
<213> ORGANISM: Artificial Sequence
<220> FEATURE:
<223> OTHER INFORMATION: Synthetic Primer

<400> SEQUENCE: 97
atactccgct gcttctctcg tttgactatc tgcag 35

<210> SEQ ID NO 98
<211> LENGTH: 37
<212> TYPE: DNA
<213> ORGANISM: Artificial Sequence
<220> FEATURE:
<223> OTHER INFORMATION: Synthetic Primer

<400> SEQUENCE: 98
agaagcagcg gagtatgatt cagcatcaaa gagatgc 37

<210> SEQ ID NO 99
<211> LENGTH: 28
<212> TYPE: DNA
<213> ORGANISM: Artificial Sequence
<220> FEATURE:
<223> OTHER INFORMATION: Synthetic Primer

<400> SEQUENCE: 99
caatggatcc ccagctatct ttcgctgt 28

<210> SEQ ID NO 100
<211> LENGTH: 30
<212> TYPE: DNA
<213> ORGANISM: Artificial Sequence
<220> FEATURE:
<223> OTHER INFORMATION: Synthetic Primer

<400> SEQUENCE: 100
cattggatcc gaaagagtgg tcatccgaac 30

<210> SEQ ID NO 101
<211> LENGTH: 37
<212> TYPE: DNA
<213> ORGANISM: Artificial Sequence
<220> FEATURE:
<223> OTHER INFORMATION: Synthetic Primer

<400> SEQUENCE: 101
tgaaactacg ctcaatttct ccatctactt ggttagc 37

<210> SEQ ID NO 102
<211> LENGTH: 38
<212> TYPE: DNA
<213> ORGANISM: Artificial Sequence
<220> FEATURE:
<223> OTHER INFORMATION: Synthetic Primer

<400> SEQUENCE: 102

-continued aaattgagcg tagtttcacc agtagctgct tttgcaag 38

<210> SEQ ID NO 103
<211> LENGTH: 29
<212> TYPE: DNA
<213> ORGANISM: Artificial Sequence
<220> FEATURE:
<223> OTHER INFORMATION: Synthetic Primer

<400> SEQUENCE: 103
cttaggatcc gatctgcttt ttgggatgc 29

<210> SEQ ID NO 104
<211> LENGTH: 37
<212> TYPE: DNA
<213> ORGANISM: Artificial Sequence
<220> FEATURE:
<223> OTHER INFORMATION: Synthetic Primer

<400> SEQUENCE: 104
ttcttttgat ccttttctct atcgtttcac gtgcttc 37

<210> SEQ ID NO 105
<211> LENGTH: 36
<212> TYPE: DNA
<213> ORGANISM: Artificial Sequence
<220> FEATURE:
<223> OTHER INFORMATION: Synthetic Primer

<400> SEQUENCE: 105
agaaaaggat caaaagaatg caagagagca tgctac 36

<210> SEQ ID NO 106
<211> LENGTH: 21
<212> TYPE: DNA
<213> ORGANISM: Artificial Sequence
<220> FEATURE:
<223> OTHER INFORMATION: Synthetic Primer

<400> SEQUENCE: 106
gctgctaaac aaagttggaa t 21

<210> SEQ ID NO 107
<211> LENGTH: 22
<212> TYPE: DNA
<213> ORGANISM: Artificial Sequence
<220> FEATURE:
<223> OTHER INFORMATION: Synthetic Primer

<400> SEQUENCE: 107
cgtaatacga ctcactatag gg 22

<210> SEQ ID NO 108
<211> LENGTH: 24
<212> TYPE: DNA
<213> ORGANISM: Artificial Sequence
<220> FEATURE:
<223> OTHER INFORMATION: Synthetic Primer

<400> SEQUENCE: 108
ctttctacag ggaaggattt agaa 24

<210> SEQ ID NO 109
<211> LENGTH: 21
<212> TYPE: DNA
<213> ORGANISM: Artificial Sequence
<220> FEATURE:
<223> OTHER INFORMATION: Synthetic Primer

<400> SEQUENCE: 109
cttaattcag agggaacagg a 21

<210> SEQ ID NO 110
<211> LENGTH: 1722
<212> TYPE: DNA
<213> ORGANISM: Bacillus thuringiensis

<400> SEQUENCE: 110
tcctatcaat actctcgcaa caccaatcgt tcaagcagaa actcaacaag aaaacatgga 60
tatttcttca tcattacgaa aattaggtgc gcattctaaa ttagtccaaa cgtatattga 120
tcaatcttta atgagtccta atgtacagct agaggaagtc ccagctttaa ataccaatca 180
attcctaatc aaacaagata tgaaggaatg gtcatcggaa ctctatccac agttaattct 240
attaaattca aaaagtaaag gatttgtaac aaaatttaat agttattacc cgacattaaa 300
atcgtttgta gacaataaag aagatagaga agggttttcg gatagacttg aagtacttca 360
agaaatggct atgacgaatc aagaaaatgc gcaacgacaa atcaatgaat taacagatct 420
taaattacag cttgataaaa aattaaaaga ttttgatact aatgtggcaa ctgcgcaagg 480
catactaagt acagatggaa caggaaaaat agatcagtta aaaaatgaaa tattaaatac 540
caaaaaagca attcaaaatg atttacagca aattgcatta ataccaggag ctttaaatga 600
gcagggattt gctatattca aagaagttta tagtctttca aaagaaatta ttgaaccggc 660
tgctcaagca ggggtggcag cgtataacaa aggaaaagaa attaacaact ctattctaga 720
agcggagaaa aaagcggcgc aagaagcgac agaacaaggt aaaactgctc tagagattga 780
atcagcaaaa aaagcagctc gtgaagcaat tgagaaaagc aaacaaggtg aaatagcagc 840
cgcagccgca gcaaaaacac aagagtatga cctgatgaaa gccatgcaaa tgaagcgaga 900
atgaaagaga ccttgcaaaa ggctggatta tttgcaaaat ctatgaatgc ctattcttat 960
atgttaatta agaatcctga tgtgaatttt gagggaatta ccattaatgg atatgtagat 1020
ttacctggta gaatcgtaca agatcaaaag aatgcaaggg cacatgccgt tacttgggat 1080
acgaaagtaa aaaaacagct tttagataca ttgaatggta ttgttgaata cgatacaaca 1140
tttgataatt attatgaaac aatgatagag gcgattaata caggggatgg agaaacttta 1200
aaagaaggga ttacagattt acgaggtgaa attcaacaaa atcaaaagta tgcacaacaa 1260
ctaatagaag aattaactaa attaagagac tctattggac acgatgttag agcatttgga 1320
agtaataaag agctcttgca gtcaatttta aaaaatcaag gtgcagatgt tgatgccgat 1380
caaaagcgtc tagaagaagt attaggatca gtaaactatt ataaacaatt agaatctgat 1440
gggtttaatg taatgaaggg tgctattttg ggtctaccaa taattggcgg tatcatagtg 1500
ggagtagcaa gggataattt aggtaagtta gagcctttat tagcagaatt acgtcagacc 1560
gtggattata aagtaacctt aaatcgtgta gttggagttg cttacagtaa tattaatgaa 1620
atgcacaagg cgcttgatga tgctattaac gctcttactt atatgtccac gcagtggcat 1680
gatttagatt ctcaatattc gggcgttcta gggcatattg ag 1722

<210> SEQ ID NO 111
<211> LENGTH: 1862
<212> TYPE: DNA
<213> ORGANISM: Bacillus thuringiensis -continued

<400> SEQUENCE: 111

```
actcatttct attaaacaag atatgaaaga gtggtcatcc gaactttatc ctaaattaat     60
tctattaaat tcaaaaagta aaggatttgt aactaaattt aatagttatt atccaacatt    120
aaaaggattt gtagataata aggaagataa agaagggttt acagatagac tggaagtcct    180
tcaagacatg accatcacaa accaagaaag tgtgcaacgt caaattaatg agttaacaga    240
tctaaaacta caggtagata agaagttgaa aaatcttgat actgatgtgg caaaaacaca    300
gagtgtcctt aattcagagg gaacaggaaa aatagataag ttaaaaaatg aaatgctaga    360
tacaaaaaaa tcaattcaaa atgatttaca gcaaatagcg ttattaccag gagctttaaa    420
tgaacaagga ctaaaggtat tccaagaaat ttatagtcta tcaaaagata tcattgaacc    480
ggctgctcaa acagcagtag tagcgtataa caaaggaaaa gaaataaaca atgctattgt    540
agacgcagag aataaagcag agcaagaagc aaaagaaaaa ggaaaatcag ctatagaaat    600
tgaggctgcc aaaaaagaag cacgtgaagc gatagagaaa agtaaaaaag gtgaaatcgc    660
tgcagctgca gttacaaaaa cgaaagagta tgatcttatg aaagtaattg atcctgaaaa    720
aattaaaaaa acatataata cttttgctga aattaataaa ctaacagcag agcaacgtgc    780
atatttaaat gatttagaga aacaaaatca gaaattatat gacttaacga ctaaattaac    840
agtagcagat ttacaaaaat caatgattct tttcatgcaa aatgatttgc atacatttgc    900
taaccaagta gatggagaaa ttgagcgtag tttcaccagt agctgctttt gcaagtgaaa    960
gtaaaataga acaaaccagt acggaagata tatctctttc tgtaaacagt gaaaagatga   1020
aaaaagcttt gcaagatgct ggggtatttg caaaatccat gaatgattac tcttatttgt   1080
taattaataa tccagatgtt aactttgaag gaattgatat taaaggatat acaaatctac   1140
ctagtcaaat tgcacaagat caaaagaatg caagagagca tgctacaaaa tgggatgctc   1200
acataaaaaa acaactttta gataccctta caggaattgt agagtatgat accacatttg   1260
acaattatta cgatacatta gtagaagcaa ttaatgaagg agatgcagat acattaaaag   1320
aaggcattac agatttacaa ggtgagatta aacaaaacca agcatataca cagaatttaa   1380
ttcaagaact agctaagtta agagatagta ttggagaaga tgtccgagca tttggaggtc   1440
ataaagatat cttgcaatcg attttaaaaa atcaagcatc tggaatagat gaagatgaaa   1500
aacgcctaaa tgatgtttta gagcaaataa gacattttaa acaagtagaa tcggatggaa   1560
taataactgt atcatatcct tcaatcccta catggattgc tggaggtgtg atgatagggg   1620
tagcaagaaa taatttaggt acgttagagc cgttattagt gcaattacgc caaaccgtag   1680
actataaaat aacattaaat cgtgtagttg gagttgcgta taataatatt actgaaatgc   1740
aaaatgcaat tggatcagct attaatgctc ttacctatat gtcagcacaa tggcatgatt   1800
tagattctca atattcagga gtgcttaatc atattgataa agcatcccaa aaagcagatc   1860
aa                                                                  1862
```

<210> SEQ ID NO 112
<211> LENGTH: 1348
<212> TYPE: DNA
<213> ORGANISM: Bacillus thuringiensis

<400> SEQUENCE: 112

```
tctaattaaa caagatatga aagagtggtc atccgaactt taccctaaat taattctatt     60
aaattcaaaa agtaaaggat ttataactaa atttaatagt tattatccaa cattaaaagg    120
atttgtagat aataaggaag ataaagaagg gtttacagat agactggaag ttcttcaaga    180
```

```
catgactata acaaatcaag aaagtgtgca acgtcaaatt aatgagttaa cagatttaaa    240
attactggta gataagaagt tgaaaaacct tgatactgat gtggtaaaag cacaaagtgt    300
ccttaattca gagggaacag gaaaaataga taagttaaaa aatgaaatgc tagatacaaa    360
aaaatctatt caaaatgatt tgcagcaaat agcattatta ccaggcgcgt taaatgaaca    420
agggctaaag gtattccaag aaatttatag tctatcgaaa gatatcattg aaccggctgc    480
tcaaacagca gtagtagcgt ataacaaagg aaaagaaata aacaatgcca ttgtagacgc    540
agagaagaaa gcagagcaag aagcaaaaga aaagggaaaa tcagctatag aaattgaagc    600
tgccaaaaaa gaagcacgtg aaacgataga gaaaaggatc aaaagaatgc aagagagcat    660
gctacaaagt gggatgcgca cataaaaaaa caacttttag atactcttac aggaattgta    720
gagtatgata ctacatttga caattattac gatacattag tagaagcaat taatgaagga    780
gatgcagata cattaaaaga aggcattaca gatttacaag gtgagattaa aaaaaaccaa    840
gcatatacaa agaatttaat acaagaacta gctaagttaa gagatagtat tggagaagat    900
gtccgagcat ttggaggtca taaagatatc ttgcaatcga ttttaaaaaa tcaagcatct    960
ggaatagatg aagatgaaaa acgtctaaat gatgttttag agcaagtaag acattttaaa   1020
caagtagaat cggatggaat aataactgta tcagttccct caatccctac atggattgct   1080
ggaggtgtaa tgataggggt agcaagaaat aatttaagta cgctggaacc gctattagcg   1140
caattgcgcc aaacggtaga ctataaaatt acattgaatc gtgtagttgg agttgcgtat   1200
aataatattg ctgaaatgca aaatgcaatt ggatcagcta ttaatgctct cacctatatg   1260
tcagcacaat ggcatgattt agattctcaa tattcaggag tacttaatca tattgataaa   1320
gcatcccaaa aagcagatca aaataatt                                       1348
```

```
<210> SEQ ID NO 113
<211> LENGTH: 1378
<212> TYPE: DNA
<213> ORGANISM: Bacillus thuringiensis

<400> SEQUENCE: 113

atattatttt gcacagccag acattaaggt aaatgcgatg agtagcttag cgaatcatca     60
aaagtttgca aaggcgaatg tacgagagtg gattgatgaa tataatccga agctaattga    120
cttaaatcaa gagatgatga gatacagcac tagattcaat agttattata gtaagctcta    180
tgaactagca ggaaatgtaa atgaagatca gcaagcaaaa acagatttta tgagtgcata    240
tggaaaatta caattgcaag tacagagcat ccaagagagt atggagcaag atttattaga    300
gttaaatcga tttaaaacag tattagacaa agatagtaac aacttatcaa ttaaagccga    360
tgaagcaata aaaacactgc aaggatcaag tggagatatt gtgaaattaa gagaagatat    420
taaaagaatt caaggggaaa ttcaagctga actaactact attttgaata gacctcaaga    480
aataattaaa ggttctatta atatcggtaa acaagtattt acaatcacaa atcaaactgc    540
acaaacgaaa acaatcgatt ttgtttctat cggtacttta agtaatgaaa ttgtaaatgc    600
tgcagatagt caaacgagag aagcagcgga gtatgattca gcatcaaaga gatgcaaaaa    660
ttaatgcagc atattggtta aataatatga agcctcaaat tatgaaaaca gatcaaaata    720
ttataaatta caataatact tttcaatcgt attataatga catgttaata gcgattgatc    780
aaaaggatag tggaaaatta aaagcggatt tagaaaagtt gtatgcggat attgtaaaga    840
atcaaaatga ggtagatgga ttattaggaa atttgaaagc ttttcgcgat agaatggcga    900
```

-continued

```
aagatacaaa tagtttcaaa gaggatacaa atcagttaac agcgatattg gcaagtacga    960

atgctggtat tccagctcta gagcaacaaa taaatacata taacgattcg attaaaaaga   1020

gtaatgatat ggtcattgct ggtggcgtac tttgcgtagc tctaataaca tgtcttgctg   1080

gcgggccgat gattgcggtt gcgaaaaaag atatcgcaaa tgcagaaaga gaaatcgcca   1140

atttaaaaga tagaatttca ggagcacaag cagaagtcgt aattttgact gatgtaaaaa   1200

ataaaacaac aaacatgaca gaaacaattg atgcagcaat tacagcacta caaaacatat   1260

caaatcaatg gtatacagta ggtgcaaagt ataataattt attacaaaac gtaaaaggaa   1320

ttagtccgga agagtttacg tttataaaag aagatttaca tacagcgaaa gatagctg     1378
```

<210> SEQ ID NO 114
<211> LENGTH: 1017
<212> TYPE: DNA
<213> ORGANISM: Bacillus thuringiensis

<400> SEQUENCE: 114

```
gaagtaaata gaacaaacca gtacggaaga tatatctctt tctgtaaaca gtgaaaagat     60

gaaaaaagct ttgcaagatg ctggggtatt tgcaaaatcc atgaatgatt actcttattt    120

gttaattaat aatccagatg ttaactttga aggaattgat attaaaggat atacaaatct    180

acctagtcaa attgcacaag atcaaaagaa tgcaagagag catgctacaa agtgggatgc    240

gcacataaaa aaacaacttt tagatactct tacaggaatt gtagagtatg atactacatt    300

tgacaattat tacgatacat tagtagaagc aattaatgaa ggagatgcag atacattaaa    360

agaaggcatt acagatttac aaggtgagat taaaaaaaac caagcatata caaagaattt    420

aatacaagaa ctagctaagt taagagatag tattggagaa gatgtccgag catttggagg    480

tcataaagat atcttgcaat cgattttaaa aaatcaagca tctggaatag atgaagatga    540

aaaacgtcta aatgatgttt tagagcaagt aagacatttt aaacaagtag aatcggatgg    600

aataataact gtatcagttc cctcaatccc tacatggatt gctggaggtg taatgatagg    660

ggtagcaaga aataatttaa gtacgctgga accgctatta gcgcaattgc gccaaacggt    720

agactataaa attacattga atcgtgtagt tggagttgcg tataataata ttgctgaaat    780

gcaaaatgca attggatcag ctattaatgc tctcacctat atgtcagcac aatggcatga    840

tttagattct caatattcag gagtacttaa tcatattgat aaagcatccc aaaaagcaga    900

tcaaaataaa tttaaattct taaaacctaa tctgaatgca gccaaagaca gctggaaaac    960

attaagagca gatgcgttta cattaaaaga aggaataaaa acattaaaaa tggatcc     1017
```

<210> SEQ ID NO 115
<211> LENGTH: 1003
<212> TYPE: DNA
<213> ORGANISM: Bacillus thuringiensis

<400> SEQUENCE: 115

```
cagacgacgc tcagaacaga aaatagaaaa ttatgcgtta ggacctgaag gattaaagaa     60

agcgttggct gaaacaggct ctcatattct tgtaatggat ttgtacgcaa aaactatgat    120

taagcaaccg aatgtaaatt tatccaacat tgatttaggt tcgggtggag aagaattaat    180

caaaaatatt cacctgaatc aagaactgtc acgaatcaat gcaaattact ggttagatac    240

agcgaagcca aacattcaaa aaacagcacg taatattgta aattatgatg agcaatttca    300

aaattattac gacacattag tagatactgt aaaaaagaag gataaggtga gcctcaaaga    360

aggaataggg gatttaatct atacaattca tacaaattca aatgaagtta cggaagtcat    420
```

taagatgtta gaggctttca aaacaaagtt gtatacaaat actgtagatt ttaaaaataa 480
tgttggtggt ccagatggac agggaggatt gacggctata ttagcgggaa aacaagcgct 540
agtcccacaa cttcaggccg aaattgagaa tttacgttct acacagaaaa cacattttga 600
taatgtatta gcctggtcaa ttggtggtgg attaggagca gctattttag ttattggaac 660
gattgcagga gcggtagtaa ttgttgtgac tggtggtaca gctacgccag ctgttgttgg 720
tggtcttaca gctctaggag ccgctggtat cggtttagga acagcagctg gcgtcgaggc 780
atctaatcat atgaattctt ataatgaaat ttcgaataaa atcggagaat taagtatgaa 840
agctgatttg gctaatcaag cggttatttc acttactaat acgaaagaca ctctaacata 900
tttgtatcag acagtggatc aagcaataat gtctctaaca agtattcagc aacaatggaa 960
taaaatgggg gctaattata aagatttata tgataatatc gat 1003

<210> SEQ ID NO 116
<211> LENGTH: 1058
<212> TYPE: DNA
<213> ORGANISM: Bacillus thuringiensis

<400> SEQUENCE: 116
gcaaacgtat gcaaatcatt tgtgtaagaa gaagcatgat tttgtaaat cagctattga 60 tagtttcgtt gttaaatcat atattttttg attttgtttc tctaaatcat ctaaatatgc 120
tcgctgttct gctgttaatt tatttacttc agcaaaaacg ccaaatgttt tcttaatctt 180
ttcggtatca atgaccttca tcaggtcata ctcttgtgtt tttgctgcgg ctgcggctgc 240
tatttcacct tgtttgcttt tctcaattgc ttcacgagct gcttttttttg ctgattcaat 300 ctctagagca gttttacctt gttctgtcgc ttcttgcgcc gcttttttct ccgcttctag 360
aatagagttg ttaatttctt ttcctttgtt atacgctgcc acccctgctt gagcagctgg 420
ttcaataatt tcttttgaaa gactataaac ttctttgaat atagcaaatc cctgctcatt 480
taaagctcct ggtattaatg caatttgctg taaatcattt tgaattgctt ttttggtatt 540
taatatttca ttttttaact gatctatttt tcctgttcca tctgtactta gtatgccttg 600
cgcagttgcc acattagtat caaaatcttt taattttttta tcaagctgta atttaagatc 660
tgttaattca ttgatttgtc gttgcgcatt ttcttgattc gtcatagcca tttcttgaag 720
tacttcaagt ctatccgaaa acccttctct atcttcttta ttgtctacaa acgattttaa 780
tgtcgggtaa taactattaa attttgttac aaatccttta ctttttgaat ttaatagaat 840
taactgtgga tagagttccg atgaccattc cttcatatct tgtttgatta ggaattgatt 900
ggtatttaaa gctgggactt cctctagctg tacattagga ctcattaaag attgatcaat 960
atacgtttgg attaatttag attgcgcacc taattttcgt aatgaagagg aaatatccat 1020
gcctttctgt tgagtttccg cttgaacgat tggtgttg 1058

<210> SEQ ID NO 117
<211> LENGTH: 1014
<212> TYPE: DNA
<213> ORGANISM: Bacillus thuringiensis

<400> SEQUENCE: 117
gcttttaaac aggagtagaa ctgaaattta aaacctaaat tggaggaaaa tgaaatgata 60
aaaaaaatcc cttataaatt actcgctgta tcgacgctat taactattac aactgctaat 120
gtagttttac cagtaacaac ttttgcaagt gaaattgaac aaacgaacaa tggagatacg 180

```
gctctttctg caaatgaagc gagaatgaaa gagaccttgc aaaaggctgg attatttgca    240

aaatctatga atgcctattc ttatatgtta attaagaatc ctgatgtgaa ttttgaggga    300

attaccatta atggatatgt agatttacct ggtagaatcg tacaagatca aaagaatgca    360

agggcacatg ctgttacttg ggatacgaaa gtaaaaaaac agcttttaga tacattgaat    420

ggtattgttg aatacgatac aacatttgac aattattatg aaacaatggt agaagcgatt    480

aatacagggg atggagaaac tttaaaagaa gggattacag atttgcgagg tgaaattcaa    540

caaaatcaaa agtatgcaca acaactaata gaagaattaa ctaaattaag agactctatt    600

ggacatgatg ttagagcttt tggaagtaat aaagagctct tgcagtcaat tttaaaaaat    660

caaggtgcag atgttgatgc cgatcaaaag cgtctagaag aagtattagg atcagtaaac    720

tattataaac aattagaatc tgatgggttt aatgtaatga agggtgctat tttgggtcta    780

ccaataattg gcggtattat agtgggagta gcaagggata atttaggtaa gttagagcct    840

ttattagcag aattacgtca gactgtggat tataaagtaa ccttaaatcg tgtagttgga    900

gttgcttaca gtaatattaa tgaaatgcac aaggcgcttg atgatgctat taacgctctt    960

acttatatgt ccacgcagtg gcatgattta gattctcaat attcgggcgt tcta         1014


<210> SEQ ID NO 118
<211> LENGTH: 605
<212> TYPE: DNA
<213> ORGANISM: Bacillus thuringiensis

<400> SEQUENCE: 118

agtaccgata gaaacaaaat cgattgtttt cgtttgtgca gtttgatttg tgattgtaaa     60

tacttgttta ccaatattaa tagaaccttt aatgatttct tgaggtctat tcaaaatagt    120

agttaattca gcttgaattt caccttgaat tcttttaata tcttctctta atttcacaat    180

atctccactt gatccttgca gtgtttttat tgcttcatcg gctttaattg ataagttgtt    240

actatctttg tctaatactg ttttaaatcg atttaactct aataaatctt gctccatact    300

ctcttggatg ctttgtactt gcaattgtaa ttttccatat gcactcataa aatctgcttt    360

tgcttgctga tcttcattta cgtttcctgc taattcatag agcttactat aatagctatt    420

aaatctagtg ctgtatctca tcatctcttg atttaagtca attagcttcg gattatattc    480

atcaatccat tctcgtacat tcgcctttgc aaactttga  tgattcgtta agctactcat    540

cgcatttacc ttaatatctg gctgttgtaa aataattaat ccatatgctt gaataagcgg    600

tgatt                                                                605


<210> SEQ ID NO 119
<211> LENGTH: 951
<212> TYPE: DNA
<213> ORGANISM: Bacillus thuringiensis
<220> FEATURE:
<221> NAME/KEY: misc_feature
<222> LOCATION: (869)..(869)
<223> OTHER INFORMATION: n is a, c, g, or t

<400> SEQUENCE: 119

cttccggact aattcctttt acgttttgta gtaaattatt atattttgca cctactgtat     60

accattggtt tgatatgttt tgtagtgctg taattgctgc atcaattgtt tccgtcatgt    120

ttgttgtttt attttttaca tcagtcaaaa ttacgatttc tgcttgtgct cctgaaattc    180

tatcttttaa attagctatc tctctttctg catttgcgat atcttttttt gcaaccgcaa    240

tcatcggccc gccagcaaga catgttatta gcgctacgca aagtacgcca ccagcaatga    300
```

-continued

```
ccatatcatt actcttttta atcgaatcgt tatatgtatt tatttgttgc tctagagctg    360

gaataccagc attcgtactt gccaatatcg ctgttaactg atttgtatcc tctttgaaac    420

tatttgtatc tttcgccatt ctatcgcgaa aacttttcaa atttcctaat aatccatcta    480

cctcattttg attctttaca atatccgcat acaacttttc taaatccgct tttaattttc    540

cgctatcctt ttgatcaatc gctattaaca tgtcgttata atacgattga aaagtattat    600

tgtaatttat aatattttga tccgttttca taatttgagg cttcatatta tttaaccaat    660

atgctgcatt aatttttgca tctctttgat gctgaatcat attcccttta aattcactat    720

taatcgaact tattttactt aaatccgtct cttgttgatt ttgaattaat tttgcatatg    780

aatccattgc aaatatactc gatgtcgttt gtgccattac atcttggaat ccagctggtc    840

caagagaata gtttttcaca ttttcttgna gtacctttac attttgttct gctgcaaaag    900

gatgtaagga gatacgttac tcgttgccac ccagcaatca ttaccgctaa a             951
```

CONSTRUCTION OF A QUADRUPLE ENTEROTOXIN-DEFICIENT MUTANT OF *BACILLUS THURINGIENSIS*

CROSS-REFERENCE TO RELATED APPLICATIONS

This application claims the benefit of U.S. Provisional Patent Application No. 61/353,314, filed Jun. 10, 2010, incorporated herein by reference as if set forth in its entirety.

STATEMENT REGARDING FEDERALLY SPONSORED RESEARCH OR DEVELOPMENT

This invention was made with United States government support under 05-CRHF-0-6055 awarded by USDA/CSREES. The government has certain rights in the invention.

BACKGROUND OF INVENTION

"Biological control" or "biocontrol" is defined as pathogen suppression by the use of a second organism. Mechanisms of biological control are diverse. Biocontrol has long been thought to be safer for the environment and human health than synthetic pesticides (Cook et al. 1996; Benbrook et al., 1996). As bacterial biocontrol agents have reached the federal regulatory agencies for review, the agencies and the public have voiced concerns over the relatedness of some agents to human pathogens.

*Bacillus* species are widely used in agriculture as biocontrol agents of pathogens (e.g., oomycetes such as *Pythium* sp. and *Phytopthera* sp.) and insects (Handelsman et al. 1990; Silo-Suh et al. 1998; Shang et al. 1999). *Bacillus thuringiensis* is a biocontrol agent that produces insecticidal crystal toxin proteins, encoded by cry genes, that specifically kill insects including Lepidopterans, Dipterans, Coleopterans, Hymenopterans, and also kill nematodes. Methods for stabilizing and applying such toxins, or strains harboring the toxins, are known for a wide variety of field crop situations. Although distinct *B. thuringiensis* strains vary in target range and efficacy, the toxins required for biological control, and methods for preparing inocula for use in the field, are generally similar among strains.

Because *B. thuringiensis* is closely related genetically to food contaminant bacterium *Bacillus cereus*, concerns have been raised in the U.S. and Europe about its widespread use on food crops. Phylogenetic chromosomal marker studies show no taxonomic basis for separate species status for the two. While *B. thuringiensis* carries plasmids bearing the cry genes that encode insecticidal crystal toxins, *B. cereus* does not. On the other hand, *B. cereus* expresses chromosomally-encoded enterotoxin genes, the products of which are responsible for food-borne disease in humans, haemolysin BL (HBL), non-haemolytic enterotoxin (NHE) and cytotoxin K (CytK) (Beecher & MacMillan, 1991; Lund & Granum, 1996; Lund et al., 2000). Depending upon the strain, different toxins can be responsible for disease.

HBL and NHE are both three-component toxin complexes, which are restricted to the *B. cereus* group (From et al., 2005). HBL includes three component proteins, L2, L1 and B (Beecher & MacMillan, 1991), encoded by the genes hblC, hblD, and hblA, respectively, that are co-transcribed from the hblCDA operon (Heinrichs et al., 1993; Ryan et al., 1997; Lindbäck et al., 1999). NHE includes the proteins NheA, NheB and NheC, encoded by the nheABC operon (Granum et al., 1999).

Single component CytK belongs to the family of β-barrel pore-forming toxins (Fagerlund et al., 2008). Two cytK gene variants, cytK-1 and cytK-2, are known (Lund et al., 2000; Fagerlund et al., 2004). The original CytK-1 protein was isolated from a strain of *B. cereus* that caused three fatalities in a food poisoning outbreak (Lund et al., 2000). The CytK-2 version of the protein was subsequently identified from other strains of *B. cereus* (Fagerlund et al., 2004). This form is 89% identical to CytK-1 at the amino acid level and exhibits about 20% toxicity relative to CytK-1 toward human intestinal cells (Fagerlund et al., 2004).

A homolog of HBL has been discovered in the *B. cereus* group. Beecher and Wong (2000) showed that $HBL_a$, isolated from a strain of *B. cereus* that also produced HBL, had similar toxicity as HBL and the homologous proteins could be interchanged. The 36 to 45 amino acids of the N-terminal sequence of the individual $HBL_a$ component proteins were reported in the Beecher and Wong study, but the gene sequences for $HBL_a$ were not known. However, an $HBL_a$ operon has been identified in the *B. cereus* UW85 partial genome sequence (D. Rasko, J. Ravel, J. Handelsman, unpublished). *B. weihenstephanensis* strain KBAB4 (Genbank accession CP000903) and *B. cereus* strain 03BB108 (Genbank accession ABDM00000000) also contain $HBL_a$ sequences. The sequences disclosed in all cited Genbank accession numbers are incorporated herein by reference in their entirety as if set forth herein. The N-terminal sequences of the predicted $HBL_a$ proteins from UW85 are 100%, 69%, and 94% identical to the respective $B_a$, $L_{1a}$, and $L_{2a}$ N-terminal sequences reported by Beecher and Wong (2000).

Some efforts to reduce or eliminate enterotoxin activity disrupted the components of the enterotoxin. U.S. Pat. No. 6,602,712 (Handelsman and Klimowicz; incorporated herein by reference as if set forth in its entirety) describes a *Bacillus* strain that exhibits reduced HBL enterotoxin activity. An alteration in the hblA gene of the hbl locus renders inactive the B component of the HBL protein. The other HBL components and other enterotoxin gene sequences were not disrupted. A corresponding component in the $HBL_a$ homolog may compensate for the lack of B component encoded by hblA.

When components NheB and NheC were eliminated from a *B. cereus* strain that lacked HBL and CytK, the strain lost haemolytic activity against erythrocytes from a variety of species (Fagerlund et al., 2008).

Prior attempts to eliminate the complete nhe operon in *B. cereus* and *B. thuringiensis* have failed (Ramarao & Lereclus, 2006; Fagerlund et al., 2008).

Many commercial *B. thuringiensis* strains, including subsp. *kurstaki* strain VBTS 2477, express such enterotoxin genes (Arnesen et al., 2008). The safety and public acceptance of *B. thuringiensis* on food crops would be enhanced by an enterotoxin-deficient *B. thuringiensis* strain that retains insecticidal activity but which does not produce an enterotoxin or its corresponding components. No *B. thuringiensis* strain is available that has reduced or zero levels of the enterotoxins or the functional components of the enterotoxins, including those components for NHE and HBL. Without the complete removal of these enterotoxins, the risk of toxicity remains.

BRIEF SUMMARY OF THE INVENTION

The present invention relates to enterotoxin-deficient bacterial strains in the *B. cereus* group, which contains *B. cereus, B. thuringiensis, B. anthracis, B. mycoides, B. pseudomycoides*, and *B. weihenstephanensis*. The strains advantageously lack the components that encode the enterotoxin products associated with human toxicity. In some strains, the operons of four enterotoxins identified in a *B. thuringiensis* strain were altered to make the components, including the NHE enterotoxin, non-functional and thus the enterotoxins themselves non-functional. All of the components for NHE are altered in the inventive strains; no functional component for the enterotoxin products associated with human toxicity remains. Also, a new HBL homolog is described and made non-functional in the *B. thuringiensis* strains VBTS 2477 and VBTS 2478.

In a first aspect, the invention is summarized as a method for obtaining a mutant *Bacillus*, the method including the steps of mutating a *Bacillus* to produce a mutant *Bacillus* that does not form active HBL, NHE, $HBL_{a1}$, and $HBL_{a2}$ enterotoxins, and selecting the mutant *Bacillus*. In some embodiments of the first aspect, the mutating step introduces a mutation in an operon that encodes all components of the NHE enterotoxin and all components of at least one of the HBL, $HBL_{a1}$, and $HBL_{a2}$ enterotoxins. In other embodiments of the first aspect the mutating step deletes a portion of the operon. Mutation in the operon can yield a polynucleotide that encodes a portion of a first enterotoxin component spliced to a portion of a last enterotoxin component. Certain starting strains may already lack one or more of the genes that would encode an enterotoxin. As such, an enterotoxin deficient strain can be produced by altering the enterotoxin-encoding genes that are present.

In some embodiments of the first aspect, the *Bacillus* to be mutated is *Bacillus thuringiensis* subspecies *kurstaki* strain VBTS 2477.

In some embodiments of the first aspect, the *Bacillus* to be mutated and the mutant *Bacillus* comprise at least one gene that encodes a protein having insecticidal properties.

In a second aspect, the invention relates to an isolated *Bacillus thuringiensis* strain that does not produce does not produce NHE enterotoxin and does not produce at least one of HBL, $HBL_{a1}$, and $HBL_{a2}$ enterotoxins. In one embodiment of the second aspect, the *B. thuringiensis* strain is insecticidal. In other embodiments of the second aspect, the *B. thuringiensis* strain produces δ-endotoxin. In other embodiments of the second aspect, the *B. thuringiensis* strain is subspecies *kurstaki* strain VBTS 2477.

In a preferred embodiment of the second aspect, the insecticidal *B. thuringiensis* strain carries disabling mutations in the nhe, hbl, $hbl_{a1}$, and $hbl_{a2}$ operons. In this strain, at least one of the mutated hbl, $hbl_{a1}$, $hbl_{a2}$, nhe operons can have the sequence of at least one of SEQ ID NO: 110, SEQ ID NO: 111, SEQ ID NO: 112, and SEQ ID NO: 113 respectively.

In a third aspect, the invention relates to a method for obtaining a mutant *B. thuringiensis* subspecies *kurstaki* strain VBTS 2477 by mutating strain VBTS 2477 to prevent formation of active HBL, NHE, $HBL_{a1}$, and $HBL_{a2}$ enterotoxins, and selecting a mutant of strain VBTS 2477 including at least one mutation. In one embodiment of the third aspect, the mutating step includes making deletions in hbl, nhe, $hbl_{a1}$, and $hbl_{a2}$ relative to strain VBTS 2477.

In a fourth aspect, the invention relates to an insect control method including the step of applying to at least one surface of a plant a formulation comprising a mutant *Bacillus* that does not form active HBL, NHE, $HBL_{a1}$, and $HBL_{a2}$ enterotoxins. In one embodiment of the fourth aspect, application of the formulation is achieved by spraying, dusting, or drenching the plant with the formulation.

In some embodiments of the fourth aspect, the plant is susceptible to infestation by Lepidopterans, Dipterans, Coleopterans, Hymenopterans. In other embodiments of the fourth aspect, the plant is susceptible to infestation by nematodes.

Quadruple and double enterotoxin-deficient *B. thuringiensis* strains, such as those exemplified herein, that do not include any added DNA are not considered genetically engineered under the EPA definition of genetic engineering (Federal Register 1997, 17910-17958) and are not subject to any regulations that do not otherwise apply to a wild type strain.

These and other features, aspects and advantages of the present invention will be more fully understood from the description that follows. The description of preferred embodiments is not intended to limit the invention but rather to cover all modifications, equivalents and alternatives. Reference should therefore be made to the claims herein for interpreting the scope of the invention.

DESCRIPTION OF PREFERRED EMBODIMENTS

The present invention is exemplified by a quadruple enterotoxin-deficient *B. thuringiensis* mutant strain lacking enterotoxin protein components implicated in human food poisoning. In a preferred embodiment of the present invention, the quadruple enterotoxin-deficient *B. thuringiensis* mutant strain has endogenous insecticidal properties. In four operons that each encode three protein components in wild-type *B. thuringiensis*, the mutant strain lacks functional coding sequences for each component. Based on insect bioassays, the LC50 of the quadruple enterotoxin-deficient strain was the same as the wild-type strain (See Table 8, infra).

Figure 1:
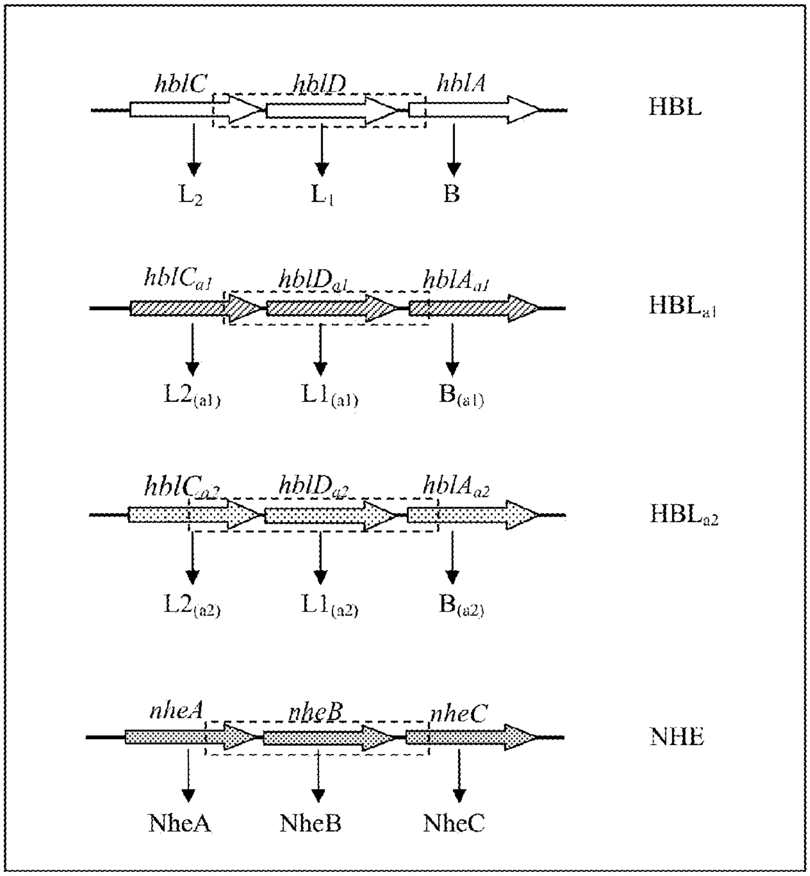
FIG. 1 depicts the HBL and NHE operons in *B. thuringiensis* VBTS 2477. The dotted rectangles indicate the deletion that was introduced in each operon. Vertical arrows point to the protein product of the gene.

In a first aspect, the applicants exemplify a defined *B. thuringiensis* strain that differs from wild-type strain VBTS 2477 at four operons (HBL, NHE, $HBL_{a1}$, and $HBL_{a2}$) and is deficient for cytotoxic enterotoxins. The quadruple enterotoxin-deficient mutant of the present invention does not produce an active HBL, NHE, $HBL_{a1}$ and $HBL_{a2}$ enterotoxin, nor does it produce any component of the respective wild-type enterotoxin. Whereas the wild-type polynucleotides of each operon encode three genes, the enterotoxin-deficient mutant differs from the wild-type strain in that it lacks sequences that span the three-gene portion. (FIG. 1). A DNA sequence that encodes a portion of the first enterotoxin component is adjacent to a DNA sequence that encodes a portion of the last enterotoxin component of each operon, creating a version of each operon where DNA sequences from the end of the first gene, the entire middle gene, and the beginning of the final gene in the operon are removed. The skilled artisan will appreciate that the invention can readily be achieved in a strain having a different deletion or using another type of mutation (insertion, missense) in the coding sequence of each operon component. In addition to any change that inactivates a component, the polynucleotide encoding the component can also include additional changes that may not otherwise alter the function of the component. Such mutants would fall within the scope of the invention as long as they are unable to produce all three components of the subject enterotoxin by virtue of a change in all three polynucleotides that encode the three components of the enterotoxin. Isolated preparations of naturally occurring mutants can also fall within the scope of the present invention.

The enterotoxin-deficient mutant of the present invention is exemplified using *B. thuringiensis*, and particularly in terms of changes relative to *B. thuringiensis* strain VBTS 2477, but can be mutants of any member of the *B. cereus* group of bacteria. Preferably, the mutant is also characterized by having a biological control activity when used as an active agent in an inoculum, as described infra.

In a second aspect, the invention is a method for producing an enterotoxin-deficient mutant of the present invention, wherein the method includes the step of modifying in a *Bacillus* strain the operon that encodes the NHE enterotoxin and at least one of the HBL, $HBL_{a1}$ and $HBL_{a2}$ enterotoxins. In a preferred embodiment, method includes the step of modifying in a *Bacillus* strain the operon that encodes the NHE, HBL, $HBL_{a1}$ and $HBL_{a2}$ enterotoxins. Modification can be achieved by altering the polynucleotides that encode NHE and at least one of the HBL, $HBL_{a1}$, and $HBL_{a2}$ components, for example, by gene replacement. A suitable method for gene replacement, described in the accompanying Examples, employs a vector, or vectors, carrying a desired mutation that alters the operon such that it no longer encodes a functional enterotoxin. Comparable replacement of genes in the other operons that encode HBL, $HBL_{a1}$, and $HBL_{a2}$ enterotoxins ensures absence of these other enterotoxins from the strain. The order of the gene replacement is not vital. The vector, or vectors, can be cured from cells at a non-permissive temperature, and further permits screening of mutants on the basis of resistance or sensitivity to an antibiotic.

The invention has particular utility when applied in strains of *B. thuringiensis* that produce biocontrol insecticidal δ-endotoxins. Such strains include, but are not limited to, *B. thuringiensis* subsp. *kurstaki* strain VBTS 2477 (ATCC Reference Number SD-5811; having cry toxin genes Cry1Aa, 1Ab, 1Ac, 1Ia, 2Aa, 2Ab, Vip3Aa1). One or more mutations that inactivate at least the hbl, nhe, $hbl_{a1}$ and $hbl_{a2}$ operons of the respective enterotoxin can be introduced into a *B. thuringiensis* strain, thereby eliminating the enterotoxin from the strain. Since *B. thuringiensis* is closely related genetically to *B. cereus*, it is further specifically envisioned that other enterotoxin-deficient *Bacillus* strains can be produced in accord with this disclosure, and that some enterotoxin deficient *Bacillus* strains will also have insecticidal activity.

In a further aspect, the invention is a method for biological control of insect pests, where the method comprises applying an inoculum that includes as an active agent a novel quadruple enterotoxin-deficient mutant of a strain in the *Bacillus* group. The active agent is preferably an enterotoxin-deficient *B. thuringiensis* strain. The mutants of the present invention can be used in a method for biological control in the same ways as *B. thuringiensis* subsp. *kurstaki* strain VBTS 2477 and other such insecticidal strains are used, such methods for preparing and inoculating the biological control agent on a target or targets being known to the skilled artisan. A suitable assay for monitoring the biocontrol activity of an enterotoxin-deficient strain of the present invention is an insect bioassay such as that described herein (Example 1).

The invention will be more fully understood upon consideration of the following non-limiting Examples.

EXAMPLES

Example 1

Materials and Methods

Bacterial strains, plasmids, and growth conditions. The strains and plasmids used in the present study are listed in Table 1. *Escherichia coli* was grown in Luria-Bertani (LB) medium at 37° C. *B. thuringiensis* was grown in either LB or 0.5× Tryptic Soy Broth (TSB) or on 0.5× Tryptic Soy Agar (TSA) at 28° C., 37° C., or 40.5° C. For conjugation, *B. thuringiensis* was grown in Brain Heart Infusion (BHI) medium. Antibiotics were used at the following concentrations: for *E. coli*, ampicillin (Amp) at 200 μg/ml, chloramphenicol (Cm) at 10 μg/ml; for *B. thuringiensis*, erythromycin (Ery) at 3 μg/ml for selection of pMAD or 5 μg/ml for selection of pBKJ236, polymyxin B at 60 μg/ml for conjugations with pBKJ236, and tetracycline (Tet) at 10 μg/ml for selection of pBKJ223.

TABLE 1

Bacterial strains and plasmids used in this study.

| Strain or plasmid | Description | Source or Reference |
|---|---|---|
| Strains | | |
| *Bacillus thuringiensis kurstaki* strain VBTS 2477 | Wild-type | Valent Biosciences Inc. (ATCC Accession Number SD-5811) |
| 2477 single mutant | 2477 $\Delta hbl_{a1}$ | This study |
| 2477 double mutant | 2477 $\Delta hbl_{a1}$ Δnhe | This study |
| 2477 triple mutant | 2477 $\Delta hbl_{a1}$ Δnhe Δhbl | This study |
| 2477 quadruple mutant | 2477 $\Delta hbl_{a1}$ Δnhe Δhbl $\Delta hbl_{a2}$ | This study |
| *E. coli* DH5α | General purpose strain | Hanahan, 1983 |

TABLE 1-continued

| Bacterial strains and plasmids used in this study. | | |
|---|---|---|
| Strain or plasmid | Description | Source or Reference |
| *E. coli* GM2929 | dcm-6 dam-13::Tn9, $Cm^r$ | *E. coli* Genetic Stock Center |
| *E. coli* SS1827 | Helper strain for conjugation into *B. thuringiensis*, $Amp^r$ | Janes and Stibitz, 2006 |
| Plasmids | | |
| pMAD | Temperature-sensitive gene replacement vector, $Ery^r$, expresses β-galactosidase gene | Arnaud et al., 2004 |
| pBKJ236 | Temperature-sensitive gene replacement vector, $Ery^r$, contains 18-bp recognition site for I-SceI restriction enzyme | Janes and Stibitz, 2006 |
| pBKJ223 | Facilitator plasmid, encodes I-SceI enzyme, $Tet^r$ | Janes and Stibitz, 2006 |

DNA Isolation and Manipulation.

Genomic DNA was isolated from cultures of *B. thuringiensis* that were grown overnight with shaking. DNA was isolated either by the boiling cell-lysis method (Raffel et al., 1996), or by Protocol #3 in the Easy-DNA Kit (Invitrogen, Carlsbad, Calif.), except that prior to the addition of Solution A the cells were pelleted, resuspended in sterile water and vortexed for 2-3 min. with 50 μl of 0.1-mm diameter silica beads to enhance cell lysis. Plasmid DNA was isolated from *E. coli* using the Qiagen Spin Miniprep Kit (Qiagen Inc., Valencia, Calif.).

Transformations and Conjugations.

Competent cells of *E. coli* were electroporated in 0.2-cm cuvettes with a Gene Pulser apparatus (Bio-Rad Laboratories, Hercules, Calif.) set at 2.5 kV, 200Ω, and 25 μF. Cells were transferred to 1 ml LB, allowed to recover for 1 hr at 37° C. with shaking, and then plated on selective media. Competent cells of *B. thuringiensis* were prepared as described previously (Silo-Suh, 1994) or by the method described in Janes and Stibitz (2006). Because *B. thuringiensis* restricts methylated DNA, recombinant plasmids isolated from *E. coli* DH5α were passed through *E. coli* GM2929 (methylation-deficient strain) before being introduced into *B. thuringiensis*. pBKJ236::Δ$hbl_{a2}$ was introduced into the *B. thuringiensis* triple mutant by conjugation as described in Janes and Stibitz (2006).

Screening for Presence of Enterotoxin Genes.

Gene sequences for HBL (hblC, hblD, hblA), NHE (nheA, nheB, nheC) and cytK were obtained from strains of *B. cereus* and *B. thuringiensis*, and from the unpublished *B. cereus* UW85 partial genome sequence (D. Rasko, J. Ravel, J. Handelsman) (Table 2, SEQ ID NOS: 1-66). Sequences were aligned using the DNASTAR (Madison, Wis.) program MegAlign and regions of high conservation were selected for PCR primer sequences (see Table 3 for SEQ ID NOS: 67-86). Primers for cytK (SEQ ID NOS: 85 and 86) were designed that would amplify either variant of the gene (cytK-1 or cytK-2). The $HBL_a$ primers (SEQ ID NOS: 73-78) were based on the UW85 $hbl_a$ sequence only and were chosen so that they differed from the corresponding hbl region by 2-6 nucleotides to ensure amplification from the homologous set of genes. Primers were synthesized at Integrated DNA Technologies (Coralville, Iowa). Typical PCR reactions contained 1 μl of genomic DNA, 2 μl of 10× Taq buffer, 0.5 μM of each primer, 0.2 mM of each dNTP, 0.2 μl Taq DNA polymerase (Promega, Madison, Wis.) in a final volume of 20 μl. PCR cycle conditions consisted of an initial 1 min. denaturation at 94° C., followed by 35 cycles of 30 sec at 94° C., 1.5 min. at 55° C., 2 min. at 72° C., and a final extension of 5 min. at 72° C. PCR products were analyzed on 0.8% agarose gels.

TABLE 2

| Gene sequences for HBL, NHE, and cytK used to design PCR primers. | | |
|---|---|---|
| Gene | Organism | SEQ ID NO. |
| hblC | *B. thuringiensis* subsp. *kurstaki* 2477 (partial) | 1 |
| | *B. cereus* UW85 | 2 |
| | *B. cereus* ATCC 14579 | 3 |
| | *B. cereus* F837-76 | 4 |
| | *B. cereus* G9421 | 5 |
| | *B. thuringiensis* 97-27 serovar *konkukian* | 6 |
| hblD | *B. thuringiensis* subsp. *kurstaki* 2477 | 7 |
| | *B. cereus* UW85 | 8 |
| | *B. cereus* ATCC 14579 | 9 |
| | *B. cereus* F837-76 | 10 |
| | *B. cereus* G9421 | 11 |
| | *B. thuringiensis* serovar *konkukian* 97-27 | 12 |
| hblA | *B. thuringiensis* 2477 subsp. *kurstaki* (partial) | 13 |
| | *B. cereus* UW85 | 14 |
| | *B. cereus* ATCC 14579 | 15 |
| | *B. cereus* F837-76 | 16 |
| | *B. cereus* G9421 | 17 |
| | *B. thuringiensis* serovar *konkukian* 97-27 | 18 |
| hblCa | *B. thuringiensis* subsp. *kurstaki* 2477 hblCa1 (partial) | 19 |
| | *B. thuringiensis* subsp. *kurstaki* 2477 hblCa2 (partial) | 20 |
| | *B. cereus* UW85 | 21 |
| | *B. cereus* AS4-12 (tentative; only have 1-2x coverage) | 22 |
| | *B. cereus* 03BB108 | 23 |
| | *B. weihenstephanensis* KBAB4 | 24 |
| hblDa | *B. thuringiensis* subsp. *kurstaki* 2477 hblDa1 | 25 |
| | *B. thuringiensis* subsp. *kurstaki* 2477 hblDa2 | 26 |
| | *B. cereus* UW85 | 27 |
| | *B. cereus* AS4-12 (tentative; only have 1-2x coverage) | 28 |
| | *B. cereus* 03BB108 | 29 |
| | *B. weihenstephanensis* KBAB4 | 30 |
| hblAa | *B. thuringiensis* subsp. *kurstaki* 2477 hblAa1 (partial) | 31 |
| | *B. thuringiensis* subsp. *kurstaki* 2477 hblAa2 (partial) | 32 |
| | *B. cereus* UW85 | 33 |
| | *B. cereus* AS4-12 (tentative; only have 1-2x coverage) | 34 |
| | *B. cereus* 03BB108 | 35 |
| | *B. weihenstephanensis* KBAB4 | 36 |
| nheA | *B. thuringiensis* subsp. *kurstaki* 2477 (partial) | 37 |
| | *B. cereus* UW85 | 38 |
| | *B. cereus* 1230-88 | 39 |
| | *B. cereus* 10987 | 40 |
| | *B. cereus* ATCC 14579 | 41 |
| | *B. cereus* E3LL | 42 |
| | *B. thuringiensis* serovar *konkukian* 97-27 | 43 |
| | *B. thuringiensis* HD12 | 44 |
| nheB | *B. thuringiensis* subsp. *kurstaki* 2477 | 45 |
| | *B. cereus* UW85 | 46 |
| | *B. cereus* 1230-88 | 47 |

TABLE 2-continued

Gene sequences for HBL, NHE, and cytK used to design PCR primers.

| Gene | Organism | SEQ ID NO. |
|---|---|---|
| | *B. cereus* 10987 | 48 |
| | *B. cereus* ATCC 14579 | 49 |
| | *B. cereus* E3LL | 50 |
| | *B. thuringiensis* serovar *konkukian* 97-27 | 51 |
| | *B. thuringiensis* HD12 | 52 |
| nheC | *B. thuringiensis* subsp. *kurstaki* 2477 (partial) | 53 |
| | *B. cereus* UW85 | 54 |
| | *B. cereus* 1230-88 | 55 |
| | *B. cereus* 10987 | 56 |
| | *B. cereus* ATCC 14579 | 57 |
| | *B. cereus* E3LL | 58 |
| | *B. thuringiensis* serovar *konkukian* 97-27 | 59 |
| | *B. thuringiensis* HD12 | 60 |
| cytK | *B. cereus* 391-98 (cytK-1) | 61 |
| | *B. cereus* 1230-88 (cytK-2) | 62 |
| | *B. cereus* FM-1 (cytK-2) | 63 |
| | *B. cereus* ATCC 10987 (cytK-2) | 64 |
| | *B. cereus* ATCC 14579 (cytK-2) | 65 |
| | *B. thuringiensis* 97-27 (cytK-2) | 66 |

TABLE 3

Primers used for detection of enterotoxin genes in *Bacillus thuringiensis kurstaki* strain VBTS 2477.

| Primer | Sequence (5'-3')[a] | Melt Temp. (° C.) | Product size (nt) |
|---|---|---|---|
| hblC-F (SEQ ID NO: 67) | CAA GAG CTG TCA CGA ATC | 50.2 | 875 |
| hblC-R (SEQ ID NO: 68) | CTG CTT GAT TAG CAC GAT C | 50.2 | |
| hblD-F (SEQ ID NO: 69) | CCT ATC AAT ACT CTC GCA AC | 50.6 | 664 |
| hblD-R (SEQ ID NO: 70) | CAT CAG GTC ATA CTC TTG TG | 51.0 | |
| hblA-F (SEQ ID NO: 71) | CCT GGT AGA ATC GTA CAA G | 49.5 | 708 |
| hblA-R (SEQ ID NO: 72) | GAG CTG CAT TCT CAA TAT GC | 51.7 | |
| hblCa-F (SEQ ID NO: 73) | GCA AGT CCG AAT GTA CAA C | 51.5 | 1110 |
| hblCa-R (SEQ ID NO: 74) | CTT CGA GTT GAG TTG TTA CAC | 51.3 | |
| hblDa-F (SEQ ID NO: 75) | CTG CTA CGA ATG GTA GTA C | 49.6 | 947 |
| hblDa-R (SEQ ID NO: 76) | CTT GAT CCA CTG TCT GAT AC | 49.9 | |
| hblAa-F (SEQ ID NO: 77) | CCT GAC AAC AAC TAC TGT AG | 50.0 | 996 |
| hblAa-R (SEQ ID NO: 78) | GTC TTT CGC TGC ATT CAG | 51.5 | |
| nheA-F (SEQ ID NO: 79) | GTT AGG ATC ACA RTC ACC | 47.3-49.4 | 655 |
| nheA-R (SEQ ID NO: 80) | TCG TTT GRC TAT CTG CAG | 49.1-52.3 | |
| nheB-F (SEQ ID NO: 81) | GAT ACA GCT AGA GGA AAT GC | 50.3 | 721 |
| nheB-R (SEQ ID NO: 82) | GAT CCC ATT GTG TAC CAT TG | 51.1 | |
| nheC-F (SEQ ID NO: 83) | CAG CWG GAT TCC AAG ATG T | 52.3 | 883 |

TABLE 3-continued

Primers used for detection of enterotoxin genes in *Bacillus thuringiensis kurstaki* strain VBTS 2477.

| Primer | Sequence (5'-3')[a] | Melt Temp. (° C.) | Product size (nt) |
|---|---|---|---|
| nheC-R (SEQ ID NO: 84) | CCA RCT ATC TTT CGC TGT | 49.4-52.0 | |
| cytKdeg-F (SEQ ID NO: 85) | GCW GTR GAA GAA ACG ACT G | 50.6-53.8 | 486 |
| cytKdeg-R (SEQ ID NO: 86) | CCA ACC CAG TTW SCA GTT CC | 55.6-56.9 | |

[a]Degenerate bases: W = T or A; R = A or G; S = C or G.

Sequence Analysis of Enterotoxin Operons in *Bacillus thuringiensis* Subsp. *kurstaki* Strain VBTS 2477.

To obtain near full-length sequence of the hbl, $hbl_{a1}$, and nhe enterotoxin operons present in *B. thuringiensis* subsp. *kurstaki* strain VBTS 2477, primers near the ends of each operon were used to amplify the operon (i.e., hblC-F/hblA-R (SEQ ID NO: 67/SEQ ID NO: 72); hblCa-F, hblAa-R (SEQ ID NO: 73/SEQ ID NO: 78), nheA-F/nheC-R (SEQ ID NO: 79/SEQ ID NO: 84)), the products were purified using AMPure magnetic beads (Agencourt Bioscience, Beverly, Mass.), and the full sequence was obtained by primer walking. For $hbl_{a2}$, sequence was obtained from the PCR products generated with the following primer pairs using genomic DNA from the $\Delta hbl_{a1}$ mutant: hblCa-F/hblDa-R (SEQ ID NO: 73/SEQ ID NO: 76), and hblDa-F/hblAa-R (SEQ ID NO: 75/SEQ ID NO: 78). Typical sequencing reactions contained 1 μl of BigDye Terminator v. 3.1 mix (Applied Biosystems, Foster City, Calif.), 1.5 μl of sequencing buffer v. 3.1 (Applied Biosystems), 0.5 μM of each primer, and 5 μl of template DNA in a final reaction volume of 20 μl Cycle conditions were an initial 3 min. denaturation at 95° C., followed by 35 cycles of 10 sec. at 96° C., 3 min. 30 sec. at 58° C., and a final extension of 7 min. at 72° C. Excess dye terminators were removed using the CleanSeq magnetic bead sequencing reaction clean up kit (Agencourt Bioscience, Beverly, Mass.). Sequencing gels were run on an Applied Biosystems 3730xl automated DNA sequencing instrument at the University of Wisconsin Biotechnology Center. Data were analyzed using PE-Biosystems version 3.7 of Sequencing Analysis. Contigs were assembled using the DNASTAR software SeqMan. The nucleotide sequences of the near full-length enterotoxin operons, 2477_hbl, 2477_hbla1, 2477_hbla2, 2477_nhe, and 2477cytK-2 were deposited in Genbank under Accession numbers EU925141 (SEQ ID NO: 87), EU925142 (SEQ ID NO: 88), EU925143 (SEQ ID NO: 89), EU925144 (SEQ ID NO: 90), and EU925145 (SEQ ID NO: 91), respectively.

Generation of Deletion Constructs.

The deletion constructs were created by a method of PCR referred to as gene splicing by overlap extension, or SOEing PCR, as described in Horton et al. (1989). The primers used to create the deletion constructs are presented in Table 4 (SEQ ID NOS: 92-105). In the first round of PCR, two primer pairs were used to amplify in separate reactions a portion of the first and last gene in the enterotoxin operon. The 5' ends of the reverse primer of the first gene and the forward primer of the last gene were designed with complementary sequences of 16-18 nucleotides which enable the two fragments to be spliced together in the second round of PCR. In the second round of PCR, the fragments from the first round were mixed, along with the forward primer of the first gene and the reverse primer of the last gene (each containing a Bam HI site for cloning). Initially, the complementary ends of the two PCR fragments anneal and act as primers for extension of the spliced product, which is further amplified by the outer-most primers. For generation of the $\Delta hbl_{a1}$ and $\Delta hbl_{a2}$ constructs, the same set of outer primers were used (hblCa_Bam-F (SEQ ID NO:100), hblAa_Bam-R (SEQ ID NO:103)), but different overlapping primers were selected so that the constructs contained different sized deletions. This made for easy discrimination between the two mutations by PCR. The nucleotide sequences of the mutant operons are set forth herein: 2477Δhbl (SEQ ID NO: 110), 2477$\Delta hbl_{a1}$ (SEQ ID NO: 111), 2477$\Delta hbl_{a2}$ (SEQ ID NO: 112), and 2477Δnhe (SEQ ID NO: 113).

TABLE 4

Primers used for generation of deletion constructs by SOEing PCR.

| SOEing Primer | Sequence(5'-3')[a] | Melt Temp. (° C.) | Product size (nt) |
|---|---|---|---|
| hblC_Bam-F (SEQ ID NO: 92) | GATA**GGATCC**GTACAGCTAGAGGAAGTC | 58.9 | 735 |
| hblCtail-R (SEQ ID NO: 93) | CTTCATTTGCATGGCTTTCATCAGGTCATACTCTTG TG | 62.8 | |
| hblAtail-F (SEQ ID NO: 94) | AAAGCCATGCAAATGAAGCGAGAATGAAAGAGACCTTG C | 65.3 | 712 |

TABLE 4-continued

Primers used for generation of deletion constructs by SOEing PCR.

| SOEing Primer | Sequence(5'-3')[a] | Melt Temp. (° C.) | Product size (nt) |
|---|---|---|---|
| hblA_Bam-R (SEQ ID NO: 95) | CAAT**GGATCC**CTGTAAGCAACTCCAACTAC | 60.4 | |
| nheA_Bam-F (SEQ ID NO: 96) | CTGT**GGATCC**CAGGGTTATTGGTTACAGC | 62.2 | 815 |
| nheA_tail-R (SEQ ID NO: 97) | ATACTCCGCTGCTTCTCTCGTTTGACTATCTGCAG | 64.3 | |
| nheC_tail-F (SEQ ID NO: 98) | AGAAGCAGCGGAGTATGATTCAGCATCAAAGAGATGC | 64.6 | 744 |
| nheC_Bam-R (SEQ ID NO: 99) | CAAT**GGATCC**CCAGCTATCTTTCGCTGT | 62.1 | |
| hblCa_Bam-F (SEQ ID NO: 100) | CATT**GGATCC**GAAAGAGTGGTCATCCGAAC | 62.1 | 901 |
| hblCa1_tail-R (SEQ ID NO: 101) | TGAAACTACGCTCAATTT CTCCATCTACTTGGTTAGC | 61.9 | |
| hblAa1_tail-F (SEQ ID NO: 102) | AAATTGAGCGTAGTTTCACCAGTAGCTGCTTTTGCAAG | 64.1 | 934 |
| hblAa_Bam-R (SEQ ID NO: 103) | CTTA**GGATCC**GATCTGCTTTTTGGGATGC | 60.9 | |
| hblCa_Bam-F (SEQ ID NO: 100) | CATT**GGATCC**GAAAGAGTGGTCATCCGAAC | 62.1 | 630 |
| hblCa2_tail-R (SEQ ID NO: 104) | TTCTTTTGATCCTTTTCTCTATCGTTTCACGTGCTTC | 61.2 | |
| hblAa2_tail-F (SEQ ID NO: 105) | AGAAAAGGATCAAAAGAATGCAAGAGAGCATGCTAC | 61.5 | 691 |
| hblAa_Bam-R (SEQ ID NO: 103) | CTTA**GGATCC**GATCTGCTTTTTGGGATGC | 60.9 | |

[a]Bam HI site residues are in bold; complementary tails are underlined.

Typical conditions for the first round of PCR reactions were 1 μl genomic DNA, 5 μl 10× Pfu buffer, 0.5 μM of each primer, 0.4 mM dNTPs, and 0.5 μl Pfu DNA polymerase (Stratagene, La Jolla, Calif.) in a total volume of 50 μl. For the Δhbl$_{a2}$ construct, the template included the PCR fragments obtained with the hblCa-F/hblDa-R (SEQ ID NO:73/SEQ ID NO:76) and hblDa-F/hblAa-R (SEQ ID NO:75/SEQ ID NO:78) primer sets used with genomic DNA from the Δhbl$_{a1}$ mutant. PCR cycle conditions were 30 cycles of 30 sec. at 94° C., 30 sec. at 55° C., and 1 min. at 72° C. The PCR fragments were purified using AMPure magnetic beads. Reaction conditions for the second round of PCR were the same as the first round except the template was 0.5 μl of the PCR fragments of the 5' and 3' regions of the operon, and Taq DNA Polymerase (Promega) was used instead of Pfu DNA Polymerase. The same PCR program was used for the second round of amplification. The spliced PCR product was gel-purified using the QIAEX II gel purification kit (Qiagen).

The resulting deletion constructs were digested with Bam HI (Promega) and ligated to either pMAD (Δhbl$_{a1}$, Δnhe, Δhbl) or pBKJ236 (Δhbl$_{a2}$) that had been Bam HI-digested and treated with shrimp alkaline phosphatase (Promega). The recombinant vectors were confirmed by restriction digest analysis and the inserts were sequenced.

Gene Replacement Using pMAD or pBKJ236/pBKJ223.

Gene replacement with the pMAD constructs was carried out in a manner similar to the method described in Arnaud et al., 2004. For construction of the first mutant (Δhbl$_{a1}$; SEQ ID NO: 111) of the series, pMAD::Δhbl$_{a1}$ was electroporated into *B. thuringiensis* VBTS 2477 and transformants were selected on 0.5×TSA with Ery (3 μg/ml) and X-Gal (50 μg/ml) after two days of incubation at 28° C., the permissive temperature for plasmid replication. The gene replacement was carried out in two steps by first selecting for a single recombination event resulting in integration of the plasmid at the enterotoxin locus, and then screening for excision of the plasmid by a second recombination event and subsequent loss of the plasmid. Transformants were grown on plates containing Ery at 40.5° C., the nonpermissive temperature for replication of pMAD, to select for clones in which the plasmid had integrated into the chromosome via a single crossover event. Integrants were then grown at the permissive temperature in nonselective media to allow for a second crossover event, and then diluted into fresh media and grown at the nonpermissive temperature to cure any freely replicating plasmid. Cultures were plated for single colonies on 0.5×TSA with X-Gal at 40.5° C. and screened for white colonies, putative double recombinants. PCR analysis was performed on genomic DNA to determine whether the double recombinants had reverted to wild-type hbl$_{a1}$ or had undergone a successful gene replacement. The nhe and hbl operons were replaced with the Δnhe (SEQ ID NO: 113) and Δhbl (SEQ ID NO: 110) deletion constructs in an iterative manner to obtain the triple mutant.

A quadruple mutant using the pMAD::Δ$hbl_{a2}$ construct was not obtained due to an unexpected low frequency of recombination in the integrant containing this construct. Therefore, the pBKJ236/pBKJ223 gene replacement system was used, as described previously (Janes and Stibitz, 2006) which enhances the frequency of the second crossover event. In this system, the construct containing Δ$hbla_2$ (SEQ ID NO: 112), was introduced on a temperature-sensitive plasmid vector, pBKJ236, which carries an 18-bp recognition site for I-SceI. pBKJ236::Δ$hbl_{a2}$ was introduced into the triple mutant by conjugation, and integrants were selected on BHI with Ery at 37° C., the non-permissive temperature for replication. Integration at the $hbl_{a2}$ locus was verified by PCR analysis using one primer specific to the chromosome and one specific to the vector (hblDa2-F (SEQ ID NO: 106), 5'-GCT GCT AAA CAA AGT TGG AAT G-3', pBKJ236-R (SEQ ID NO: 107), 5'-CGT AAT ACG ACT CAC TAT AGG G-3'). Following the integration of Δ$hbla_2$ at the enterotoxin locus, a facilitator plasmid, pBKJ223, was introduced. pBKJ223 encodes the I-SceI restriction enzyme which cleaves the DNA at the site of integration, creating a substrate for recombination. pBKJ223 was electroporated into the integrant and selected on media containing Tet. A resulting transformant was grown in 0.5×TSB with Tet overnight at 28° C. and plated for single colonies on 0.5×TSA with Tet and incubated at 37° C. Colonies were screened for sensitivity to Ery to identify putative double recombinants that had lost pBKJ236 via a second crossover event. The double recombinants were screened by PCR with hblCa_Bam-F/hblAa_Bam-R (SEQ ID NO:100/SEQ ID NO:103) primers to identify clones that had retained the Δ$hbl_{a2}$ locus. The quadruple mutant was grown in 0.5×TSB at 37° C. and single colonies were patched onto plates with and without Tet to identify isolates that had been cured of pBKJ223.

Commercial Assays for Detection of Enterotoxin Proteins.

Two commercial immunoassay kits were used to detect the $L_2$ component of HBL and the NheA protein of NHE. Cultures of *B. thuringiensis* VBTS 2477, the single, double, triple, and quadruple mutants were grown for 18 hr. in 125 ml flasks containing 12 ml of BHI with 0.1% glucose. The cultures were spun down and the supernatant was filter-sterilized through a 0.22 μm pore-sized filter (Millipore Corp, Bellirica, Mass.). The cell-free culture supernatants were then assayed with the Oxoid *Bacillus cereus* enterotoxin reverse passive latex agglutination (BCET-RPLA) kit (Fisher Scientific, Pittsburgh, Pa.) and the Tecra *Bacillus* Diarrhoeal Enterotoxin (BDE) Visual Immunoassay (VIA) (3M, St. Paul, Minn.) according to the manufacturer's instructions, with the exception that in the Oxoid assay four additional dilutions were included for each sample. The assays were performed on two independent sets of cultures.

Insect Bioassays.

Bioassays were carried out using 4-day old *Trichoplusia ni* larvae (cabbage looper), 4-day old *Plutella xylostella* larvae (diamondback moth), or 2-day old *Spodoptera exigua* larvae (beet armyworm). Bacterial cultures used for treatments were grown in flasks and fermentors using media containing organic nitrogen sources (such as flours, yeast extract, fish meal, etc.) and dextrose with typical salts used in fermentation processes. Cultures were grown under aerobic conditions at 28° C. with agitation until sporulation was complete. All bacterial treatments were incorporated into warmed liquid diet which was then allowed to solidify in plates. Two or three replications were conducted for each study. Each replication tested seven dose levels of Bt whole culture (i.e., spores, vegetative materials, and constituents produced during the vegetative and sporulation phases) and an untreated control. Doses were set in a wide range to target the estimated $LC_{50}$. For *T. ni* and *S. exigua,* 30 larvae were tested per dose. For *P. xylostella* 40 larvae were tested per dose. Insects were incubated at 28°±2° C. for *T. ni* and *S. exigua*, and at 25°±2° C. for *P. xylostella* with a 12-h light/12-h dark cycle for three days. Larval mortality values from all of the replications were pooled and using log-probit analysis, a single regression line was used to estimate the 50% lethal concentration ($LC_{50}$).

Results

Detection and Sequence Analysis of Enterotoxin Genes in *Bacillus thuringiensis kurstaki* Strain VBTS 2477.

*B. thuringiensis* strain VBTS 2477 was screened for the presence of genes that encode three enterotoxins implicated in food poisoning outbreaks: HBL, NHE, and CytK. PCR primers were therefore designed to discriminate between the HBL and $HBL_a$ genes. Results from the PCR screen of VBTS 2477 indicated that all 10 enterotoxin genes (hblC, hblD, hblA, $hblC_{a1}$, $hblD_{a1}$, $hblA_{a1}$, nheA, nheB, nheC, and cytK) were present (data not shown). Sequencing of the cytK gene in VBTS 2477 revealed that it is the less toxic cytK-2 version. The $HBL_a$ genes are 77-84% identical to the HBL set in UW85.

A third HBL homolog was discovered following construction of the single deletion mutant Δ$hbl_{a1}$. A PCR product was obtained from the single mutant with the hblDa-F/hblDa-R primer set, indicating the presence of another $hblD_a$ homolog in VBTS 2477. Further analysis revealed this gene was part of a third hbl operon in VBTS 2477 (FIG. 1) which exhibits higher sequence similarity to $hbl_a$ than to hbl. Therefore, this third set of HBL genes was denoted as $hbl_{a2}$, and the $hbl_a$ detected originally was designated $hbl_{a1}$. Sequence analysis of the three near full-length hbl operons in VBTS 2477 shows that the $hbl_{a1}$ and $hbl_{a2}$ gene sequences are 96-97% identical (Table 5) and the deduced protein sequences are 97-98% identical. The hbl genes are 76-84% identical to $hbl_{a1}$ and $hbl_{a2}$ genes, while the deduced proteins are 68-85% identical (Table 5).

TABLE 5

Nucleotide sequence identity (%) of the hbl homologues in VBTS 2477.

| Gene | hblC | $hblC_{a1}$ | Gene | hblD | $hblD_{a1}$ | Gene | hblA | $hblA_{a1}$ |
|---|---|---|---|---|---|---|---|---|
| hblC | 100 | 82 | hblD | 100 | 83 | hblA | 100 | 78-83 |
| $hblC_{a2}$ | 81 | 96 | $hblD_{a2}$ | 84 | 97 | $hblA_{a2}$ | 76-78 | 96 |

Sequence analysis of the cytK gene in strain VBTS 2477 revealed that it is the less toxic variant, cytK-2 (Fagerlund et al., 2004). The CytK-2 protein is 89% identical to CytK-1 at the amino acid level and exhibits only about 20% of the toxicity of CytK-1 toward human intestinal cells (Fagerlund et al., 2004), making its role in virulence uncertain. cytK-2 was not deleted from strain VBTS 2477.

Generation of Deletion Constructs and Gene Replacement.

Figure 2:
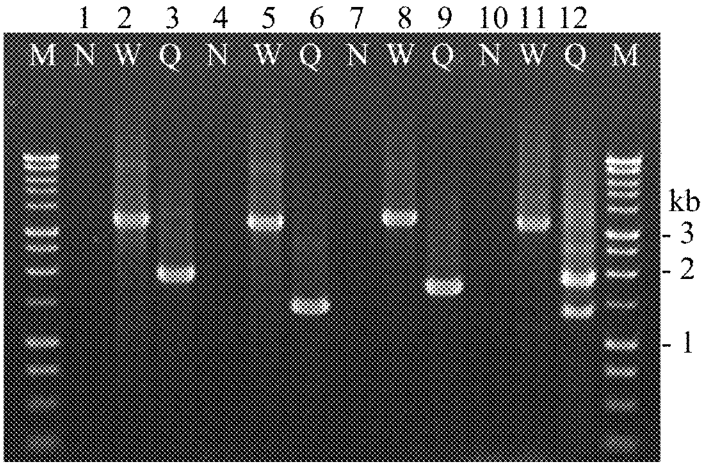
FIG. 2 depicts a PCR analysis of *B. thuringiensis* VBTS 2477 and quadruple enterotoxin deletion mutant. PCR primers (see Table 2) were used to amplify: $hbl_{a1}$, lanes 1-3 (hblCa-F/hblAa-R) (SEQ ID NO:73/SEQ ID NO:78); nhe, lanes 4-6 (nheA-F/nheC-R) (SEQ ID NO:79/SEQ ID NO:84); hbl lanes 7-9 (hblC-F/hblA-R) (SEQ ID NO:67/SEQ ID NO:72); $hbl_{a2}$, lanes 10-12 (hblCa_Bam-F/hblAa_Bam-R) (SEQ ID NO:100/SEQ ID NO:103). Abbreviations: M: molecular weight standards (1 kb ladder; Promega Corporation, Madison, Wis.), N: negative control, W: wild-type strain, Q: quadruple mutant.

SOEing PCR was used to generate deletion constructs of HBL, $HBL_{a1}$, $HBL_{a2}$, and NHE that contained a portion of the first enterotoxin gene spliced to a portion of the last enterotoxin gene of the operon, essentially creating a version of the operon missing a large internal portion of the operon encompassing the end of the first gene, the entire middle gene, and the beginning of the final gene. The deletion constructs contained about 600-900 nucleotides on either side of the deletion for homologous recombination. The deletion constructs were cloned into a temperature-sensitive gene replacement vector (pMAD for $\Delta hbl_{a1}$, Δnhe, and Δhbl; pBKJ236 for $\Delta hbl_{a2}$) and successive gene replacements were carried out to introduce the deletions in the order $\Delta hbl_{a1}$, Δnhe, Δhbl, and $\Delta hbl_{a2}$ (FIG. 2). Attempts were made to obtain a $\Delta hbl_{a2}$ mutant using the pMAD::$\Delta hbl_{a2}$ construct; however, an unexpected low frequency of recombination was observed in the integrant, and the double recombinants identified had reverted to wild-type $hbl_{a2}$. Therefore, the pBKJ236/pBKJ223 gene replacement system used previously in *B. anthracia* was used to generate the final deletion. This two-plasmid system utilizes a temperature-sensitive gene replacement plasmid (pBKJ236) and a second plasmid that promotes recombination at the site of the integrated gene replacement vector (Janes and Stibitz, 2006).

Detection of Enterotoxin Proteins with Commercial Kits.

*B. thuringiensis* strain VBTS 2477, the single mutant ($\Delta hbl_{a1}$) and the double ($\Delta hbl_{a1}$ Δnhe) mutant each exhibited a strong agglutination response (Table 6) when tested with the Oxoid BCET-RPLA kit, which detects the $L_2$ component of HBL (Beecher & Wong, 1994). The triple deletion mutant, in which hbl is deleted, exhibited a negative phenotype, indicating that expression of the $L_2$ protein was abolished in this mutant. Since the $hbl_{a2}$ operon remained intact in the triple mutant, either $L_{2(a2)}$ is not expressed in strain VBTS 2477 or it does not react with the anti-$L_2$ antibody in the RPLA kit. Hemolysis on sheep blood agar suggests that $L_{2(a2)}$ is expressed in VBTS 2477 since the hemolytic activity of the quadruple mutant is diminished compared to the triple mutant (data not shown). Therefore, it is likely that $L_{2a}$ is antigenically distinct from $L_2$. In the Tecra BDE assay, which detects NheA, both the wild type and the single mutant ($\Delta hbl_{a1}$) exhibited positive reactions (Table 6). The double mutant, in which nhe had been deleted, exhibited a negative reaction, as did the triple and quadruple mutants.

TABLE 6

Detection of HBL and NHE proteins in *B. thuringiensis* subsp. *kurstaki* strain VBTS 2477 and deletion mutants by commercial immunoassays.

| Strain | Genotype | Oxoid RPLA[a] | Tecra BDE[b] |
|---|---|---|---|
| VBTS 2477 | Wildtype | 1024 | 4 |
| Single mutant | $\Delta hbl_{a1}$ | 1024 | 4 |
| Double mutant | $\Delta hbl_{a1}$ Δnhe | 1024 | 1 |
| Triple mutant | $\Delta hbl_{a1}$ Δnhe Δhbl | Neg | 1 |
| Quadruple mutant | $\Delta hbl_{a1}$ Δnhe Δhbl $\Delta hbl_{a2}$ | Neg | 1 |

[a]RPLA assay results are reported as the highest dilution (in a series of two-fold dilutions) that gives a positive agglutination.
[b]BDE assay results are reported according to the manufacturer's instructions where scores of 3, 4, or 5 are positive, and 1 or 2 are negative.

Toxin Production and Efficacy.

SDS-PAGE analysis indicated that VBTS 2477 and the quadruple mutant produce similar quantities of the insecticidal crystal protoxins (Table 7). The wild type and quadruple mutant had similar insecticidal activity against three lepidopteran species: cabbage looper, diamondback moth, and beet armyworm (Table 8).

TABLE 7

Crystal toxin accumulation in cultures from 7.5 L fermentors.*

| Strain | Protoxin in culture broth ($mg\ ml^{-1}$) | Proportion of crystal toxin as 135-kDa protoxin (%) | Proportion of crystal toxin as 60-kDa protoxin (%) |
|---|---|---|---|
| VBTS 2477 | 8.4 | 63 | 37 |
| VBTS 2477, quadruple mutant | 11.6 | 69 | 31 |

*Protein quantified by gel analysis software (BioRad Quantity One ® 4.1.1) of SDS-PAGE gels stained with Colloidal Blue (Invitrogen). Values represent the result of a single experiment.

TABLE 8

Insecticidal activity against lepidopteran larvae. *B. thuringiensis* cultures from 7.5 L fermentors were fed to 4-day old *T. ni*, 2-day old *S. exigua*, and 4-day old *P. xylostella* larvae. Larval mortality was assessed after 3 days.

| | Insecticidal activity $LC_{50}$* ($\mu g\ ml^{-1}$ diet against each lepidopteran species) | | |
|---|---|---|---|
| Strain | *T. ni* (95% CI) | *S. exigua* (95% CI) | *P. xylostella* (95% CI) |
| VBTS 2477 | 168 (158-178) | 653 (538-773) | 11.5 (7.48-18.1) |
| VBTS 2477, quadruple mutant | 145 (131-160) | 632 (545-730) | 11.1 (9.91-12.8) |

*Values represent the mean of three replicates for *T. ni*, two replicates for *S. exigua* and *P. xylostella*. For each replicate 30 larvae of *T. ni* and *S. exigua*, and 40 larvae of *P. xylostella* were tested. CI indicates confidence interval.

Example 2

Materials and Methods

A quadruple mutant ($\Delta hbl_{a1}$ Δnhe Δhbl $\Delta hbl_{a2}$) was created in *B. thruingiensis* subsp. *aizawai* strain VBTS 2478.

Preparation of Competent Cells of Strain *B. thuringiensis* subsp. *aizawai* (Bta) Strain VBTS 2478.

Competent cells of Bta strain VBTS 2478 were prepared using the protocol described for strain VBTS 2477.

Gene Replacement in *B. thuringiensis* subsp. *aizawai* (Bta) Strain 2478.

We determined by PCR analysis that Bta strain VBTS 2478 has the genes that encode HBL, $HBL_{a1}$, $HBL_{a2}$, and NHE (data not shown). Bta strain VBTS 2478 was transformed using the protocol described for VBTS 2477. The following constructs were used in construction of the quadruple enterotoxin-deficient mutant of VBTS 2478: pMAD::Δ2477hbl, pMAD::Δ2477$hbl_{a1}$, pMAD::Δ2477$hbl_{a2}$, and pMAD::Δ2477nhe. These constructs were transformed into VBTS 2478 sequentially, and gene replacements were performed iteratively. Transformants were selected on LB agar plates containing 1 μg/ml of Ery and 50 μg/ml of X-Gal (details as in Example 1). Integrants were obtained by growing transformants at the nonpermissive temperature (the replication origin on pMAD is temperature sensitive). Following second cross-over events, target gene deletion was confirmed by PCR analysis of genomic DNA using appropriate primer pairs (Tables 1, 3, and 9).

TABLE 9

| Primers used in gene replacement in *B. thuringiensis* strains 2478 and 2481. | | | |
|---|---|---|---|
| Name | Sequence (5' to 3') | Note | SEQ ID NO. |
| hblCa2-f | CTTTCTACAGGGAAGGATTTAGAA | specific for $hbl_{a2}$ in strain VBTS 2478* | 108 |
| hblCa-450f | CTTAATTCAGAGGGAACAGGA | Specific for both $hbl_{a1}$ and $hbl_{a2}$* | 109 |

*After mutagenesis of $hbl_{a1}$ in strain 2478, PCR analysis confirmed the existence of a second $hbl_{a}$ homolog, $hbl_{a2}$.
The sequencing data of $hbl_{a2}$ showed that this operon was truncated at the 5' end.

Commercial Assays for Detection of Enterotoxin Proteins.

Cultures of VBTS 2478 and the VBTS 2478 quadruple enterotoxin-deficient mutant were grown in Brain Heart Infusion broth for 16 hours at 32° C. with shaking at 200 rpm. Optical densities for the cultures ranged from 1.50 to 1.73. Cultures were centrifuged at 13000×g at 4° C. The supernatant was sterilized by passing through 0.2μ low protein binding filters. Samples were aliquoted and stored at −20 C until use. VBTS 2478 wild type and mutant samples were assayed according to directions specified in the Oxoid BCET-RPLA detection kit to test for production of Hbl enterotoxin, and according to directions specified in the Tecra BDEVIA detection kit for production of Nhe enterotoxin.

Results

Construction of Quadruple Enterotoxin-Deficient Mutant of *B. Thuringiensis* subsp. *aizawai* (Bta) Strain VBTS 2478.

Figure 3:
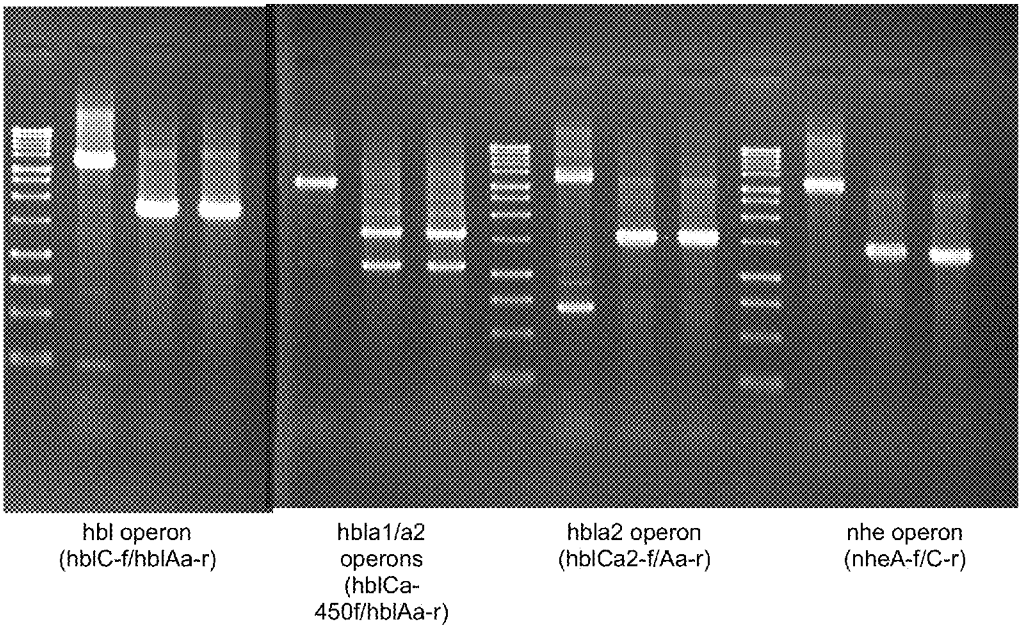
FIG. 3 depicts PCR confirmation of quadruple enterotoxin-deficient mutant of VBTS 2478. WT, VBTS 2478 wild type; 1B and 3B, two quadruple mutants of strain 2478; M, DNA 1 kb ladder from Promega Corporation (from bottom to top (size in kb): 0.25, 0.5, 0.75, 1, 1.5, 2, 2.5, 3, 4, 5, 6, 8, 10, respectively).

PCR confirmed successful construction of a quadruple enterotoxin-deficient mutant of Bta strain VBTS 2478 (FIG. 3). Partial sequences for $hblA_{a2}$ and $hblD_{a2}$ in strain 2478 are depicted by SEQ ID NOs.: 114 and 115 respectively.

Detection of Enterotoxin Proteins with Commercial Kits.

*B. thuringiensis* strain VBTS 2478 exhibited a strong agglutination response when tested with the Oxoid BCET-RPLA kit, which detects the $L_2$ component of HBL (Beecher & Wong, 1994). The quadruple deletion mutant ($\Delta hbl_{a1}$ Δnhe Δhbl $\Delta hbl_{a2}$), in which hbl and hbl homologs are deleted, exhibited a negative phenotype, indicating that expression of the Hbl proteins was abolished in this mutant (data not shown). In the Tecra BDE assay, which detects NheA, wild type VBTS 2478 exhibited a positive reaction, whereas the quadruple mutant, in which nhe had been deleted, exhibited a negative reaction, indicating that Nhe enterotoxin was not produced (data not shown).

Example 3

Materials and Methods

A double mutant (Δhbl Δnhe) was created in *B. thuringiensis* strain VBTS 2481.

Preparation of Competent Cells of *B. Thuringiensis* Subsp. *Israelensis* (Bti) Strain VBTS 2481.

Competent cells of Bti strain VBTS 2481 were prepared using a protocol similar to that described for strain VBTS 2477.

Gene Replacement in *B. Thuringiensis* Subsp. *Israelensis* (Bti) Strain VBTS 2481.

PCR analysis of genomic DNA using degenerate primers specific for $hbl_{a1}$ and $hbl_{a2}$ did not yield any products indicating that VBTS 2481 does not contain $hbl_{a1}$ or $hbl_{a2}$; PCR analysis did confirm that VBTS 2481 contains hbl and nhe (data not shown). Bti strain VBTS 2481 was transformed using a protocol similar to that described for VBTS 2477. The following constructs were used in construction of the double enterotoxin-deficient mutant of VBTS 2481: pMAD::Δ2477hbl, and pMAD::Δ2477nhe. These constructs were transformed into VBTS 2481 sequentially, and gene replacements were performed iteratively. Transformants were selected on LB agar plates containing 1 μg/ml of Ery and 50 μg/ml of X-Gal (details as in Example 1). Integrants were obtained by growing transformants at the nonpermissive temperature (the replication origin on pMAD is temperature sensitive). Additional steps can be taken, if needed, to stabilize genetic material found in *Bacillus* strains, for example, the plasmid carrying cry genes. Methods for stabilizing plasmids during gene replacement are known in the art.

Results

Construction of Double Enterotoxin-Deficient Mutant of *B. Thuringiensis* Subsp. *israelensis* (Bti) Strain VBTS 2481.

Figure 4:
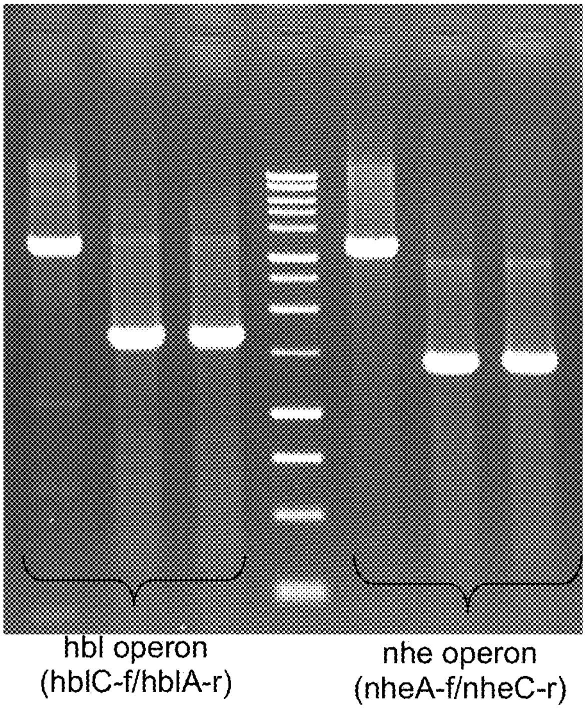
FIG. 4 depicts PCR confirmation of the double enterotoxin-deficient mutant of VBTS 2481. WT, VBTS 2481 wild type; d1 and d2, two double mutants of VBTS 2481; M, DNA 1 kb ladder from Promega Corporation.

PCR confirmed successful construction of double enterotoxin-deficient mutant of VBTS 2481 (FIG. 4). Partial sequences for strain 2481 hblC (single coverage), hblA (single coverage), nheA (single coverage), and nheC (single coverage) are depicted by SEQ ID NOs.: 116, 117, 118, and 119 respectively.

LITERATURE CITED

The following references are incorporated herein by reference as if set forth in their entirety.

Arnaud M, Chastanet A, Débarbouillé M. (2004) "New vector for efficient allelic replacement in naturally nontransformable, low-GC-content, gram-positive bacteria." Appl. Environ. Microbiol. 70:6887-6891.

Arnesen L P S, Fagerlund A, Granum P E. (2008) "From soil to gut: *Bacillus cereus* and its food poisoning toxins." FEMS Microbiol. Rev. 32:579-606.

Beecher D J, MacMillan J D. (1991) "Characterization of the components of hemolysin BL from *Bacillus cereus*." Infect. Immun. 59:1778-84.

Beecher D J, Wong A C. (1994) "Identification and analysis of the antigens detected by two commercial *Bacillus cereus* diarrheal enterotoxin immunoassay kits." Appl. Environ. Microbiol. 60:4614-4616.

Beecher D J, Wong A C. (2000) "Tripartite haemolysin BL: isolation and characterization of two distinct homologous sets of components from a single *Bacillus cereus* isolate." Microbiology 146:1371-1380.

Benbrook C M, Groth E, Halloran J M, Hansen M K, Marquardt S. (1996) "Pest management at the crossroads." Consumers Union, Yonkers, N.Y.

Cook R J, Bruckart W L, Coulson J R, Goettel M S, Humber R A, Lumsden R D, Maddox J V, McManus M L, Moore L, Meyer S F, Quimby P C Jr, Stack J P, Vaughn J L. (1996)

"Safety of microorganisms intended for pest and plant disease control: a framework for scientific evaluation." Biol. Control 7:333-351.

Fagerlund A, Lindbäck T, Storset A K, Granum P E, Hardy S P. (2008) "*Bacillus cereus* Nhe is a pore-forming toxin with structural and functional properties similar to the ClyA (HlyE, SheA) family of haemolysins, able to induce osmotic lysis in epithelia." Microbiology 154:693-704.

Fagerlund A, Ween A, Lund T, Hardy S P, Granum P E. (2004) "Genetic and functional analysis of the cytK family of genes in *Bacillus cereus*." Microbiology 150:2689-2697.

From C, Pukall R, Schumann P, Hormazábal V, Granum P E. (2005) "Toxin-producing ability among *Bacillus* Spp. outside the *Bacillus cereus* group." Appl. Environ. Microbiol. 71:1178-1183.

Granum P E, O'Sullivan K, Lund T. (1999) "The sequence of the non-haemolytic enterotoxin operon from *Bacillus cereus*." FEMS Microbiol. Lett. 177:225-9.

Handelsman J, Raffel S, Mester E H, Wunderlich L, Grau C R. (1990) "Biological control of damping-off of alfalfa seedlings with *Bacillus cereus* UW85." Appl. Environ. Microbiol 56:713-718.

Heinrichs J H, Beecher D J, MacMillan J D, Zilinskas B A. (1993) "Molecular cloning and characterization of the hblA gene encoding the B component of hemolysin BL from *Bacillus cereus*." J. Bacteriol. 175:6760-6.

Horton R M, Hunt H D, Ho S N, Pullen J K, Pease L R. (1989) "Engineering hybrid genes without the use of restriction enzymes: gene splicing by overlap extension." Gene 77:61-8.

Janes B K, Stibitz S. (2006) "Routine markerless gene replacement in *Bacillus anthracis*." Infect. Immun. 74:1949-53.

Lindbäck T, Økstad O A, Rishovd A L, Kolstø A B. (1999) "Insertional inactivation of hblC encoding the $L_2$ component of *Bacillus cereus* ATCC 14579 haemolysin BL strongly reduces enterotoxigenic activity, but not the haemolytic activity against human erythrocytes." Microbiology 145:3139-3146.

Lund T, De Buyser M L, Granum P E. (2000) "A new cytotoxin from *Bacillus cereus* that may cause necrotic enteritis." Mol. Microbiol. 38:254-261.

Lund T, Granum P E. (1996) "Characterization of a non-haemolytic enterotoxin complex from *Bacillus cereus* isolated after a foodborne outbreak." FEMS Microbiol. Lett. 141:151-156.

Raffel S J, Stabb E V, Milner J L, Handelsman J. (1996) "Genotypic and phenotypic analysis of zwittermicin A-producing strains of *Bacillus cereus*." Microbiology 142:3425-36.

Ramarao N, Lereclus D. (2006) "Adhesion and cytotoxicity of *Bacillus cereus* and *Bacillus thuringiensis* to epithelial cells are FlhA and PlcR dependent, respectively." Microbes Infect. 8:1483-1491.

Ryan P A, MacMillan J D, Zilinskas B A. (1997) "Molecular cloning and characterization of the genes encoding the $L_1$ and $L_2$ components of hemolysin BL from *Bacillus cereus*." J. Bacteriol. 179:2551-2556.

Shang H, Chen J, Handelsman J, Goodman R M. (1999) "Behavior of *Pythium torulosum* zoospores during their interaction with tobacco rots and *Bacillus cereus*." Curr. Microbiol. 38:199-204.

Silo-Suh L A, Stabb E V, Raffel S J, Handelsman J. (1998) "Target range of zwittermicin A, an aminopolyol antibiotic from *Bacillus cereus*." Curr. Microbiol 37:6-11.

Silo-Suh L A, Lethbridge B J, Raffel S J, He H, Clardy J, Handelsman J. (1994) "Biological activities of two fungistatic antibiotics produced by *Bacillus cereus* UW85." Appl. Environ. Microbiol. 60:2023-30.

We claim:

1. An isolated *Bacillus thuringiensis* strain comprising a disabling mutation at locus nhe whereby NHE enterotoxin is not produced, a disabling mutation at locus $hbl_{a2}$ whereby enterotoxin $HBL_{a2}$ is not produced, and a disabling mutation at one or more of loci hbl and $hbl_{a1}$, whereby at least one of enterotoxins HBL and $HBL_{a1}$ is not produced.

2. A *Bacillus thuringiensis* strain as claimed in claim 1, wherein the disabling mutation at locus nhe comprises the disabling mutation of SEQ ID NO:111; wherein the disabling mutation at locus $hbla_2$ comprises the disabling mutation of SEQ ID NO:110; and wherein the one or more of the hbl and $hbl_{a1}$ loci comprise the disabling mutation of SEQ ID NO: 112 and SEQ ID NO: 113, respectively.

3. A *Bacillus thuringiensis* strain as claimed in claim 1 that is insecticidal.

4. A *Bacillus thuringiensis* strain as claimed in claim 1 that produces δ-endotoxin.

* * * * *